United States Patent
Stahl et al.

(10) Patent No.: US 10,597,359 B2
(45) Date of Patent: Mar. 24, 2020

(54) HIGH-SOLUBILITY THIOETHER QUINONES

(71) Applicant: Wisconsin Alumni Research Foundation, Madison, WI (US)

(72) Inventors: Shannon S. Stahl, Madison, WI (US); James B. Gerken, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 16/150,405

(22) Filed: Oct. 3, 2018

(65) Prior Publication Data

US 2019/0055193 A1 Feb. 21, 2019

Related U.S. Application Data

(63) Continuation-in-part of application No. PCT/US2018/020086, filed on Feb. 28, 2018.

(60) Provisional application No. 62/464,441, filed on Feb. 28, 2017, provisional application No. 62/567,292, filed on Oct. 3, 2017.

(51) Int. Cl.
| | |
|---|---|
| *C07C 309/42* | (2006.01) |
| *C07C 323/66* | (2006.01) |
| *C07C 319/14* | (2006.01) |
| *C07D 209/48* | (2006.01) |
| *C07D 231/18* | (2006.01) |
| *C07D 487/04* | (2006.01) |
| *C07D 285/14* | (2006.01) |
| *H01M 8/18* | (2006.01) |

(52) U.S. Cl.
CPC .......... *C07C 309/42* (2013.01); *C07C 319/14* (2013.01); *C07C 323/66* (2013.01); *C07D 209/48* (2013.01); *C07D 231/18* (2013.01); *C07D 285/14* (2013.01); *C07D 487/04* (2013.01); *H01M 8/188* (2013.01)

(58) Field of Classification Search
CPC ... C07C 309/42; C07C 323/66; C07C 319/14; C07D 209/48; C07D 231/18; C07D 487/04; C07D 285/14
See application file for complete search history.

(56) References Cited

U.S. PATENT DOCUMENTS

| | | |
|---|---|---|
| 2,935,518 A | 5/1960 | Reetz |
| 2014/0370403 A1 | 12/2014 | Narayan et al. |
| 2015/0263371 A1 | 9/2015 | Stahl et al. |

FOREIGN PATENT DOCUMENTS

| | | |
|---|---|---|
| JP | 09054404 A | 2/1997 |
| JP | 2012-116800 A | 6/2012 |
| WO | 2015048550 A1 | 4/2015 |
| WO | 201612200 A1 | 8/2016 |

OTHER PUBLICATIONS

Akutsu, H. et al., "New ionic acceptors Br2XQNHCH2SO3- and their charge transfer salts", Physica B: Condensed Matter, Elsevier, Amsterdam, vol. 405, No. 11, Jun. 1, 2010, pp. S2-S5.

Huynh, Mioy T. et al., "Quinone 1e- and 2 e- /2 H+ Reduction Potentials: Identification and Analysis of Deviations from Systematic Scaling Relationships", Journal of the American Chemical Society, vol. 138, No. 49, Dec. 14, 2016, pp. 15903-15910.

*Primary Examiner* — Sun Jae Yoo
(74) *Attorney, Agent, or Firm* — Boyle Fredrickson S.C.

(57) ABSTRACT

Substituted hydroquinones and quinones and methods of synthesizing such compounds are disclosed herein. The substituted hydroquinones have the formula:

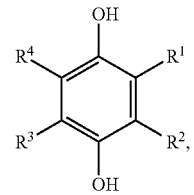

while the substituted quinones have the corresponding oxidized structure (1,4-benzoquinones). One, two, three, or all four of $R^1$, $R^2$, $R^3$ and $R^4$ comprise a thioether moiety and a sulfonate moiety, and wherein each $R^1$, $R^2$, $R^3$ and $R^4$ that does not comprise a thioether and a sulfonate moiety sulfonate moiety is independently a hydrogen, an alkyl or an electron withdrawing group. The substituted hydroquinones and quinones are soluble in water, stable in aqueous acid solutions, and have a high reduction potential in the oxidized form. Accordingly, they can be used as redox mediators in emerging technologies, such as in mediated fuel cells or organic-mediator flow batteries.

12 Claims, 49 Drawing Sheets

HIGH-SOLUBILITY THIOETHER QUINONES

CROSS-REFERENCE TO RELATED APPLICATIONS

This application is a continuation-in-part of International Application No. PCT/US2018/020086 filed on Feb. 28, 2018, which claims the benefit of U.S. provisional Application No. 62/464,441 filed on Feb. 28, 2017; and this application claims the benefit of U.S. provisional Application No. 62/567,292 filed on Oct. 3, 2017. Each of these applications is incorporated by reference herein in its entirety and for all purposes.

STATEMENT REGARDING FEDERALLY SPONSORED RESEARCH/DEVELOPMENT

This invention was made with government support under DE-AC05-76RL01830 awarded by the US Department of Energy. The government has certain rights in the invention.

BACKGROUND

The quinone/hydroquinone redox couple is used in many different technologies and has been extensively studied. In U.S. Patent Publication No. 2015/0263371, which is incorporated by reference herein in its entirety, we disclosed using the quinone/hydroquinone redox couple as a charge transfer mediator to facilitate more efficient electrocatalytic oxygen reduction in electrochemical cells. However, in the context of emerging electrochemical cell technologies, such as organic mediator flow batteries and mediated fuel cells, the available quinones are inadequate.

In the context of such technologies, effective redox mediators must have a reduction potential close to the thermodynamic potential for reduction of oxygen to water, high solubility in water, and stability in aqueous solutions under the conditions used in such applications. Although the unsubstituted hydroquinone/1,4-benzoquinone redox couple has a sufficiently high reduction potential in the oxidized form, it has relatively low solubility in water and is unstable in acid solution.

Hydroquinone can be sulfonated to yield useful compounds, such as the commercially available potassium hydroquinone monosulfonate. More vigorous sulfonation conditions give rise to the 2,5- and 2,6-disulfonated isomers.[1] These sulfonate salts have high water solubility compared to the parent hydroquinone, and the solubility of the acid is even higher. Aerobic or electrochemical oxidation of these compounds produces the corresponding para-quinone. Sulfonation of catechol gives the 3,5-disulfonate, which can be oxidized to an ortho-quinone. These quinones have been proposed as redox-active species in flow batteries.[2]

We undertook experiments on these quinones to determine their suitability for use in a mediated fuel cell. To our dismay, the mono- and di-substituted quinones described above all proved to be unstable in aqueous acid, even at low temperature (see Scheme 1). The condensation of the mono-sulfonated quinone is presumed to be analogous to previously studied decomposition reactions of benzoquinone and toluquinone.[3] The presence of two sulfonate groups prevents polymerization, but addition of water still takes place, even in 1 M $H_2SO_4$. Although the resulting dihydroxyquinone disulfonates are stable in solution, their reduction potentials are too low to be useful in a flow battery or fuel cell. The addition of water has been since confirmed for the disulfonated ortho-quinone in a recent paper by Yang, et al.[4]

Scheme 1:
Quinone decomposition pathways that prevent reversible cycling. The quinone products of the bottom two reactions have unusably low reduction potentials.

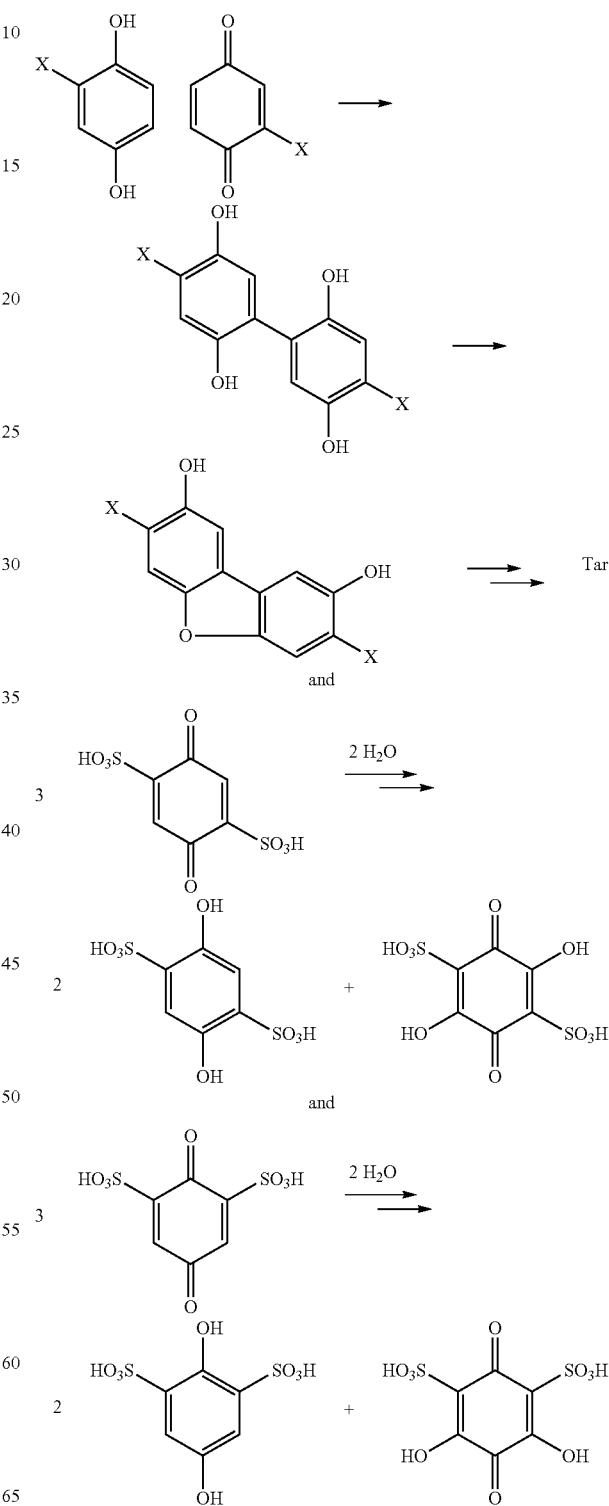

Accordingly, there is a need in the art for highly substituted hydroquinones/quinones with substituents that result in a quinone reduction potential at least as high as the reduction potential of unsubstituted benzoquinone, while also having the greater stability exhibited by low-potential polysubstituted quinones. In addition, there is a need in the art for improved methods for synthesizing such highly substituted hydroquinones/quinones. Water soluble substituted hydroquinones/quinones having such properties could function as improved redox mediators in electrochemical cells, particularly to facilitate oxygen reduction in mediated fuel cells or in organic-mediator flow batteries.

SUMMARY

We disclose herein highly substituted hydroquinones/quinones having reduction potentials in the oxidized state at least as high as benzoquinone that are also water soluble and stable in acid solution, as well as a new method of synthesizing such compounds.

In a first aspect, the disclosure encompasses a substituted hydroquinone having the formula:

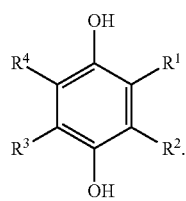

One, two, three, or all four of $R^1$, $R^2$, $R^3$ and $R^4$ include both a thioether moiety and a sulfonate moiety, and each $R^1$, $R^2$, $R^3$ and $R^4$ that does not include a thioether and a sulfonate moiety is independently a hydrogen, an alkyl, or an electron withdrawing group. This first aspect also includes the oxidized form (the substituted 1,4-benzoquinone form) of such compounds.

In some embodiments, each of the one, two, three, or four of $R^1$, $R^2$, $R^3$ and $R^4$ that includes a thioether moiety and a sulfonate moiety independently has the chemical structure $—S(CH_2)_nSO_3^-$, where n is 1, 2, 3 or 4. In some such embodiments, each n is independently 2 or 3.

In some embodiments, three or all four of $R^1$, $R^2$, $R^3$ and $R^4$ include both a thioether moiety and a sulfonate moiety. In some such embodiments where three of $R^1$, $R^2$, $R^3$ and $R^4$ include both a thioether moiety and a sulfonate moiety, the $R^1$, $R^2$, $R^3$ or $R^4$ that does not include both a thioether and a sulfonate moiety is an electron withdrawing group. Such electron withdrawing groups may include, without limitation, nitrile (cyanide), ketones, amides, $—CF_3$, $—SF_5$, imides, imidazoles, benzimidazoles, or pyrazoles.

In some embodiments, all four of $R^1$, $R^2$, $R^3$ and $R^4$ include both a thioether moiety and a sulfonate moiety.

In some embodiments, each of the one, two, three, or four of $R^1$, $R^2$, $R^3$ and $R^4$ that includes both a thioether moiety and a sulfonate moiety has the same chemical structure.

In some embodiments, the hydroquinone form is:

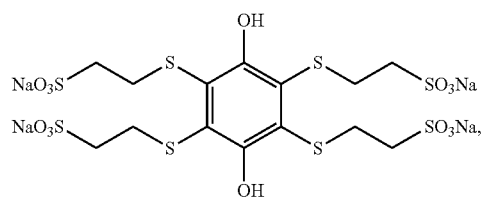

or another salt, ester, or acids of this compound.

In some embodiments, the hydroquinone form is:

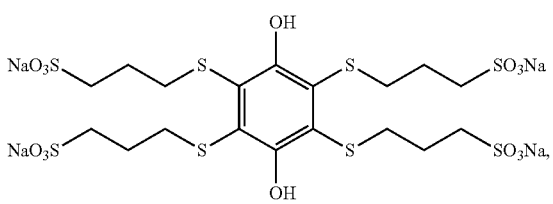

or another salt, ester, or acid of this compound.

In some embodiments, the hydroquinone form is:

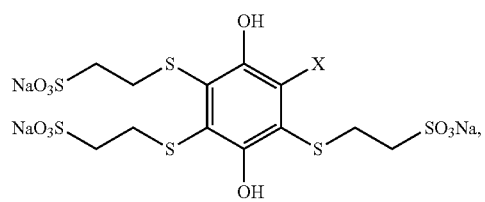

where X is a an alkyl or electron withdrawing group; or another salt, ester or acid of this compound.

In some embodiments, the hydroquinone form is:

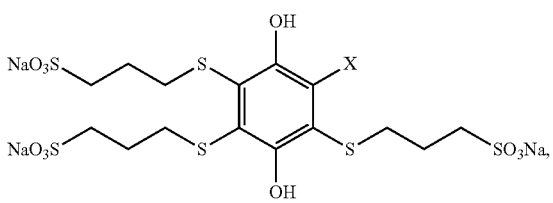

where X is a an electron withdrawing group; or another salt, ester or acid of this compound.

Exemplary electron withdrawing groups include, without limitation, nitrile (cyanide), $—CF_3$, $—SF_5$, imides, imidazoles, benzimidazoles, or pyrazoles.

In some embodiments, the hydroquinone form is:

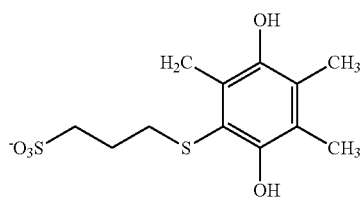

or another salt, ester, or acid of this compound.

In some embodiments, the substituted hydroquinone or benzoquinone is more soluble in water than the corresponding unsubstituted hydroquinone or benzoquinone, is stable in 1 M $H_2SO_4$, and has a reduction potential in the oxidized form that is equal to or greater than the reduction potential of unsubstituted 1,4-benzoquinone.

In a second aspect, the disclosure encompasses a method of installing one or more thioether sulfonate moieties onto one or more unsubstituted carbon atoms of a hydroquinone or 1,4-benzoquinone ring. The method includes the steps of (a) contacting a first 1,4-benzoquinone having a first unsubstituted carbon atom on the benzoquinone ring with a first mercaptoalkylsulfonate, which leads to the formation of a first hydroquinone adduct having the corresponding first thioether sulfonate moiety installed onto the first unsubstituted carbon atom; and (b) oxidizing the first hydroquinone adduct by applying an electric current to it, which leads to the formation of a second 1,4 benzoquinone having the first thioether sulfonate moiety installed onto the first unsubstituted carbon atom. Some embodiments further include the step of oxidizing a hydroquinone having one or more unsubstituted carbon atoms on the hydroquinone ring to form the first 1,4-benzoquinone.

In some embodiments, the second 1,4 benzoquinone has a second unsubstituted carbon atoms on the benzoquinone ring, and the method further includes the steps of (c) contacting the second 1,4-benzoquinone with a second mercaptoalkylsulfonate, which leads to the formation of a second hydroquinone adduct having the corresponding second thioether sulfonate moiety installed onto the second unsubstituted carbon atom; and (d) oxidizing the second hydroquinone adduct by applying an electric current to it, which leads to the formation of a third 1,4 benzoquinone having the second thioether sulfonate moiety installed onto the second unsubstituted carbon atom.

In some such embodiments, the third 1,4 benzoquinone has a third unsubstituted carbon atoms on the benzoquinone ring, and the method further includes the steps of (e) contacting the third 1,4-benzoquinone with a third mercaptoalkylsulfonate, which leads to the formation of a third hydroquinone adduct having the corresponding third thioether sulfonate moiety installed onto the third unsubstituted carbon atom; and (f) oxidizing the third hydroquinone adduct by applying an electric current to it, which leads to the formation of a fourth 1,4 benzoquinone having the third thioether sulfonate moiety installed onto the third unsubstituted carbon atom.

In some such embodiments, the fourth 1,4 benzoquinone has a fourth unsubstituted carbon atoms on the benzoquinone ring, and the method further includes the step of (g) contacting the fourth 1,4-benzoquinone with a fourth mercaptoalkylsulfonate, which leads to the formation of a fourth hydroquinone adduct having the corresponding fourth thioether sulfonate moiety installed onto the fourth unsubstituted carbon atom.

In some embodiments, the first 1,4-benzoquinone is a 1,4-benzoquinone having four unsubstituted carbon atoms on the benzoquinone ring.

In some embodiments, the first 1,4-benzoquinone is a 1,4-benzoquinone having three unsubstituted carbon atoms and a carbon atom substituted with an electron withdrawing group on the benzoquinone ring. Exemplary electron withdrawing groups include, without limitation, nitrile (cyanide), —$CF_3$, —$SF_5$, imides, imidazoles, benzimidazoles, or pyrazoles.

In some embodiments, the first, second, third and fourth mercaptoalkylsulfonates are each independently $HS(CH_2)_n SO_3^-$ or corresponding salts, esters or acids, where n is 1, 2, 3 or 4. The corresponding first, second third and fourth thioether sulfonate moieties are each independently —$S(CH_2)_n SO_3^-$ or corresponding salts, esters or acids, where n is 1, 2, 3 or 4.

In some embodiments, the first and second; first, second and third; or first, second, third and fourth mercaptoalkylsulfonates are the same. Thus, the corresponding first and second; first, second and third; or first, second, third and fourth thioether sulfonate moieties are the same.

In some embodiments, the electric current is applied to the first, second, or third hydroquinone adduct or combinations thereof through an electrolysis anode.

In some embodiments, the steps of the method are performed in an aqueous solution. In some such embodiments, the aqueous solution is acidic.

In some embodiments, the electric current is applied through the selected electrode material at a potential such that the first, second, third and/or fourth mercaptoalkylsulfonates do not readily oxidize to the corresponding disulfides.

In some embodiments, the first, second, third and/or fourth mercaptoalkylsulfonates are 2-mercaptoethanesulfonate (MESNA) or salts, esters or acids thereof; or 3-mercapto-1-propanesulfanate (MPSNA) or salts, esters or acids thereof. In some such embodiments, the first, second, third and fourth mercaptoalkylsulfonates are all MESNA or salts, esters or acids thereof; the first 1,4-benzoquinone is:

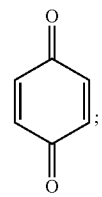

and the fourth hydroquinone adduct is:

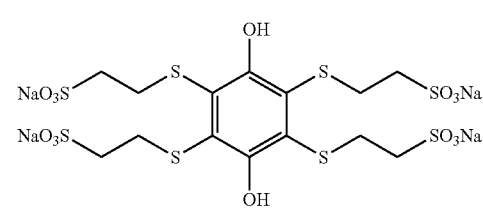

or other salts, esters or acids thereof.

In other such embodiments, the first, second, third and fourth mercaptoalkylsulfonates are all MPSNA or salts, esters or acids thereof; the first 1,4-benzoquinone is:

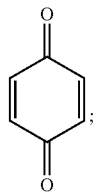

and the fourth hydroquinone adduct is:

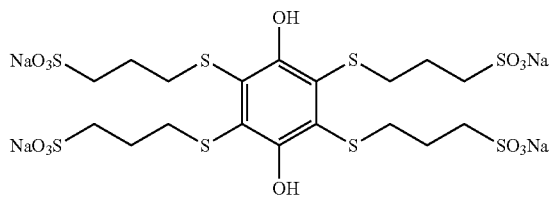

or other salts, esters or acids thereof.

The following descriptions are of certain exemplary embodiments, and should not be considered limiting. The full scope of the invention is defined by the appended claims.

DETAILED DESCRIPTION

I. In General

Figure 1:
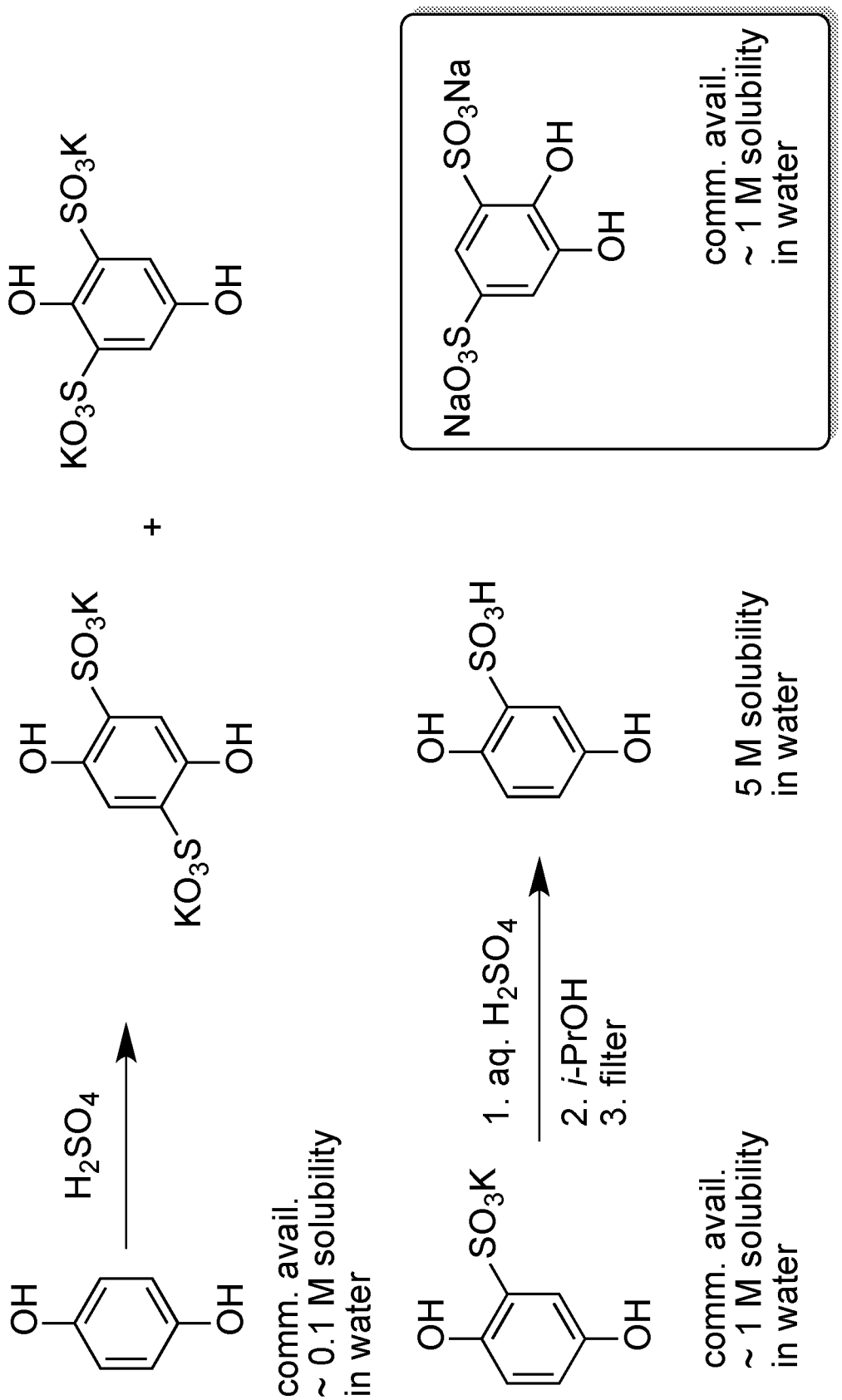
FIG. 1 illustrates a previously reported hydroquinone sulfonate synthesis, along with reported reactant, intermediate, and reactant solubilities in water.

This disclosure is not limited to the particular methodology, protocols, materials, and reagents described, as these may vary. Furthermore, the terminology used herein is for the purpose of describing particular embodiments only, and is not intended to limit the scope of the present invention which will be limited only by the pending claims.

As used herein and in the appended claims, the singular forms "a", "an", and "the" include plural reference unless the context clearly dictates otherwise. As well, the terms "a" (or "an"), "one or more" and "at least one" can be used interchangeably herein. The terms "comprising", "including", and "having" can be used interchangeably.

Unless defined otherwise, all technical and scientific terms used herein have the same meanings as commonly understood by one of ordinary skill in the art. Although any methods and materials similar or equivalent to those described herein can be used in the practice or testing of the present invention, the methods and materials of several embodiments now described. All publications and patents specifically mentioned herein are incorporated by reference in their entirety for all purposes.

II. The Invention

We have developed hydroquinones/benzoquinones that are substituted on one or more of carbons 2, 3, 5 and/or 6 of a hydroquinone/1,4-benzoquinone ring with one, two three or four thioether sulfonate groups. Unlike unsubstituted benzoquinone, these compounds are water soluble and stable in acid solution.

The term "sulfonate moiety" as used herein refers to a substituent having the general structure:

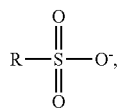

as well as the corresponding salts, acid (terminating with —OH instead of —O$^-$), and esters. R is either the hydroquinone/quinone ring (i.e., the sulfonate is directly bound to the hydroquinone or quine ring) or a linking group that links the sulfonate moiety to the hydroquinone/quine ring. In the presently disclosed exemplary embodiments and methods for making the same, R may include a thioether linking group having the general structure —S(CH$_2$)$_n$—, where n is 1, 2, 3, or 4. In the exemplary hydroquinone/benzoquinone thioether sulfonates, the thioether sulfur is attached directly to one, two, three or all four of carbons 2, 3, 5 and/or 6 of the hydroquinone/benzoquinone ring.

We have further developed a new and improved method of synthesizing such hydroquinone/benzoquinone thioether alkyl sulfonates. This method is illustrated as "method 3" in the examples below. In the method, each thioether alkyl sulfonate is installed sequentially onto the hydroquinone/benzoquinone ring, facilitated by the oxidation of the resulting substituted hydroquinone to the corresponding benzoquinone using an electric current (i.e., by electrolysis).

Each installation cycle begins by contacting a benzoquinone having an unsubstituted carbon on the benzoquinone ring with a mercaptoalkylsulfonate corresponding to the thioether sulfonate group that is to be installed, thus forming a hydroquinone adduct having the desired thioether sulfonate group installed onto the previously unsubstituted carbon. The hydroquinone adduct is then oxidized by electrolysis to convert the hydroquinone adduct to the corresponding benzoquinone. If one or more carbon atoms of the benzoquinone ring remain unsubstituted, the process may be repeated one or more times to install additional thioether sulfonate groups. In certain exemplary embodiments, the original reactant is an unsubstituted 1,4-benzoquinone, and the installation cycle is repeated four times to install four thioether sulfonate groups onto the benzoquinone ring. In some such embodiments, the final cycle may omit the electrolysis step, and the tetrasubstituted hydroquinone may be extracted as the final product, or oxidized to the corresponding benzoquinone by conventional means.

This method is an elegant, efficient and practical way to make the disclosed compounds. As each substituent is sequentially installed, the resulting compound becomes easier to oxidize, thus making subsequent installations easier to accomplish. This facilitates the desired substitution of all four available carbon atoms. Furthermore, the method works with precursors having other desired substituents, such as electron-withdrawing groups, on the benzoquinone ring, provided that such groups would not be displaced by the added mercaptoalkylsulfonate. The presence of other electron withdrawing groups may result in compounds having even greater stability.

The disclosed compounds are capable of transferring protons and/or electrons by acid/base and/or oxidation/reduction reactions, have high reduction potentials, are water soluble, and are stable under acid conditions. Accordingly, the disclosed compounds may be used as redox-active species in a variety of applications. In a non-limiting example, the disclosed compounds may be used to facilitate the reduction of oxygen in cathode half-cells, particularly in the context of emerging technologies such as in mediated fuel cells or organic mediator flow batteries.

The use of hydroquinones/quinones as redox mediators to facilitate the reduction of oxygen in mediated fuel cells is described in, e.g., U.S. Patent Publication No. 2015/0263371, which is incorporated by reference herein in its entirety.

A flow battery is a rechargeable fuel cell in which an electrolyte solution containing one or more dissolved redox-active mediators flows through the electrochemical cell. Additional electrolyte is solution is stored externally, generally in tanks, and is usually pumped through the cell (or cells) of the battery, although gravity feed systems are also known. Flow batteries can be rapidly "recharged" by replacing the electrolyte liquid, while simultaneously recovering the spent material for processing and reuse.

Further details regarding specific embodiments and syntheses thereof are provided in the following examples. These specific embodiments do not in any way limit the scope of the disclosure.

III. Examples—Methods of Synthesizing Exemplary Compounds

Figure 2A:
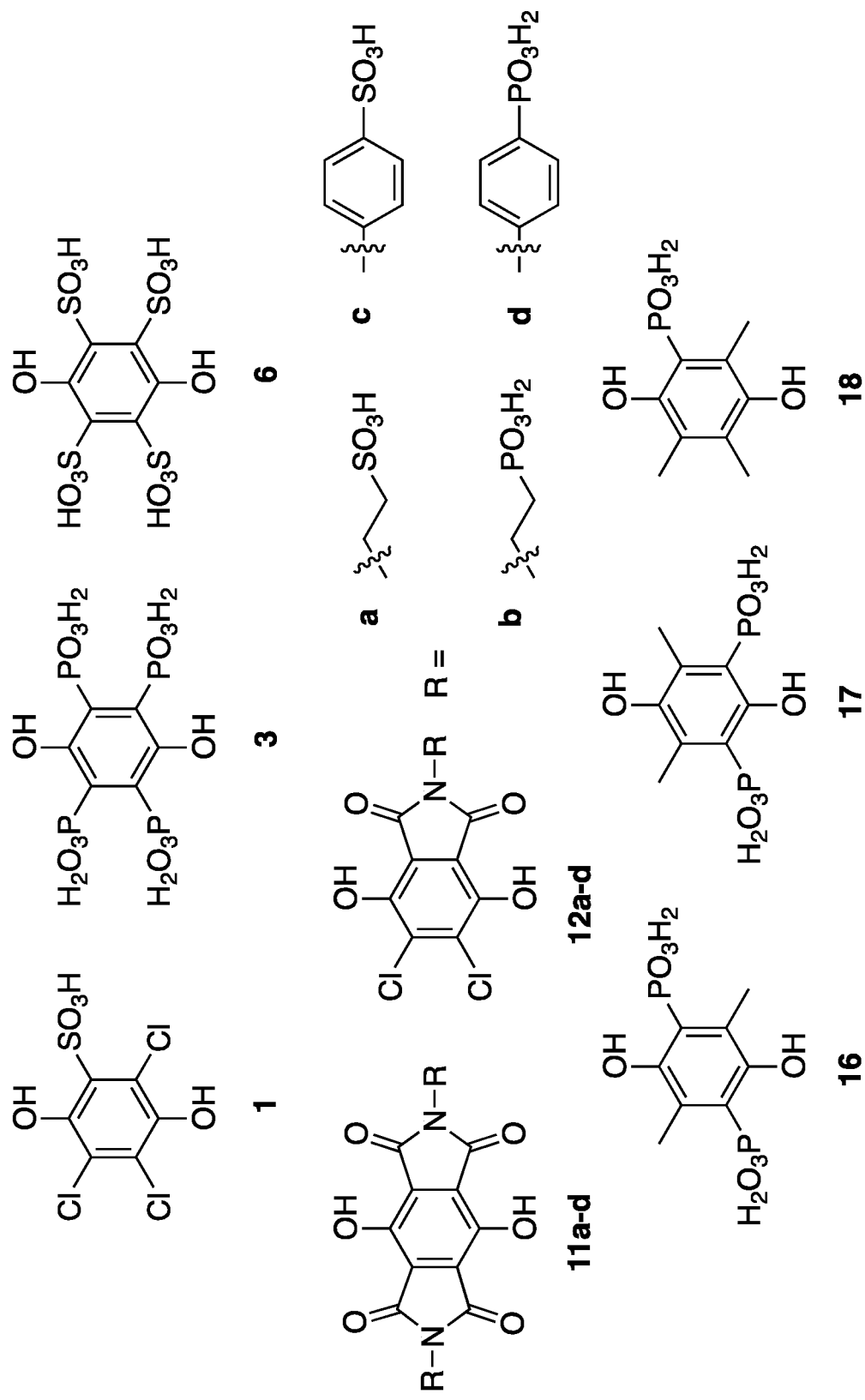
FIGS. 2A and 2B show the chemical structures of 28 exemplary substituted hydroquinones (compounds 1, 3, 6, 11a-d, 12a-d, 16-18, 21-30, 35a-d).

Example 1—Synthesis of Compound 1 of FIG. 2A

The synthesis of compound 1 of FIG. 2A as its PPh$_4$ salt in one step from p-chloranil (2) has been described (see Scheme 2 below).[7] The reported yield is low, but no attempts at optimization were reported. In our hands, the protocol in the literature is irreproducible across multiple attempts and variations of the reaction conditions.

Scheme 2: Proposed synthesis of compound 1 of FIG. 2A.

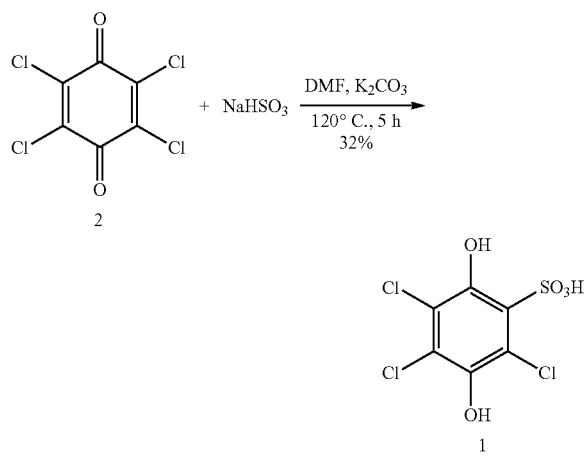

In the examples that follow, we provide schemes for synthesizing a number of other exemplary substituted hydroquinones/quinones that could be used to facilitate oxygen reduction at the cathode of an electrochemical cell. The following examples are offered for illustrative purposes only, and are not intended to limit the scope of the invention in any way. Indeed, various modifications of the disclosed method in addition to those shown and described herein will become apparent to those skilled in the art from the foregoing description and the following examples and fall within the scope of the appended claims.

Example 2—Synthesis of Compound 3 of FIG. 2A

The synthesis of compound 3 is outlined in Scheme 3 below. From p-chloranil, 2, there is a literature-precedented exhaustive phosphonation.[8,9] The resulting quinone 4 is hydrogenated to the hydroquinone 5, which was the object of the previously reported synthesis.

Scheme 3: Proposed synthesis of compound 3 of FIG. 2A.

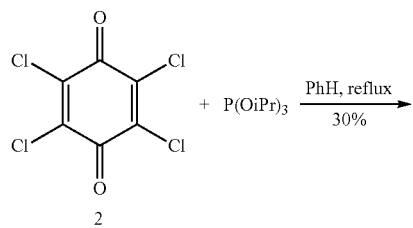

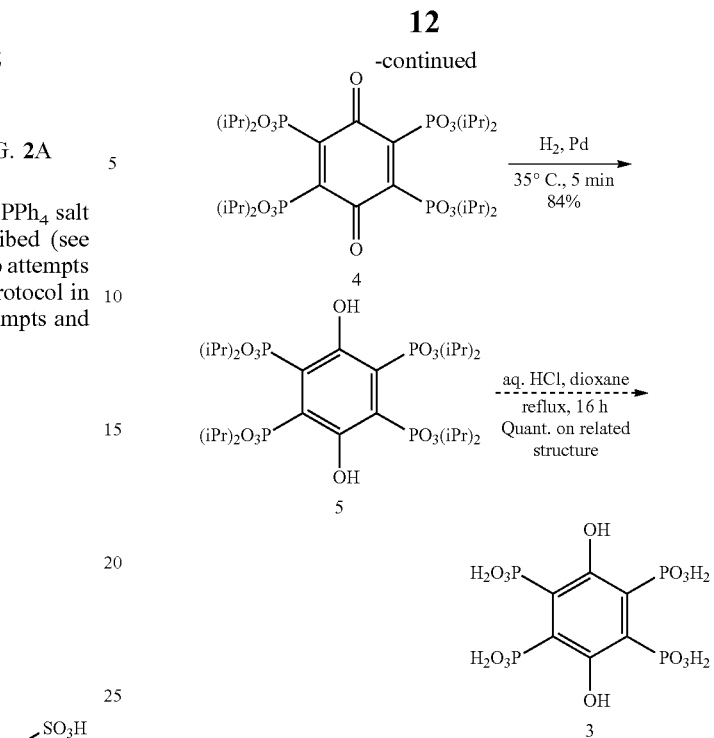

Based on the previous literature, the expected yield was 30% and the product M.P. of 154.5-155° C., its crystal structure has been reported.[8] In our hands, the yield of 4 is closer to 3.5% and the process disclosed by Reetz is irreproducible.

Out of many variations of the reaction conditions, the only method that gave isolable amounts of 4 is the following. 2.48 g of chloranil were dispersed in 10 ml of toluene and heated under nitrogen to 90° C. Over 2.25 hours, 4 ml of tri-isopropyl phosphite were added dropwise and then allowed to react for 1.25 hours at 90° C. The resulting mixture was then concentrated under vacuum at temperatures up to 80° C. The residue was dispersed in 50 ml of heptane, chilled to 0° C., filtered, and rinsed with 10 ml of heptane. The resulting solids were dissolved in 20 ml of acetonitrile, filtered, and rinsed with 5 ml of acetonitrile. The filtrate was rotovapped to give an orange solid. This solid was crystallized from 5 ml of ethyl acetate and filtered to remove unreacted chloranil which was rinsed with 2 ml of ethyl acetate. The combined filtrates were mixed with 7 ml of heptane and concentrated by heating. On cooling, 0.267 g of an orange solid formed with a sharp melting point of 150° C. with an additional 35 mg being obtained from the filtrate. Efforts to improve this yield by varying the reaction conditions are in progress.

Hydrogenation of 4 has been claimed to give 5 in high yield.[8] Take 11.46 g (15 mmol) of 13 dissolved in 33 ml ethanol. Place the solution with a Pd/C catalyst in a hydrogen-purged hydrogenation apparatus. The hydrogenator is then placed under 60 psi of hydrogen for a period of two hours at 35-40° C. The hydrogen gas is then released and the reaction mixture filtered to remove the palladium. Water is added to the remaining alcoholic solution causing fluorescent pale green crystals to precipitate. These crystals are then further recrystallized from an ethanol/water solution to give p-hydroquinone tetrakis (di-isopropyl phosphonate), 5. Expected yield: 84%.

Either 4 or 5 should be able to be hydrolyzed to 3 as shown in Scheme 3. Hydrolysis of diphosphonic esters has been the subject of considerable previous research towards various pharmaceuticals, and the mild protocols devised there should be effective in yielding the tetraphosphonic acid if the method shown is too harsh.[10]

Example 3—Synthesis of Compound 6 of FIG. 2A

Synthesis of compound 6 is unprecedented, however the even more sterically-congested benzenehexasulfonic acid has been reported.[11] Applying similar copper-catalyzed conditions to 1,4-diacetoxytetrachlorobenzene or tetrachlorohydroquinone with other protecting groups appended may result in a similarly profound dechlorosulfonation (Scheme 4)[12] Deprotection of the hydroquinone should be facile. Preliminary experiments using chloranil directly have been performed and suggest that CuCl may be a better catalyst precursor.

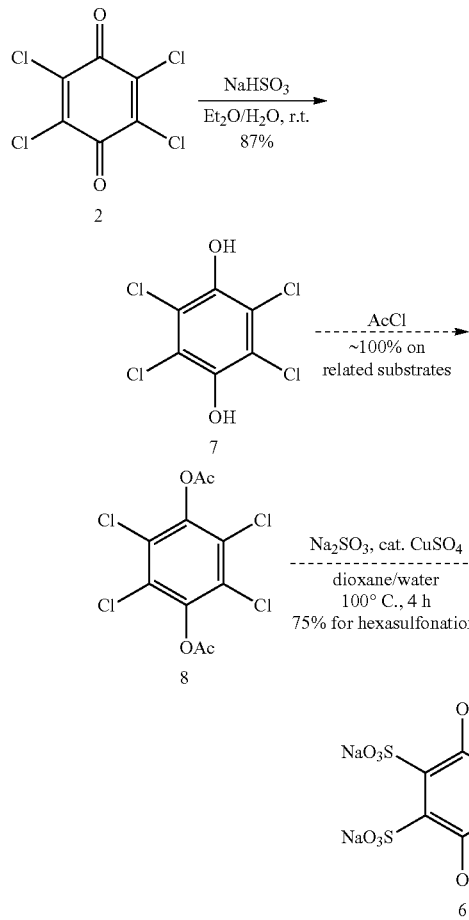

Scheme 4: Proposed synthesis of compound 6 of FIG. 2A.

An alternative route involves the reaction of chloranil with thioglycolic acid to form the tetrathia-substituted hydroquinone 9 (reduction happens in-situ, see Scheme 5).[13] Other aryl thioglycolates have been oxidized to the corresponding sulfonic acids by refluxing nitric acid.[14] We prophesize that treatment of 9 with refluxing nitric acid will produce compound 10 (the oxidized version of 6) by a similar reaction.

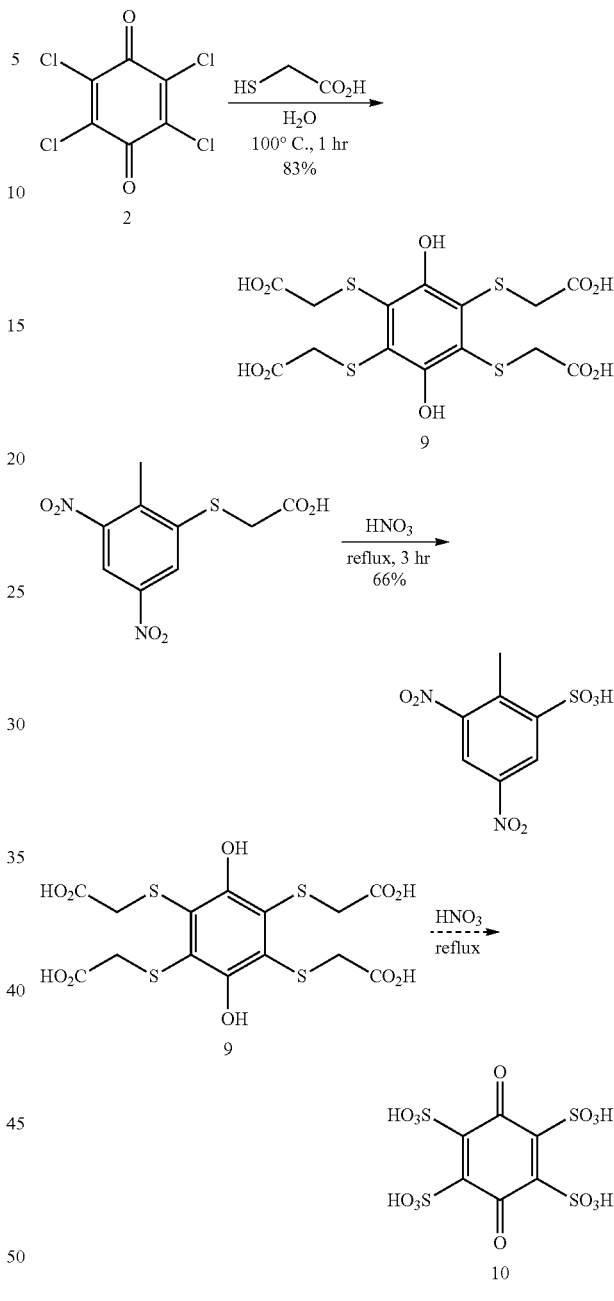

Scheme 5: Proposed synthesis of compound 10 of FIG. 2 via thiol adduct 9.

Example 4—Synthesis of Compounds 11a-d and 12a-d of FIG. 2A

Solubilized Dihydroxypyromellitimide and Dichlorophthalimide Mediators.

There are routes to dihydroxypyromellitimides described in the polymer literature as model compounds.[15] The synthesis of dichlorodihydroxyphthalimide is also precedented.[16] These reactions could be adapted to incorporate substituents with solubilizing groups to yield the heretofore-unknown hydroquinones 11a-d and 12a-d illustrated in FIG. 2A.

Compound 11a-d Synthesis.

The synthesis of compounds 11a-d proceed from dihydroxypyromellitic anhydride 13, which can be accessed via a number of routes.[17] One such route is shown in Scheme 6, where the final product was an analogue of 11 where R=4-butylphenyl.[18,19] A similar condensation of this anhydride with a salt of taurine or 2-aminoethylphosphonic acid should give the desired compounds 11a and 11b.[20] Condensation with 4-aminophenylsulfonic acid or 4-aminophenylphosphonic acid should give 11c and 11d respectively. An alternative route would produce the quinone form, 14a-d, starting from durene.[21,22,23,24]

Scheme 6: Proposed syntheses of compounds 11a-d and 14a-d of FIG. 2A.

Route 1:

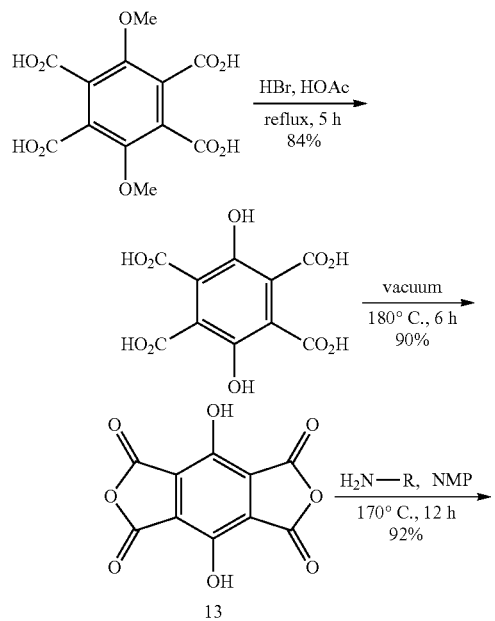

Route 2:

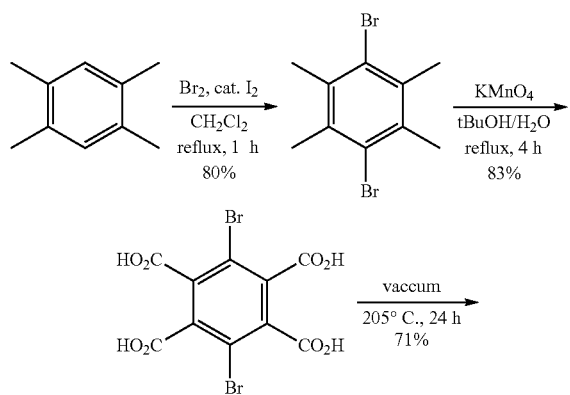

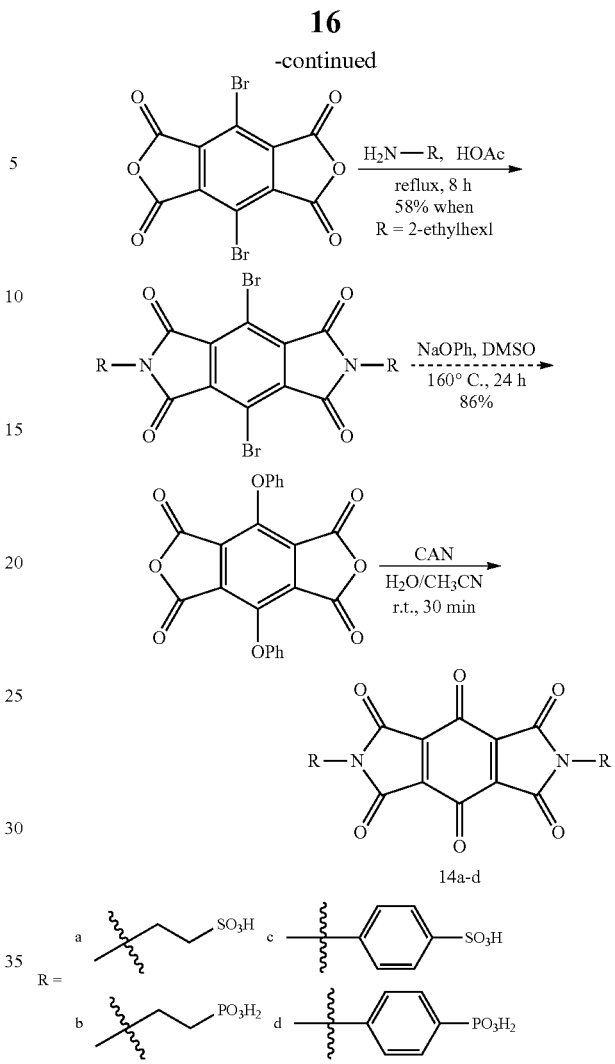

Compound 12a-d Synthesis

The synthesis of compounds 12a and 12b begins from the reduced form of DDQ. Analogous substituted phthalimides have also been made from 2,3-dicyanohydroquinone and dibromodicyanohydroquinone.[25] A similar treatment of tetracyano hydroquinone could be an alternative route to 11a-d. Gabriel reaction of 15 or its di-acetate (also reported in Ref 21) with 2-chloroethylsulfonate or 2-chloroethylphosphonate should then yield 15a and 15b respectively. Synthesis of 15c and 15d would require first forming the anhydride in an analogous pathway to synthesis of 11, or a catalyzed amination of the appropriate arene acid.

Scheme 7: Proposed synthesis of compound 12 of FIG. 2A.

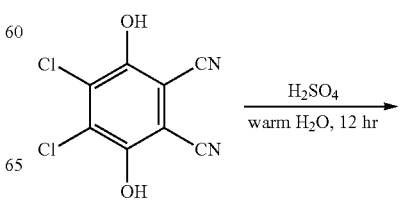

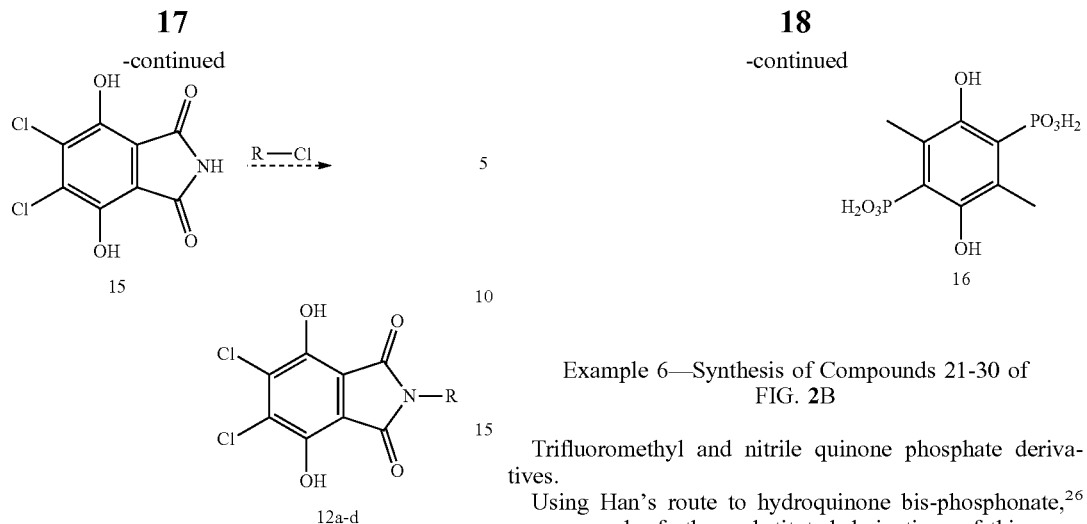

Example 5—Synthesis of Compounds 16-18 of FIG. 2A

Ring-methylated hydroquinone phosphonic acids.

The proposed synthesis of compounds 16-18 of FIG. 2A relies on insight into clues hidden in the literature.[26] In DMSO, diethyl phosphite will add to benzoquinone twice to produce hydroquinone bis-phosphonate and hydroquinone in equal amounts. These authors also demonstrated efficient mono-phosphonation of 2,5-dialkyl-quinones in wet toluene under otherwise similar conditions. While trimethylquinone was not tried as a substrate by Han and co-workers, our experiments have shown that it yields an ester of 18 and that it is necessary to let the reaction run for a longer time than previously reported. Combining the conditions of the first set of experiments with the substrates of the second set of conditions should yield di-alkylhydroquinone-diphosphonate esters. Our preliminary experiments towards synthesis of 16 and 17 suggest that the reaction conditions will need to be re-optimized in ways that were not initially obvious. Hydrolysis of the esters should then give 16-18.

Compound 16 Synthesis.

Our experiments have shown that starting material 19 is recovered unchanged after 18 hours under the conditions shown in Scheme 8. However, variations on these conditions are expected to lead to a reaction.

Scheme 8: Proposed synthesis of compound 16 of FIG. 2A.

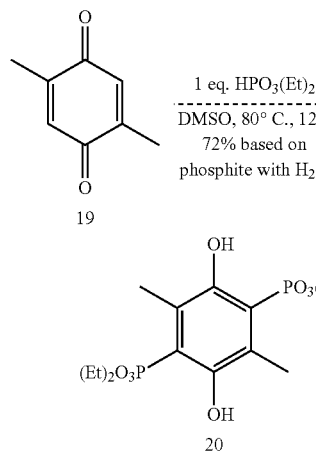

Figure 2B:
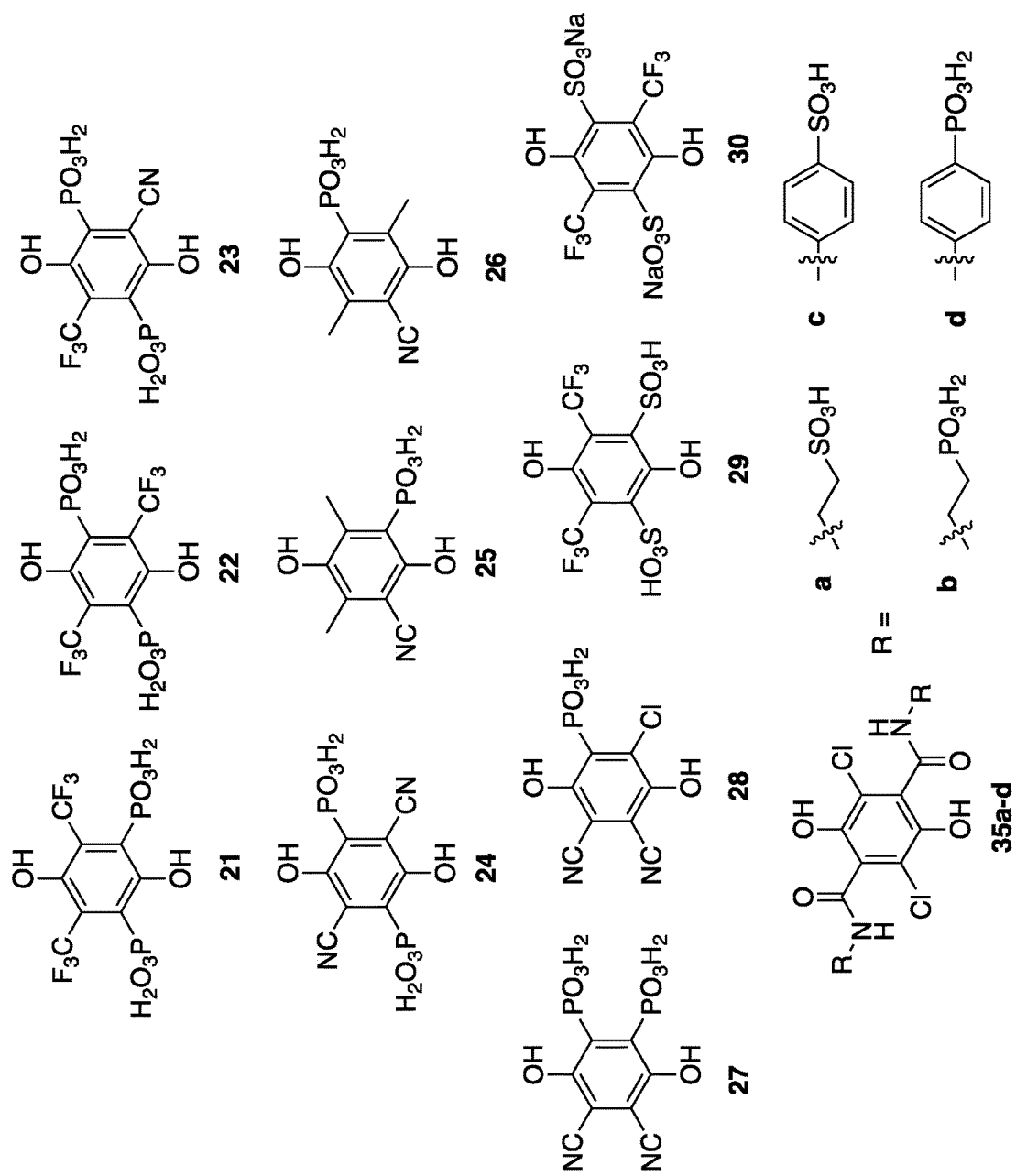

Example 6—Synthesis of Compounds 21-30 of FIG. 2B

Trifluoromethyl and nitrile quinone phosphate derivatives.

Using Han's route to hydroquinone bis-phosphonate,[26] one can make further substituted derivatives of this compound. For instance, exhaustive free-radical trifluoromethylation of the different isomers would yield esters of 21 and 22 (FIG. 2B).[27] Alternatively, one could start from the appropriate trifluoromethylated quinones and phosphonate them.

Trifluoromethylation of methyl-protected bis-iodo hydroquinones is an established reaction,[28] and benzyl protected structures would presumably react similarly (Scheme 9). Starting from an isomeric aryl iodide will place the trifluoromethyl groups in the correct position to eventually yield compound 21 instead of 22.

Scheme 9: Proposed synthesis of compound 22 of FIG. 2B.

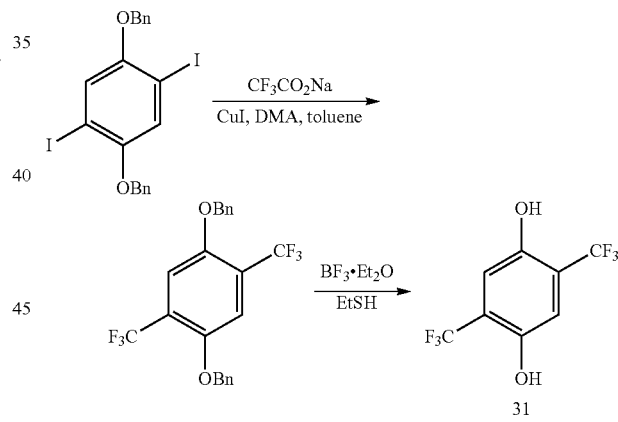

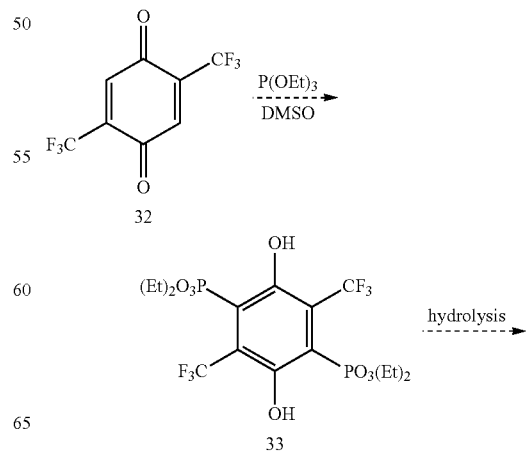

19

-continued

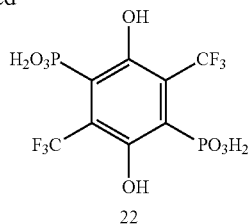

22

Cyano- and Chloro-Cyano-Hydroquinone Phosphonates.

Cyanide ion or HCN readily adds to many quinones as proposed in Scheme 10. Mono-trifluoromethylation of 2,5-bisphosphonate ester-hydroquinone, addition of cyanide, and hydrolysis would give 23 (FIG. 2B). Similar oxidation/cyanation reactions of the appropriate phosphonates would yield esters of 24-26 (FIG. 2B).

Scheme 10. Addition of cyanide to form structure 23 in FIG. 2B.

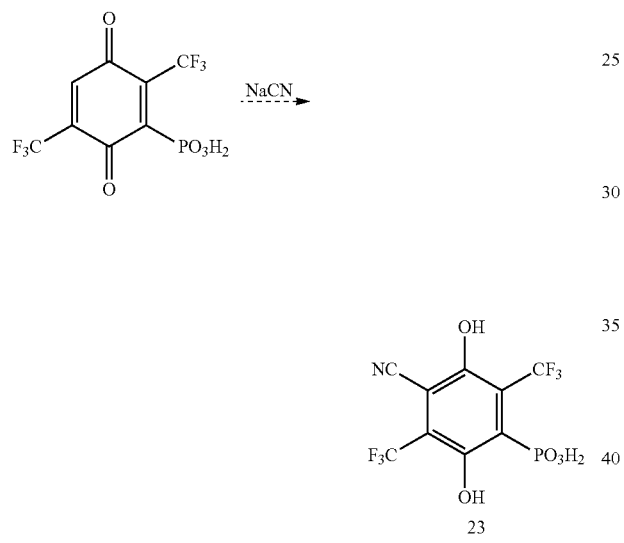

23

In 1998, Abdou and co-workers described a method to react 2,3-dichloro-5,6-dicyanoquinone (DDQ) with tri-isopropyl phosphite to yield the di-isopropyl ester of 28 (FIG. 2).[29] By using a different stoichiometry and other conditions, esters of 27 (FIG. 2B) should also be achievable.

Trifluoromethylated Hydroquinone Disulfonates.

If the trifluoromethylation methods used for the synthesis of compounds 21 and 22 (FIG. 2B) are employed on hydroquinone disulfonates, 29 and 30 (FIG. 2B) are the expected products.

Example 7—Synthesis of Compounds 35a-d of FIG. 2B

A densely functionalized quinone, 34, has been prepared in only two steps from diethyl succinate.[30,31,32] Scheme 11 shows how this could produce the desired compounds 35a-d (FIG. 2B). If the cyanide-catalyzed aminolysis to install polar functionality is unsuccessful, more conventional hydrolysis/coupling sequences could be used on the hydroquinone diester.[33,34]

20

Scheme 11: Proposed synthesis of compounds 35a-d of FIG. 2B.

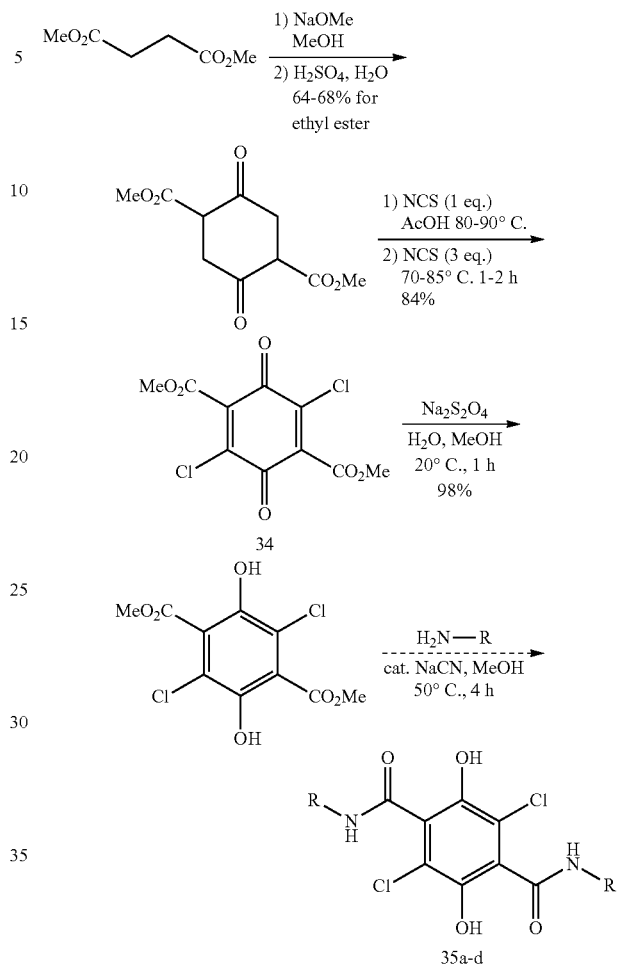

35a-d

Figure 3A:
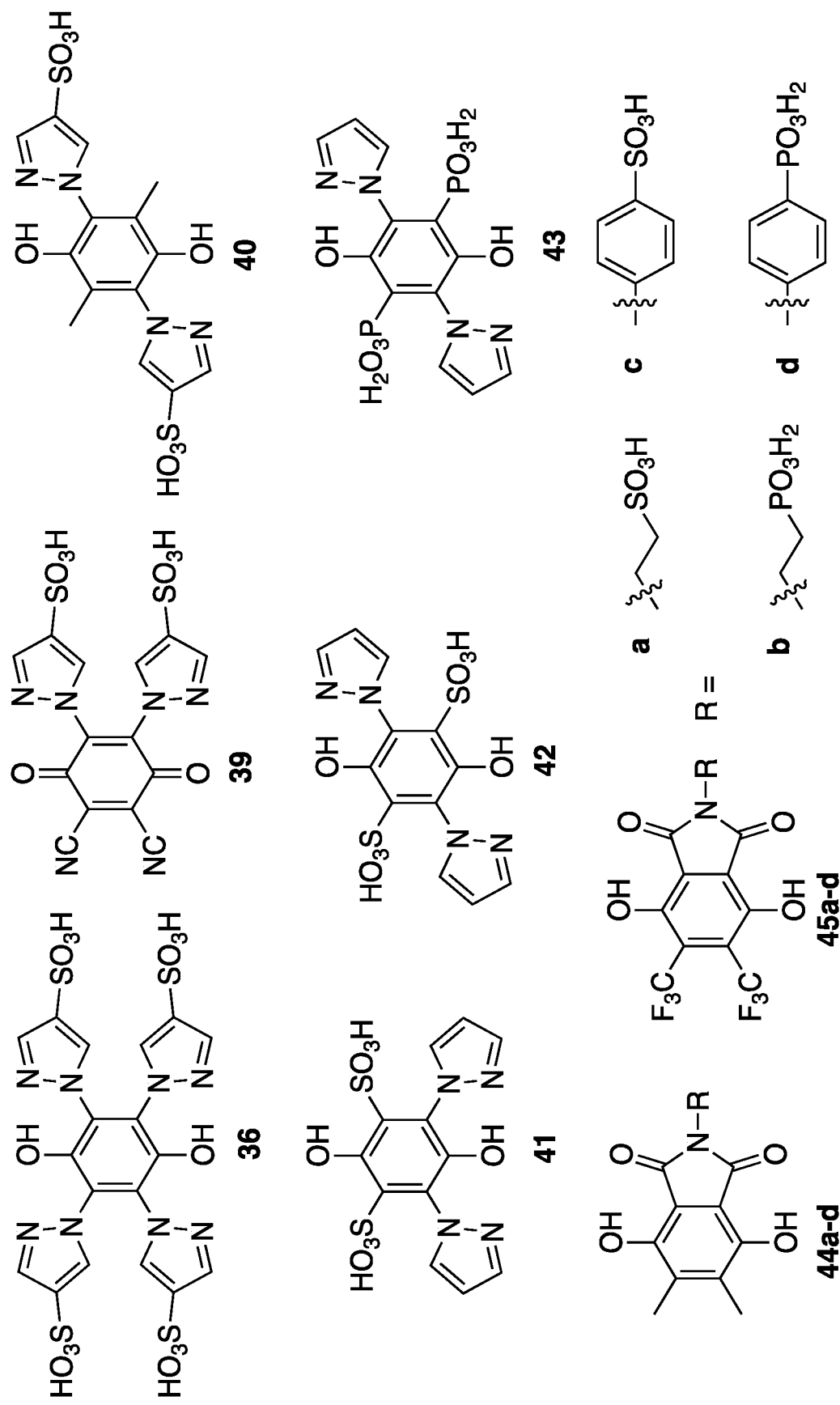
FIGS. 3A and 3B show the chemical structure of an additional 21 exemplary substituted hydroquinones and quinones (compounds 36, 39-43, 44a-d, 45a-d, 46-47, 48a-d, 49).

Example 8—Synthesis of Compound 36 of FIG. 3A and Related Pyrazole-Containing Compounds Pyrazole- and Pyrazolesulfonate-Substituted Hydroquinones.

In this example, we disclose the synthesis of compound 36 and related compounds, which are labeled as compounds 38-40 in Scheme 12 below. Compound 38 is the oxidized version of 36.

Compounds 38-40 of Scheme 12 share a common reagent and synthesis, differing in the substrate to which it is employed. Pyrazoles with various substituents (4-Cl, 4-NO$_2$, 3,5-dimethyl, etc.) have been shown to add to quinones to give pyrazole-substituted hydroquinones.[35,36,37] This reaction has been demonstrated with chloranil and pyrazole itself to give the tetrasubstituted quinone product.[36] Pyrazole has been sulfonated at its 4-position to give pyrazole-4-sulfonic acid, 37.[37] In combination, these reactions should give 38-40 as shown in Scheme 12.

Comparisons of literature procedures suggests that compound 36 could also be accessed by sulfonation of the unsulfonated precursor. Analogues of 36 or 38 with one to three sulfonate groups appended may also be of interest if they are formed.

Scheme 12: Observations from the literature and proposed synthesis of compounds 38-40.
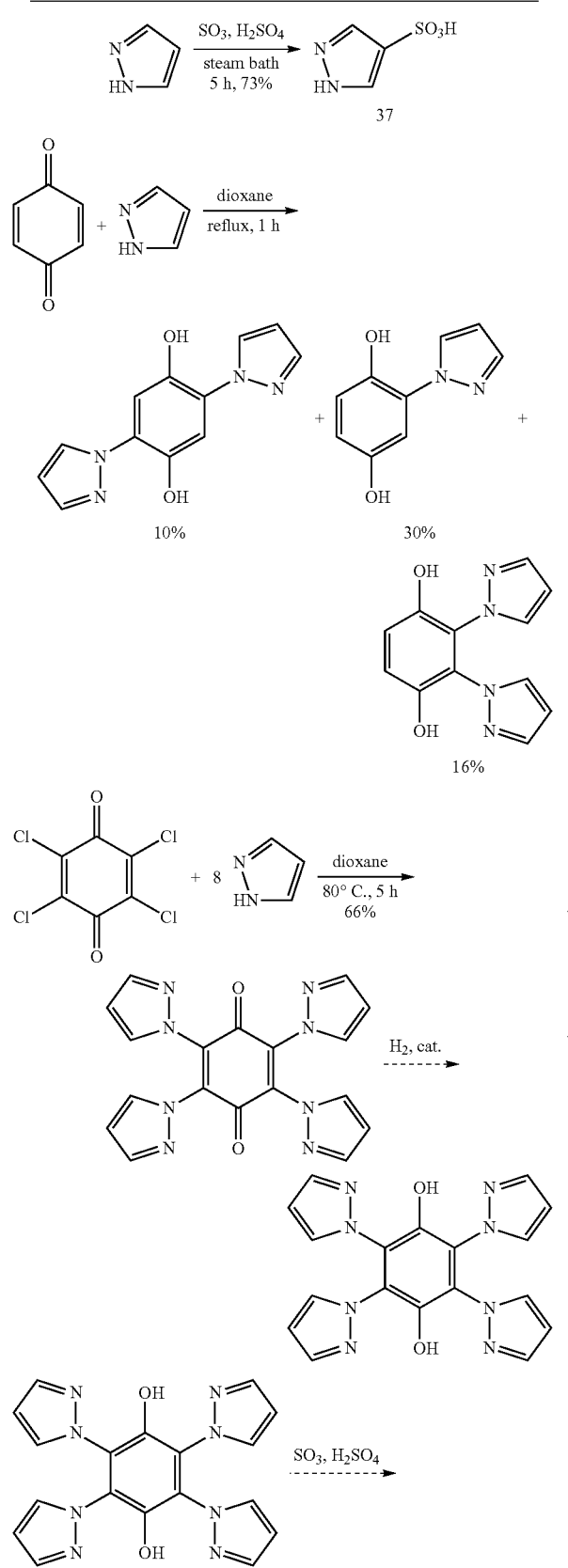
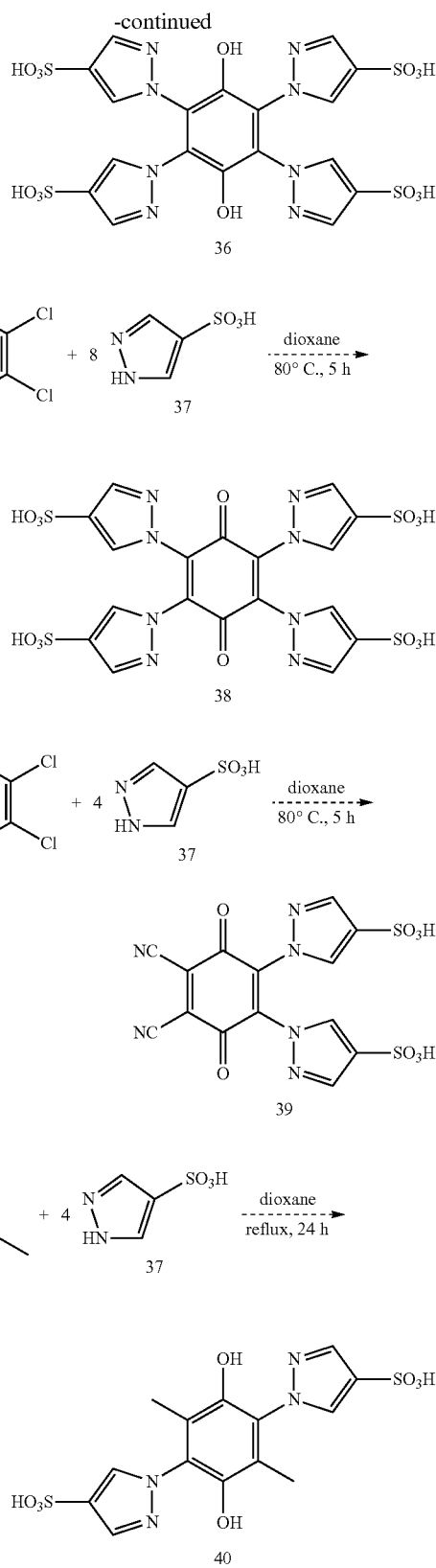
Following similar procedures, pyrazoles could be installed on quinones containing phosphonates or sulfonates, reduction of which would result in structures 41-43 in FIG. 3A.

Example 9—Synthesis of Compounds 44a-d and 45a-d of FIG. 3A 4,5-Disubstituted Dihydroxyphthalimides (Scheme 13).

The bis-silyl enolate of succinic anhydride is capable of performing as a diene in Diels-Alder reactions, including with N-substituted maleimides to give 3,6-dihydroxyphthalimides.[38] With appropriately substituted succinic anhydrides and maleimides, this reaction would yield compounds 44a-d and 45a-d (FIG. 3A).

Scheme 13: Observations from the literature and proposed synthesis of compounds 44a-d and 45a-d.

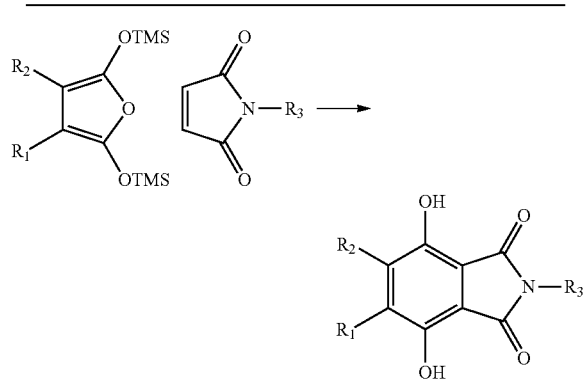

Figure 3B:
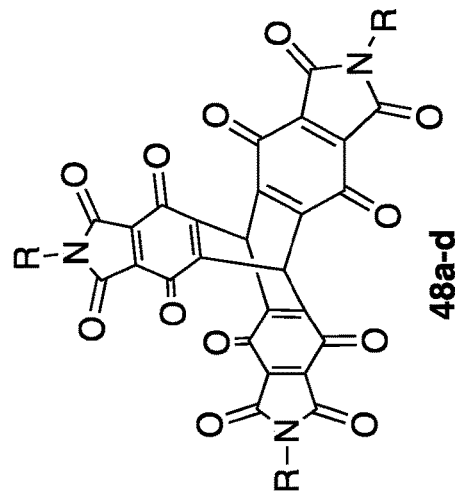
Figure 3B:
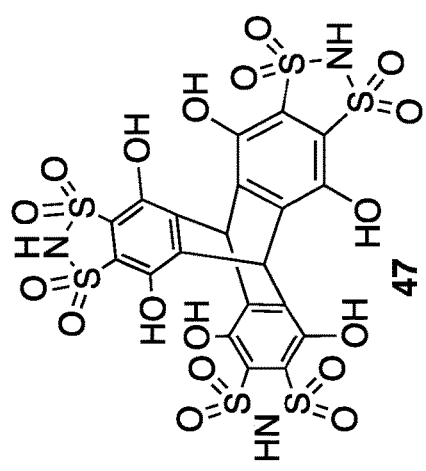
Figure 3B:
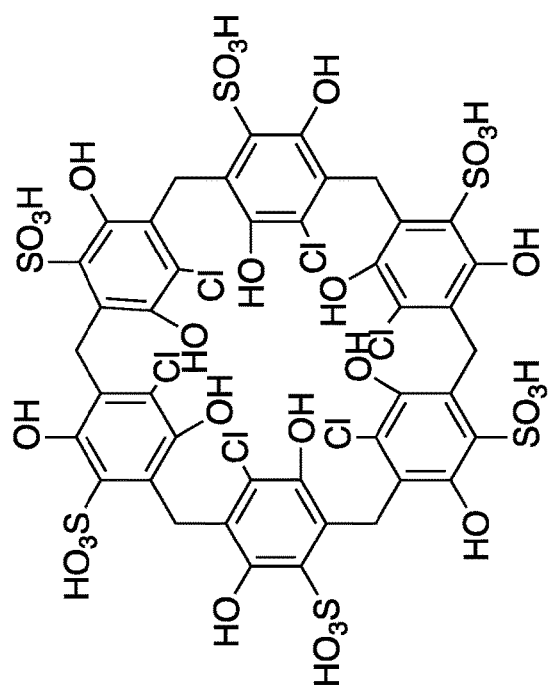
Figure 3B:
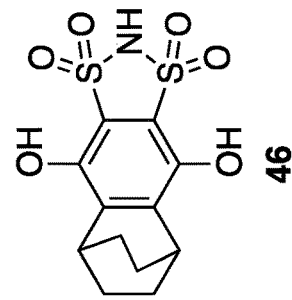

Example 10—Synthesis of Compound 46 of FIG. 3B

Bicyclic Hydroquinone (Scheme 14).

An analogue to the carboximide group is the bis-sulfonimide group.[39] In addition to being more resistant to hydrolysis, the more electron-withdrawing sulfonyl groups make the N—H bond more acidic. As an example, benzene-1,2-bis-sulfonimide is as acidic as HCl. Thus, quinones substituted with this group should be water-soluble anions. Quinones can also act as Diels-Alder dienophiles, such as cyclohexadiene, and produce tricyclic products. Through formation of a bis-sulfonylimine quinone and its reaction with cyclohexadiene and subsequent reduction, compound 46 could be produced (FIG. 3B). This Diels-Alder/reduction sequence could also be used to produce tricyclic analogues of 44a-d (FIG. 3A).

Scheme 14: Observations from the literature and proposed synthesis of compound 46.

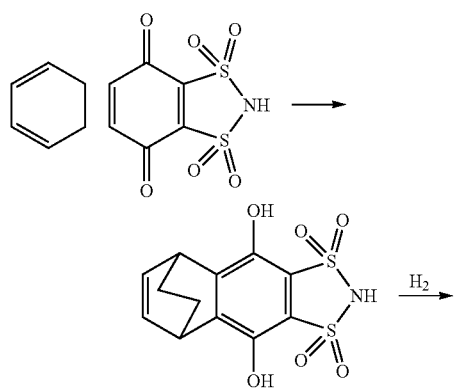

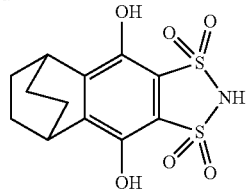

Example 11—Synthesis of Compounds 47, 48a-d, 49 of FIG. 3B

Triptycene-Triquinone and Pillar[6]Arene Quinone Mediators.

If a substituted anthracene is used as the diene in a Diels-Alder reaction with a quinone, a triptycene results.[40] Use of this reaction with appropriately-functionalized reactants would result in 47, 48a-d, or analogues thereof (FIG. 3B). It is advantageous to have a redox mediator that delivers multiple electrons, since this will lead to higher currents, other things being equal. These species, having three quinone moieties per molecule would act as six-electron oxidants or reductants.

A further increase in the number of quinone units is possible in pillar[n]arene macrocycles such as 49 (FIG. 3B). A dibromo analogue of 49 has been previously synthesized,[41] and could serve as a starting point for derivatization of the molecule.

Figure 4A:
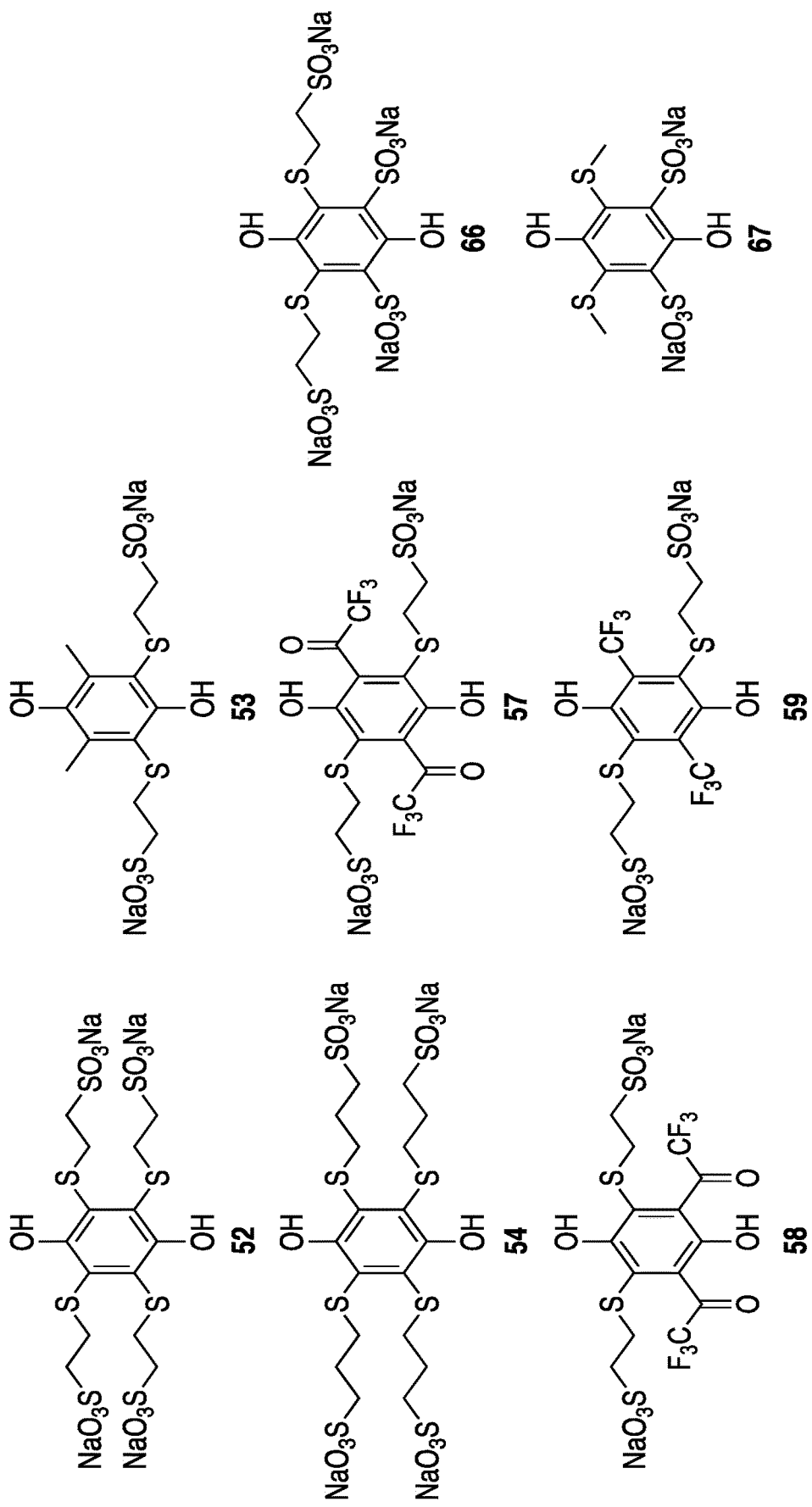
FIGS. 4A and 4B show the chemical structure of an additional 17 exemplary substituted hydroquinones and quinones containing thioether-linked sulfonates (compounds 52-54, 57-70).
Figure 4B:
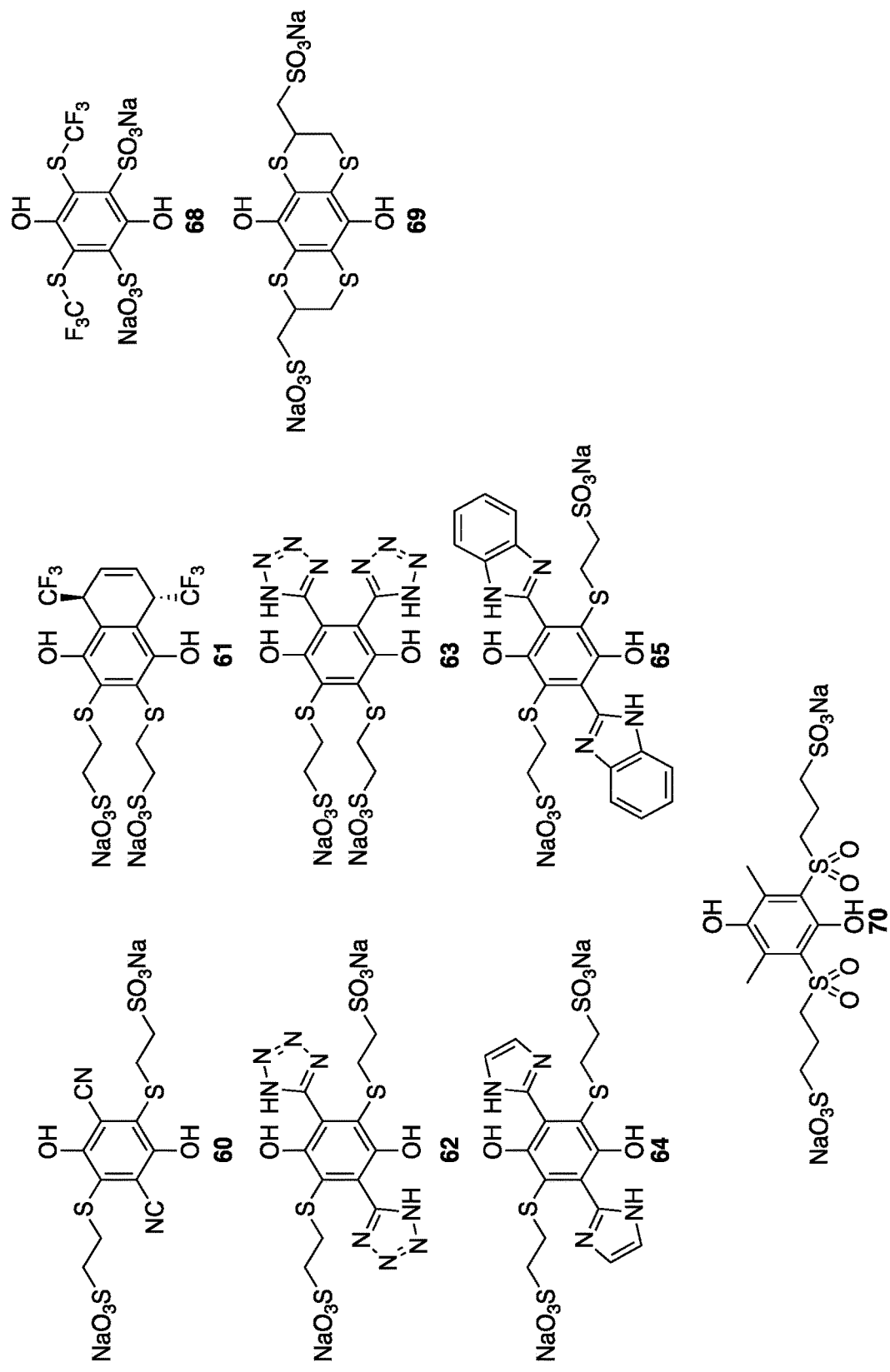

Example 12—Synthesis of Quinones with Thioether-Linked Sulfonates and Derivatives from FIGS. 4A and 4B Thiols will readily add to quinones. The resulting thioether linkage can be used to tether a solubilizing group, such as a sulfonate. Some examples of quinones containing thioether-linked sulfonates are given in FIG. 4 and discussed here. Reaction of 2-mercaptoethanesulfonate with chloranil (2) results in the substitution of chlorine by sulfur to eventually give the desired fully-substituted product, 50, in a mixture with a disulfide-linked byproduct, 51. In contrast, dichlorodicyanoquinone gives the disulfide exclusively (Scheme 15).

Scheme 15. Observations from treating Cl-containing quinones with mercaptoethanesulfonate.

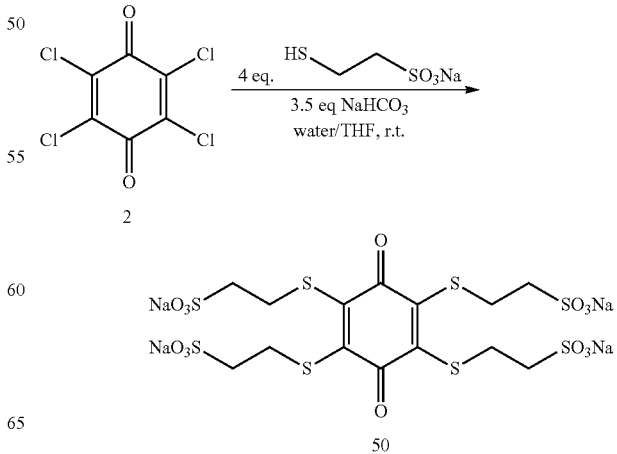

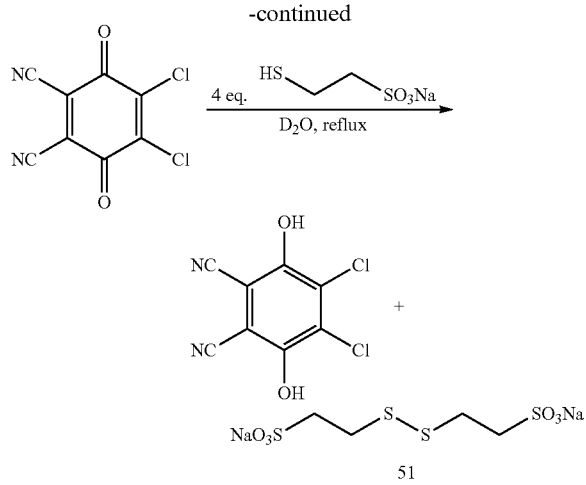

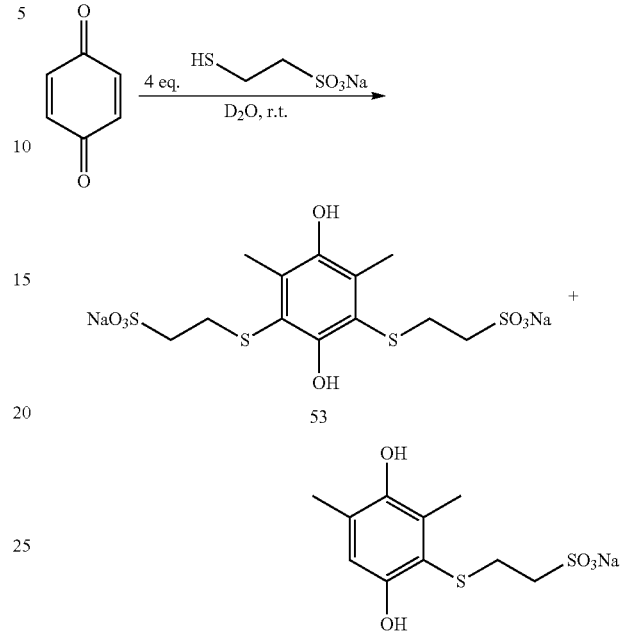

Scheme 17. Addition of mercaptoethanesulfonate to 2,6-dimethylbenzoquinone to form 53.

Figure 5A:
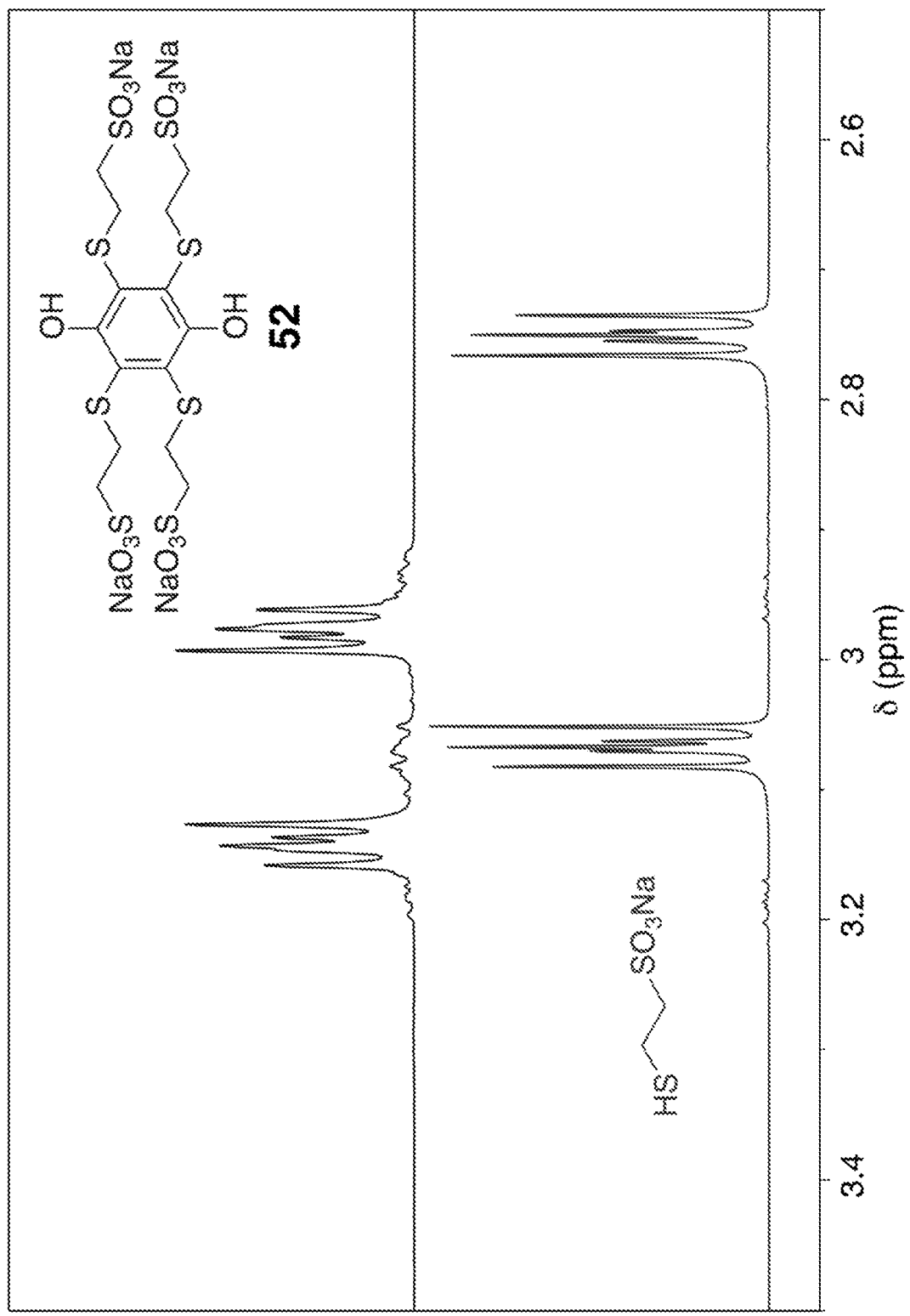
FIGS. 5A and 5B show the aliphatic region of the $^1$H and the full $^{13}$C NMR of compound 52 and MESNA, mercaptoethanesulfonate, Na salt.
Figure 5B:
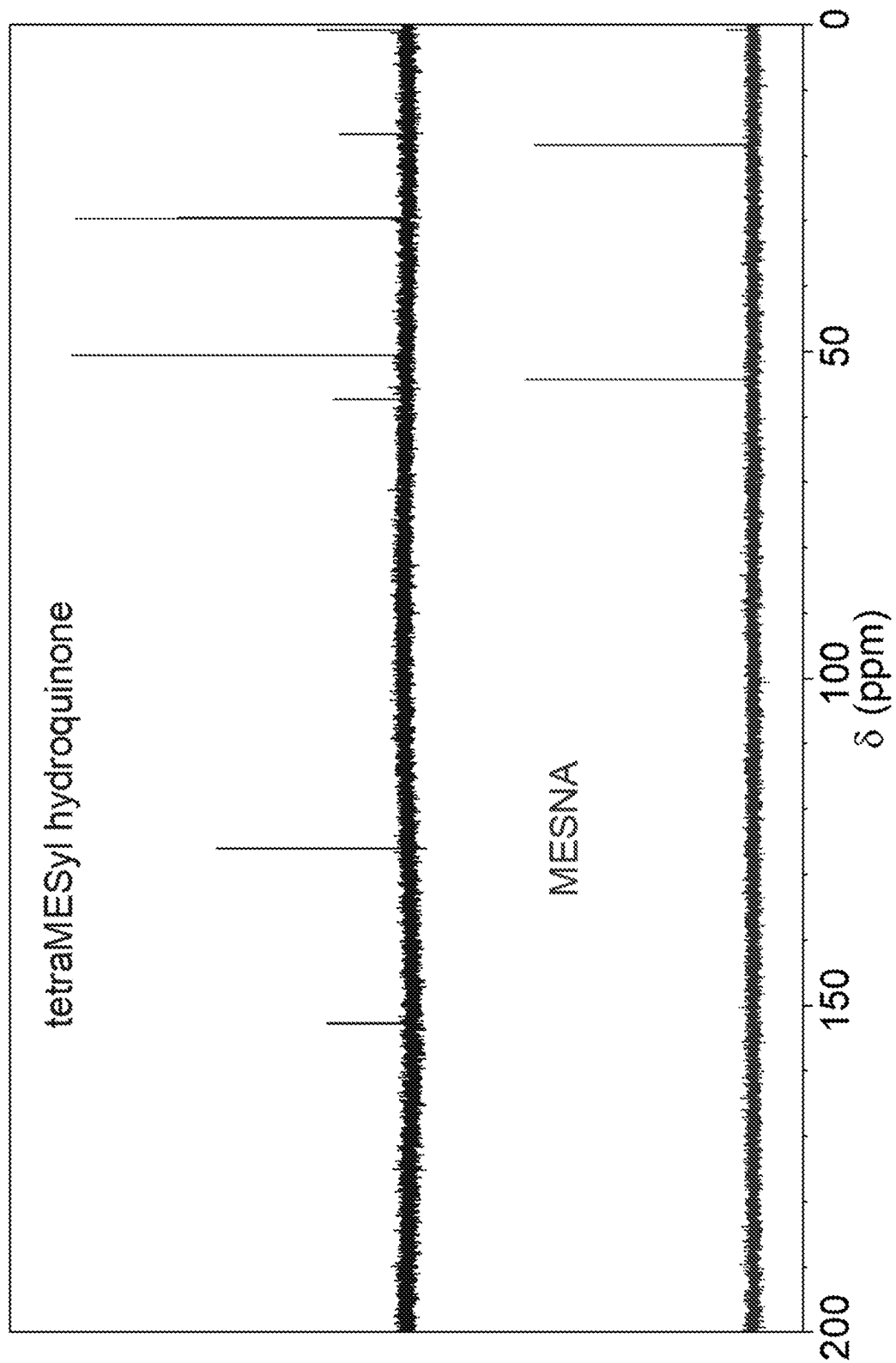

More preferably, a solution of mercaptoethanesulfonate is allowed to react with a suspension of benzoquinone in water (Scheme 16). 0.655 g of sodium mercaptoethanesulfonate in 10 ml of water with 60 microliters of acetic acid was treated with 0.438 g of benzoquinone and allowed to stir at room temperature for 45 minutes. The resulting mixture was filtered and the filtrate was extracted with three 5 ml portions of ethyl acetate. The aqueous phase was then diluted with 30 ml of ethanol and heated to clarify it. On cooling, crystals formed that gave $^1$H and $^{13}$C NMR spectra in $D_2O$ in accord with tetra-thioethylsulfonato hydroquinone, 52 (FIGS. 5A and 5B). This hydroquinone shows a reversible redox couple in aqueous 1 M $H_2SO_4$ of 0.63 V vs. NHE. Experiments suggest that slow addition of the thiol to portions of the quinone will improve the yield of the desired product.

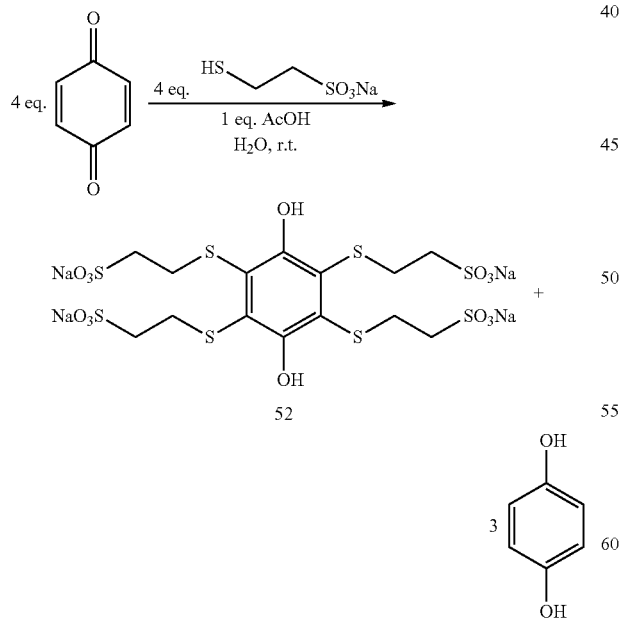

Experiments similar to those discussed above also show that 2,6-dimethylbenzoquinone will react to give a tetrasubstituted product, 53 (Scheme 17).

This method is not unique to mercaptoethanesulfonate, having been adapted from procedures used with 3-mercaptopropionate and other thiols. For example, structure 54 in FIG. 4A can be produced.

The inclusion of electron-withdrawing trifluoromethyl acetyl (—C(O)CF$_3$) substituents on a hydroquinone containing thioether-linked sulfonates is shown in Scheme 18. Synthesis of starting material 55 and 56 has been reported by Sevenard et. al.[42] Introduction of mercaptoalkylsulfonates in a similar manner as discussed above should give the products 57 and 58.

Scheme 18. Literature synthesis and proposed thioalkyl-linked sulfonation of trifluoromethylacetyl-containing quinones.

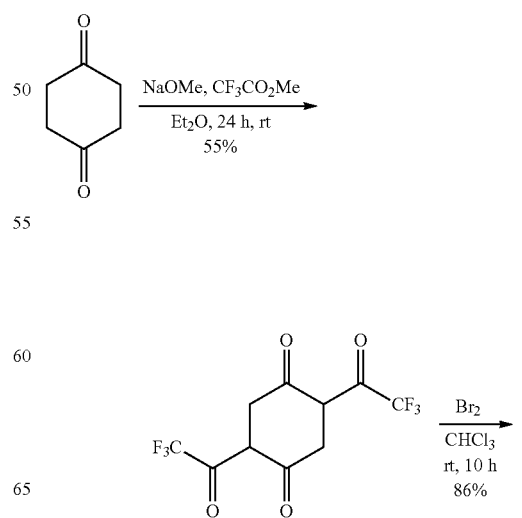

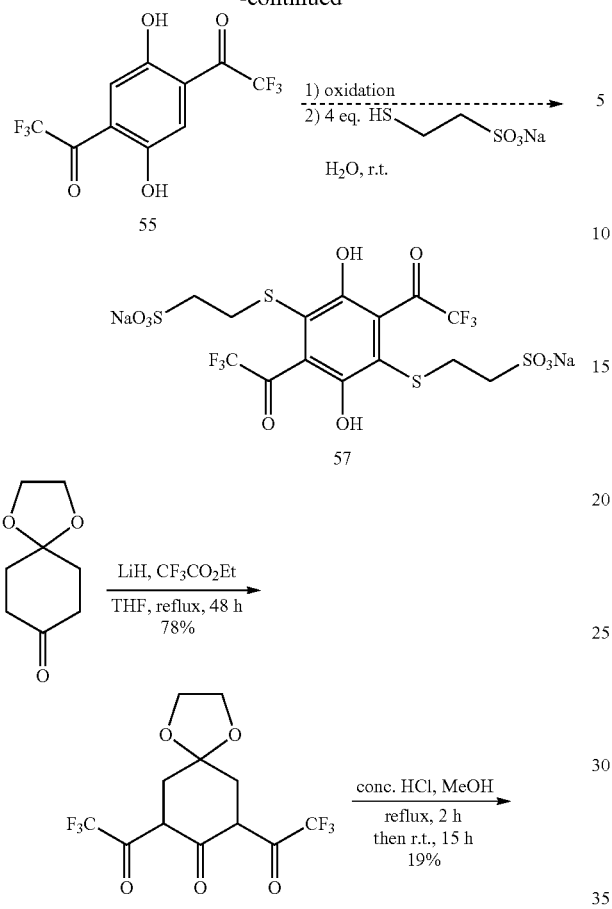

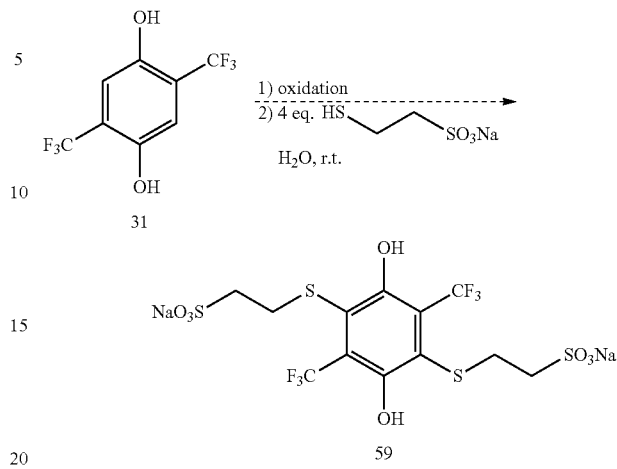

Scheme 19. Proposed synthesis of structure 59 in FIG. 4A.

We prophesize that diverse thiols with and without anionic functional groups can be appended to quinones to produce tetrasubstituted quinones in a similar process, including illustrative examples 60-69 in FIGS. 4A and 4B.

Thioethers can be readily oxidized by many methods to sulfoxides and sulfones.[43] Using one of these techniques on a thioether-quinone such as one of the ones shown above will produce a sulfoxide-quinone or sulfone-quinone. These quinones will have higher reduction potentials than the parent thioether and may have other properties that further enhance their usefulness. An alternative route to synthesize sulfone-quinones that may be preferred in some cases would be the reaction of chloranil, benzoquinone, or another quinone with the salt of appropriate sulfinic acid to form the desired sulfone such as structure 70 shown in Scheme 20.

Scheme 20. Proposed synthesis of 70 in FIG. 4B.

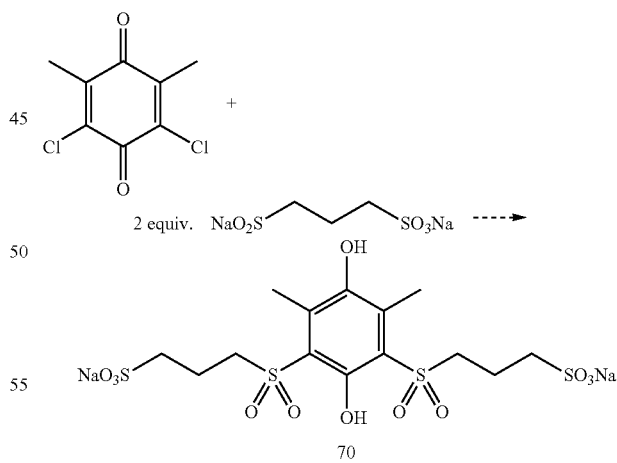

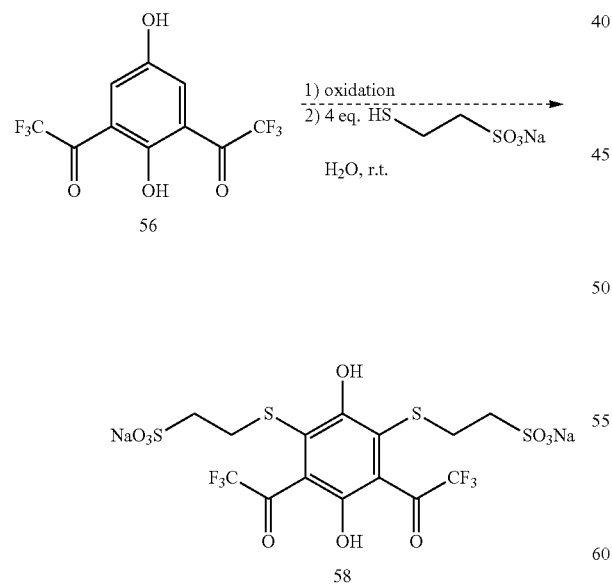

Thiother-linked sulfonates can also be installed on the bis-CF$_3$ hydroquinone 31. Adaption of the mercaptoalkyl-sulfonate installation procedure used to synthesize 141 should give 59 in Scheme 19.

Example 13—Synthesis of Quinones with Imide-Linked Sulfonates and Phosphonates

The reaction of chloranil, 2, and potassium phthalimidate gives a tetra-imido quinone 71 with relatively robust C—N bonds from the central ring that resist displacement by such strong nucleophiles as hydrazine, shown in Scheme 21.[44]

The positioning of the imide rings perpendicular to the quinone ring may protect the quinone from attack. By using imides with pendant phosphonate or sulfonate groups, the imide becomes a linking group to attach the anionic group while simultaneously protecting the quinone from further attack. Use of sulfophthalimide 72 instead of the parent phthalimide should produce structure 73 (Scheme 21) from FIG. 6A.

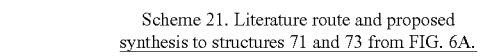

Scheme 21. Literature route and proposed synthesis to structures 71 and 73 from FIG. 6A.

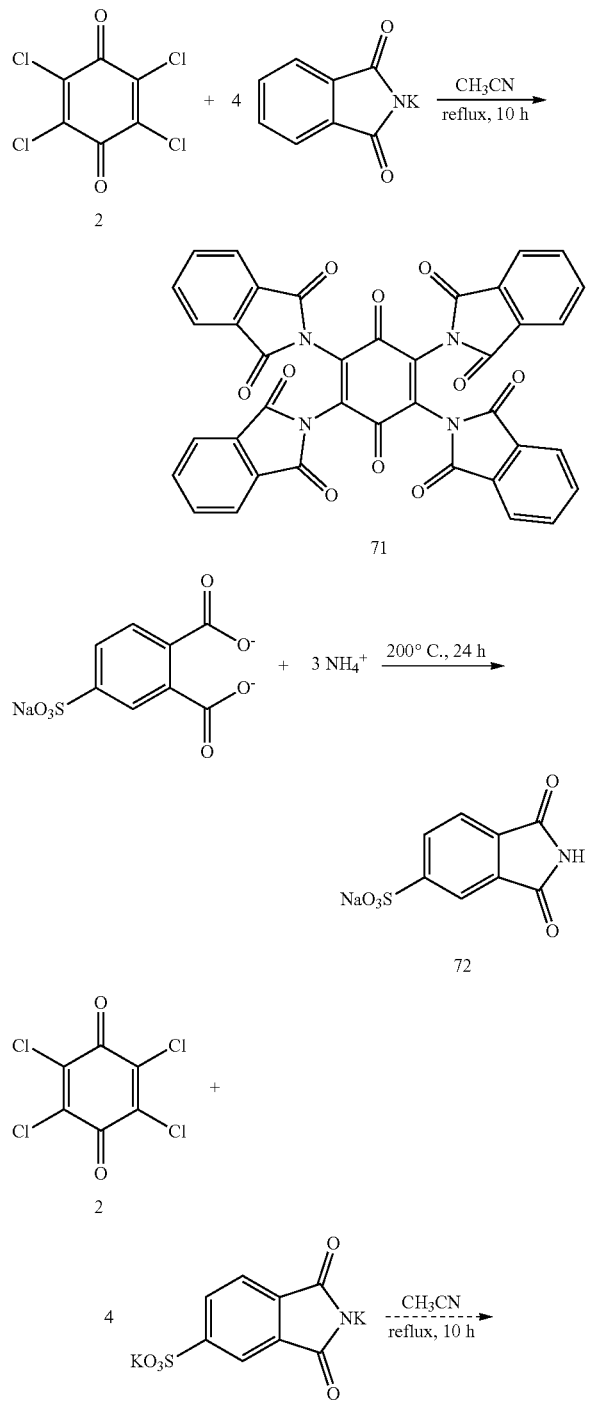

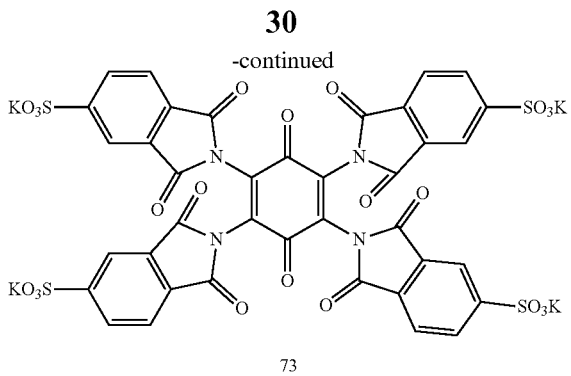

Alternatively, an attached maleimide could be sulfonated, such as proposed to form structure 74, shown in Scheme 22.

Scheme 22. Proposed synthesis of structure 74.

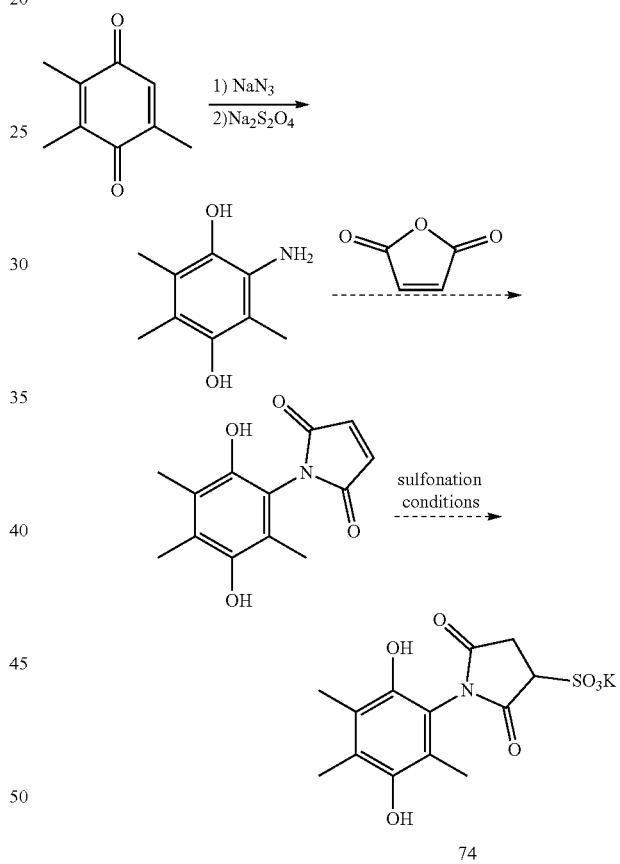

Figure 6A:
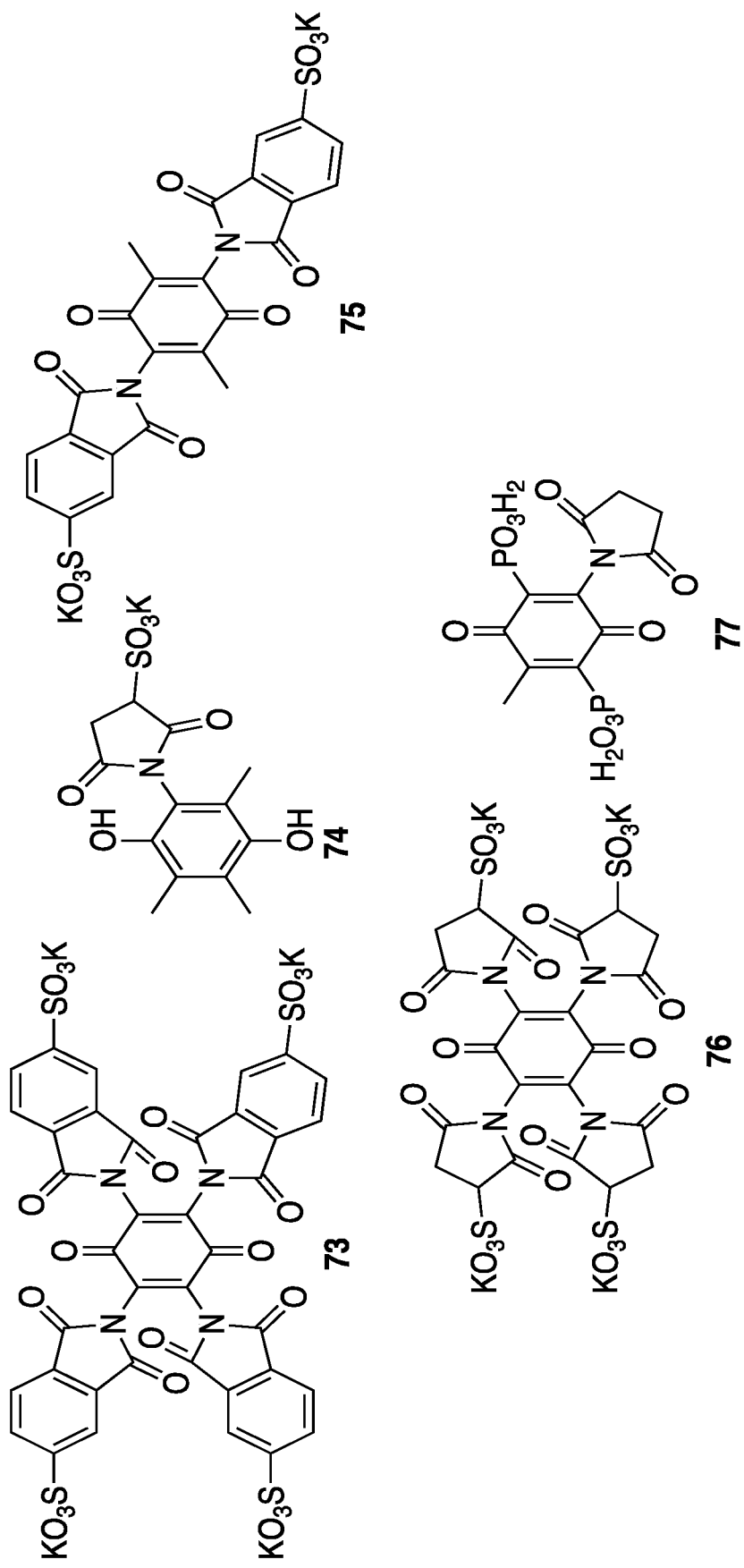
FIGS. 6A and 6B show the chemical structure of an additional 11 exemplary substituted hydroquinones and quinones (compounds 73-77, 79, 85-86, 88, 90, 92).

Other illustrative examples of hydroquinones with solubilizing imides and other groups or solubilizing groups in addition to imides is shown in FIG. 6A, structures 75-77.

Example 14—Alternative Sulfonation and Sulfomethylation Methods

In this example, we disclose alternative methods of sulfonation and sulfomethylation that could be used to produce the quinones or hydroquinones. In Scheme 23, we disclose a method of attaching a methylsulfonate to an unsubstituted hydroquinone. This method can be extended to substituted hydroquinones as well.[45]

Scheme 23: Sulfomethylation of hydroquinone.

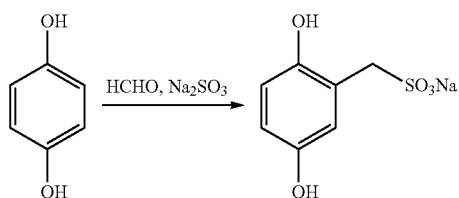

In Scheme 24, we disclose a method of attaching a two methylsulfonates to a ketone-substituted hydroquinone.[45] This method can be extended to more substituted hydroquinones as well. "PG" represents a protecting group, which are well-known in the art.

Scheme 24: Sulfomethylation of ketone-substituted hydroquinone.

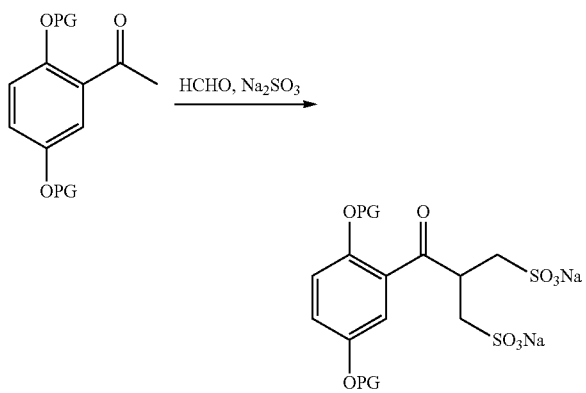

In Scheme 25, we disclose a method of attaching a sulfonate to either end of the double bond of a propenyl-substituted hydroquinone.[46] This method can also be extended to more substituted hydroquinones as well. "PG" represents a protecting group, which are well-known in the art.

Scheme 25: Sulfonation of propenyl-substituted hydroquinone.

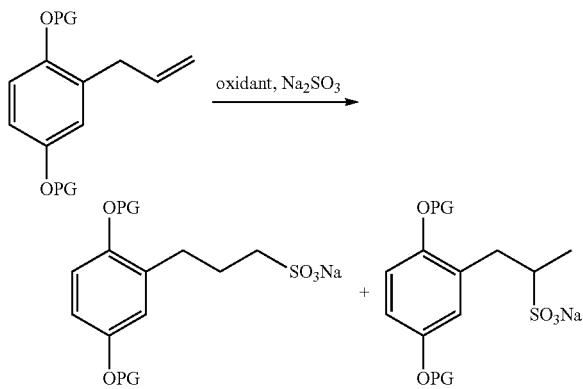

A series of alkyl- or fluoroalkyl-tethered sulfonate-containing hydroquinones could be accessed via the common 1,4-ditrifluoromethyl-2,5-diiodo-3,6-dimethoxybenzene intermediate 78. Two routes to this proposed intermediate are shown in Scheme 26. The first route involves treatment of 1,4-dimethoxybenzene with n-BuLi and TMSCl to form the silylated product,[47] treatment with Togni's reagent to install two $CF_3$ groups, and treatment with ICl to install the two iodine substituents on 78. The second route involves direct iodination of the 1,4-ditrifluoromethyl-2,5-dimethoxybenzene[48] to form 78.

Scheme 26. Two proposed synthetic routes to useful precursor 78.

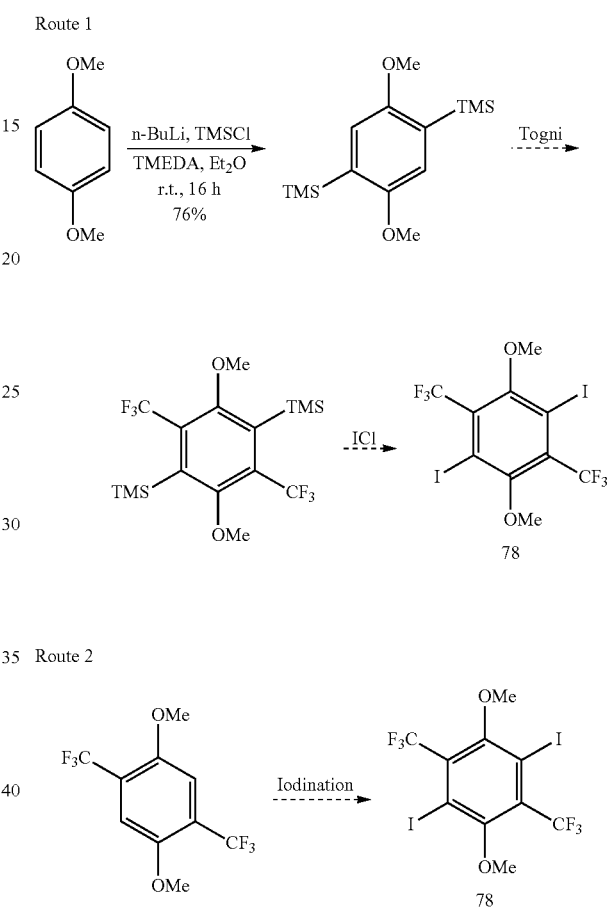

From 78, various tethered sulfonates are proposed be introduced onto the hydroquinone core, as shown in Scheme 27. Treatment with n-Buli and 1,3-propanesultone followed by deprotection could access 79 in Scheme 27. Suzuki coupling of 78 with boronic acid 80 or 81 should access structures 82 and 83. Treatment of 82 with acetic anhydride and sulfuric acid would form the bis-sultone structure 84. Treatment with KF and 18-crown-6 should open the sultones,[49] and methyl deprotection should yield the hydroquinone structure 85. Similar procedures from 83 should yield the hydroquinone structure 86. Conversely, treatment of 78 with $CF_3CO_2Na$ under Cu conditions should yield the tris-$CF_3$ structure 87. Suzuki coupling with 81, sultone formation, ring opening and methyl deprotection as above should yield 88. Ullman-type coupling of 78 with the poly-fluorinated sulfonic acid 89[50] followed by methyl deprotection and hydrolysis could achieve the polyfluorinated hydroquinone structure 90. A similar procedure, using 91[51] as the Ullman coupling partner, could achieve the simpler hydroquinone structure 92.

Figure 6B:
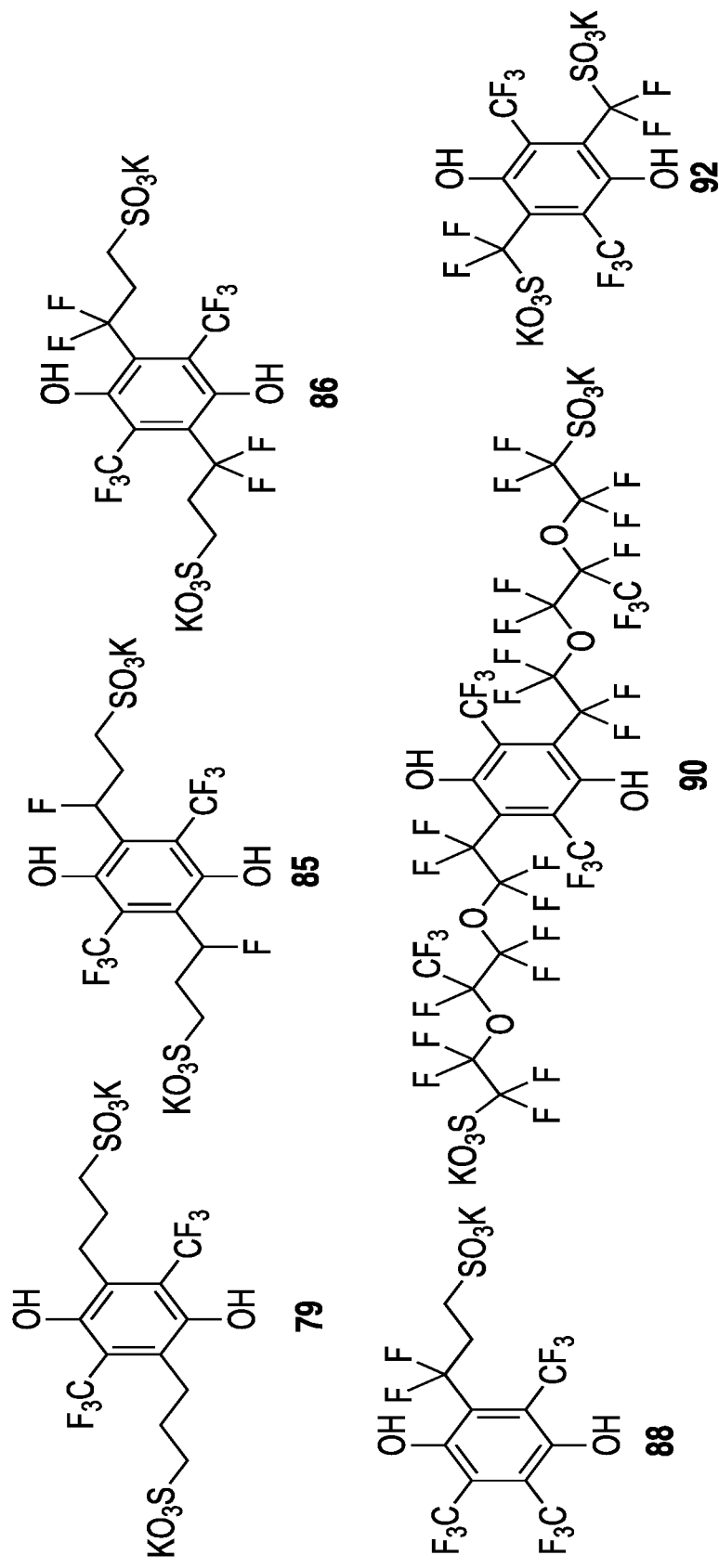

Scheme 27. Proposed synthesis of a fluorine-containing hydroquinone structures 79, 85, 86, 88, 90, and 92 of FIG. 6B.
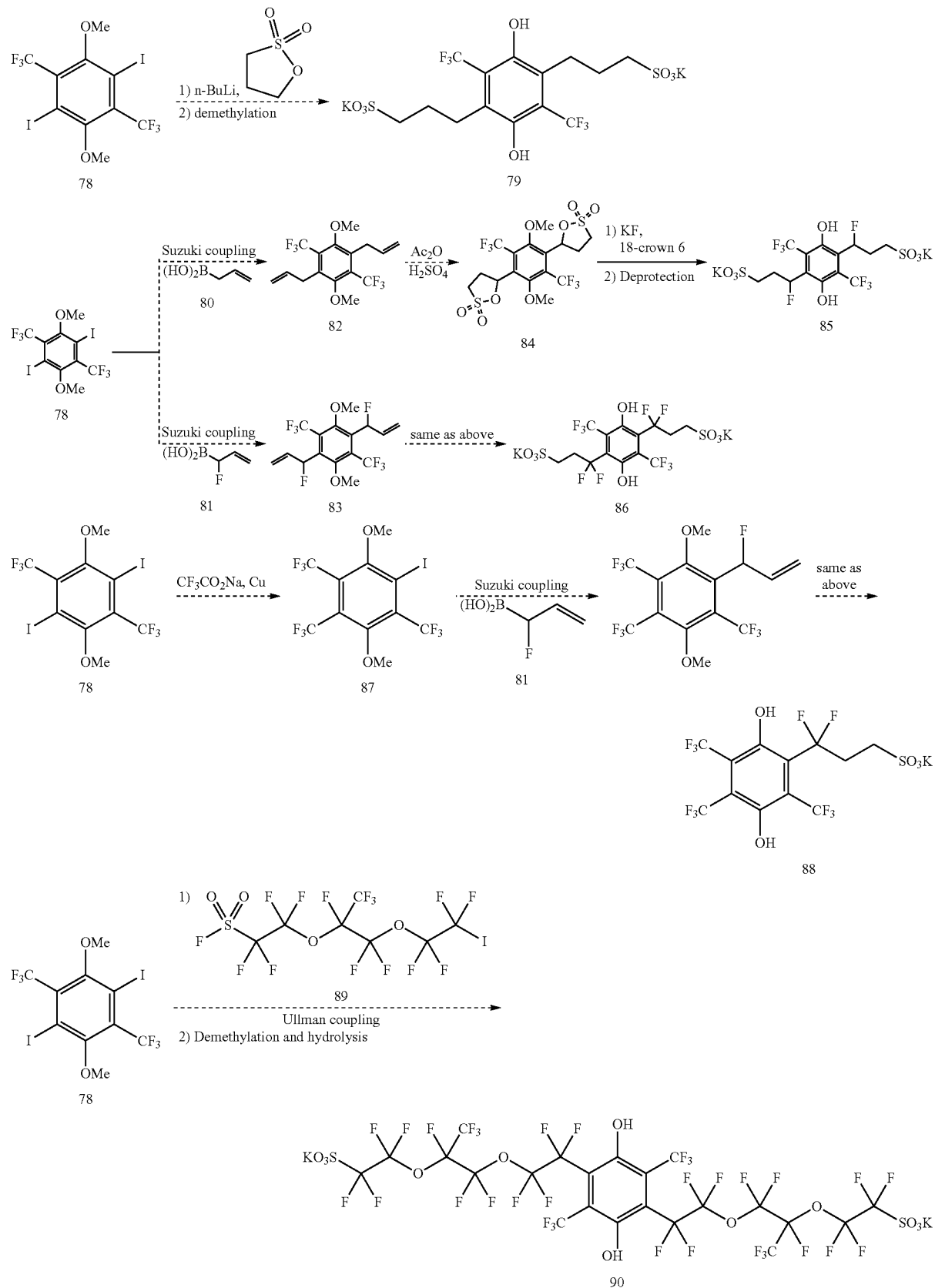

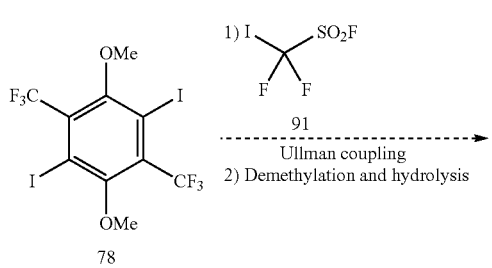 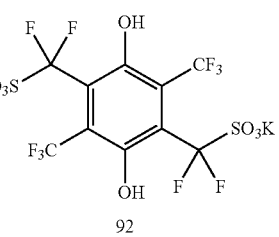

Example 15—Synthesis of 1,2-Hydroquinone/1-2, Quinone Structures

Figure 7A:
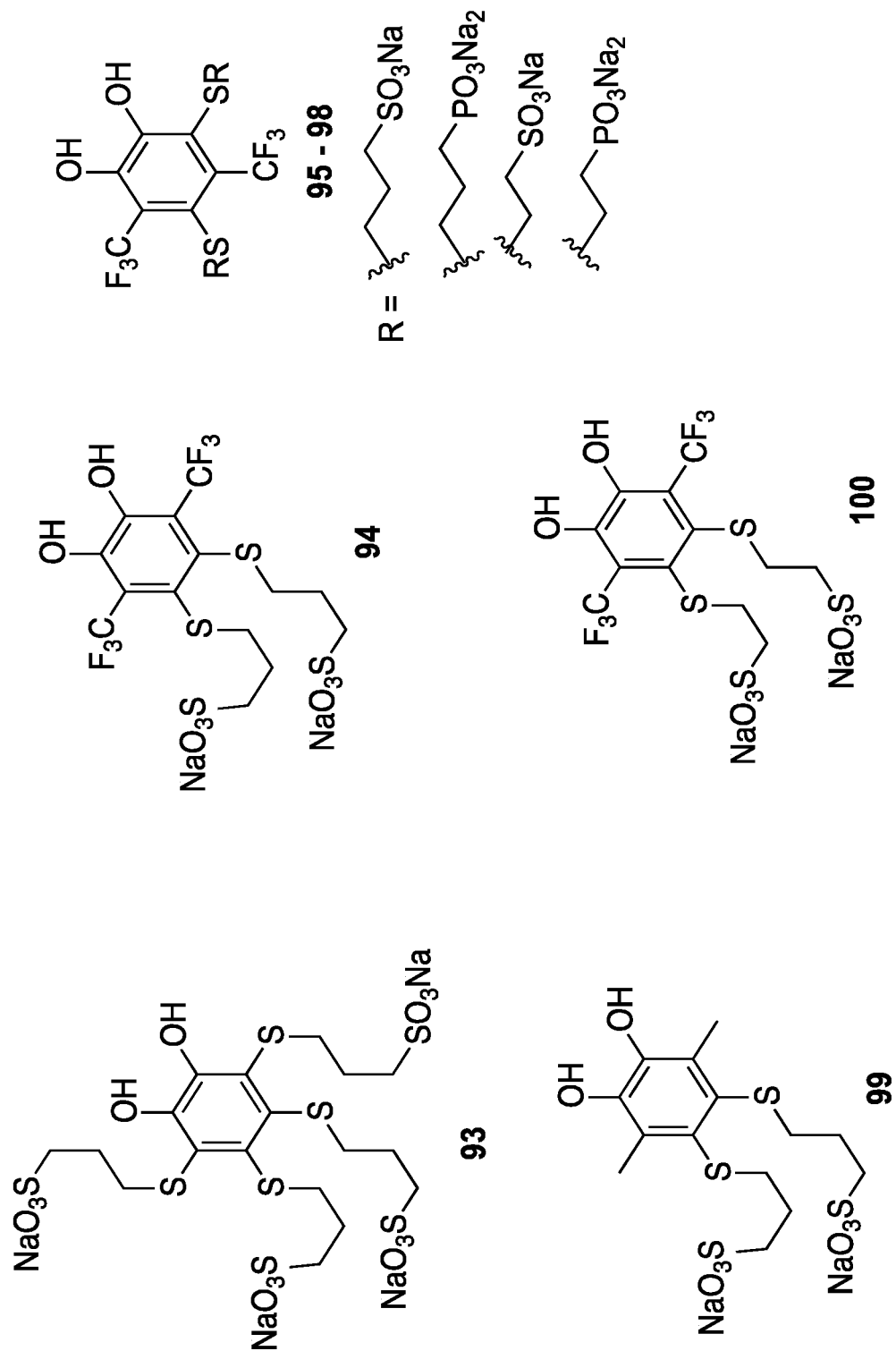
FIGS. 7A and 7B show the chemical structure of 12 exemplary substituted 1,2-hydroquinones and 1,2-quinones (compounds 93-104).
Figure 7B:
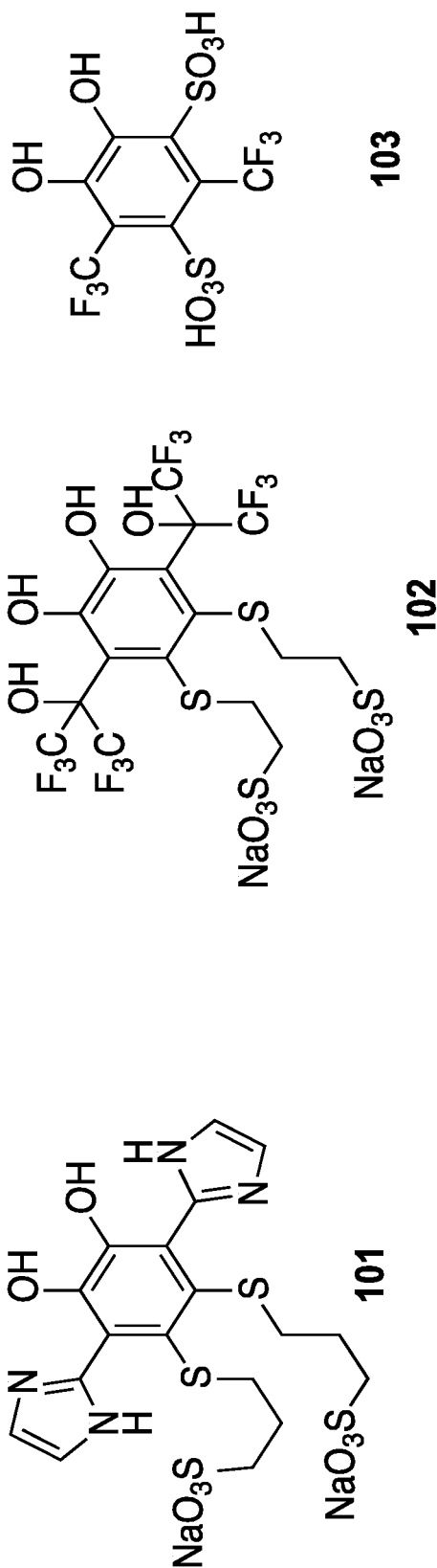

In general, 1,2-quinones have higher reduction potentials than the correspondingly substituted 1,4-quinones. Thus, accessing these structures would be an efficient strategy to achieve quinones with increased redox potentials. Similar sulfonate tethered by thioethers, as used in structure 52 or 54, should give access to higher potential, water-soluble, robust 1,2-hydroquinone structures. Several 1,2-hydroquinone with thioether substituents have been synthesized,[52] though these thioether substituents do not confer water solubility (in fact, thiol addition causes precipitation of the formed structure) and are limited to single or double substitution Preliminary synthetic efforts towards 93 yield a compound with a redox potential of 0.752 V vs. NHE, approximately 100 mV higher than the correspond structures 52 or 54. Using similar procedures as described above for 1,4-hydroquinone/1,4-quinones, 1,2-hydroquinone/1,2-quinone structures 93-104 in FIGS. 7A and 7B should be accessible.

Example 16—Synthesis of Anthraquinones with Tethered Sulfonates and Phosphates Water-soluble anthraquinone structures have been utilized as the anodic mediator in aqueous flow batteries (see for instance U.S. Patent Application 2016/0043423). These structures typically include sulfonate substituents connected directly on the ring. Such compounds have been reported to undergo desulfonation, which leads to precipitation of the structures.[53] For this reason, alternate anthraquinone mediators without sulfonates directly connected to the ring are required. To address this concern, quinone 109 with sulfonate substituents attached to the ring via a thioether tether, was synthesized. Anthraquinones with pendant thioethers have been previously synthesized from the corresponding chlorinated anthraquinones,[54] but not with tethered sulfonates, which would provide increased water solubility, a desired trait.

Figure 9A:
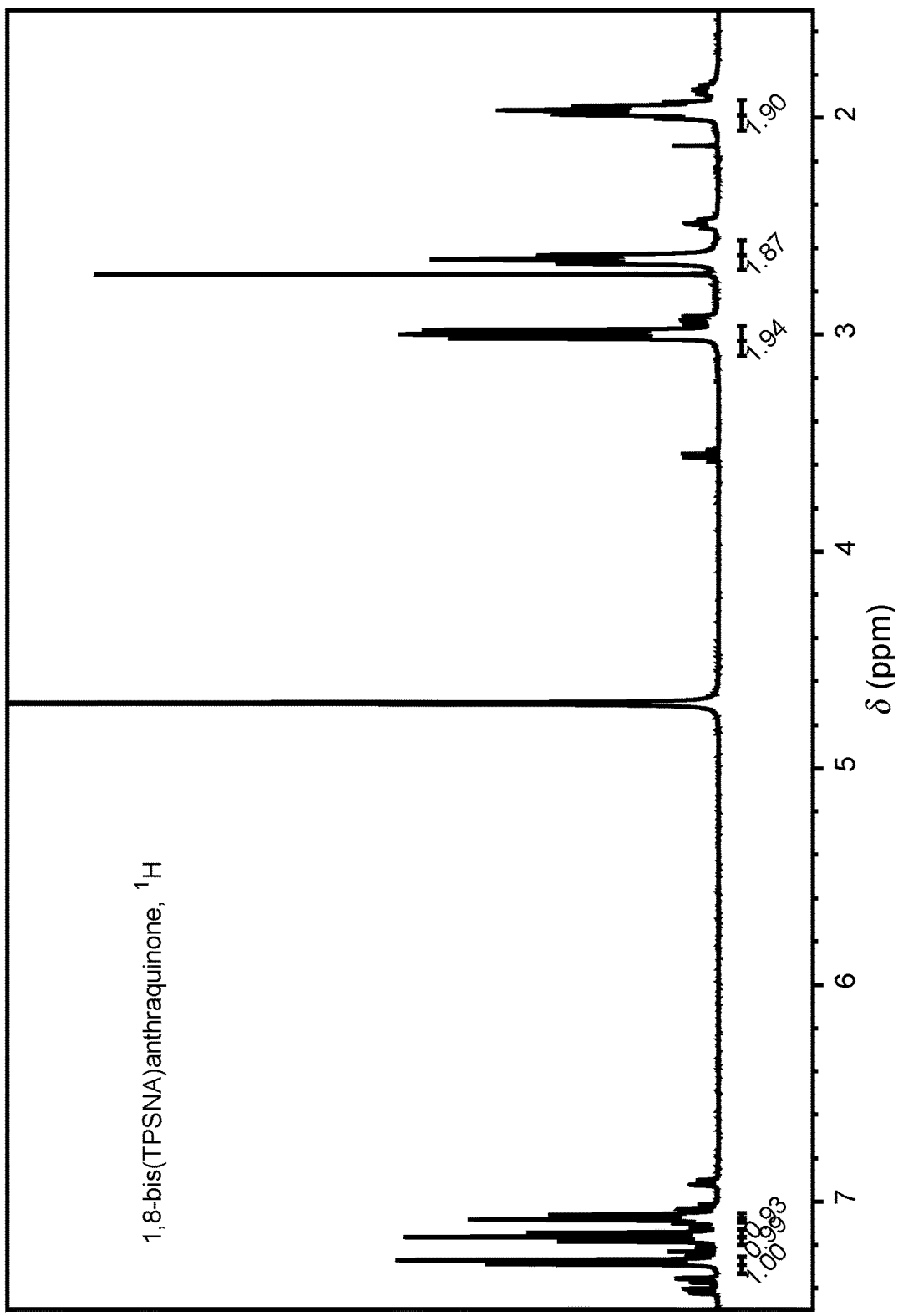
FIGS. 9A and 9B show the $^1$H and $^{13}$C NMR spectrum of compound 109.
Figure 9B:
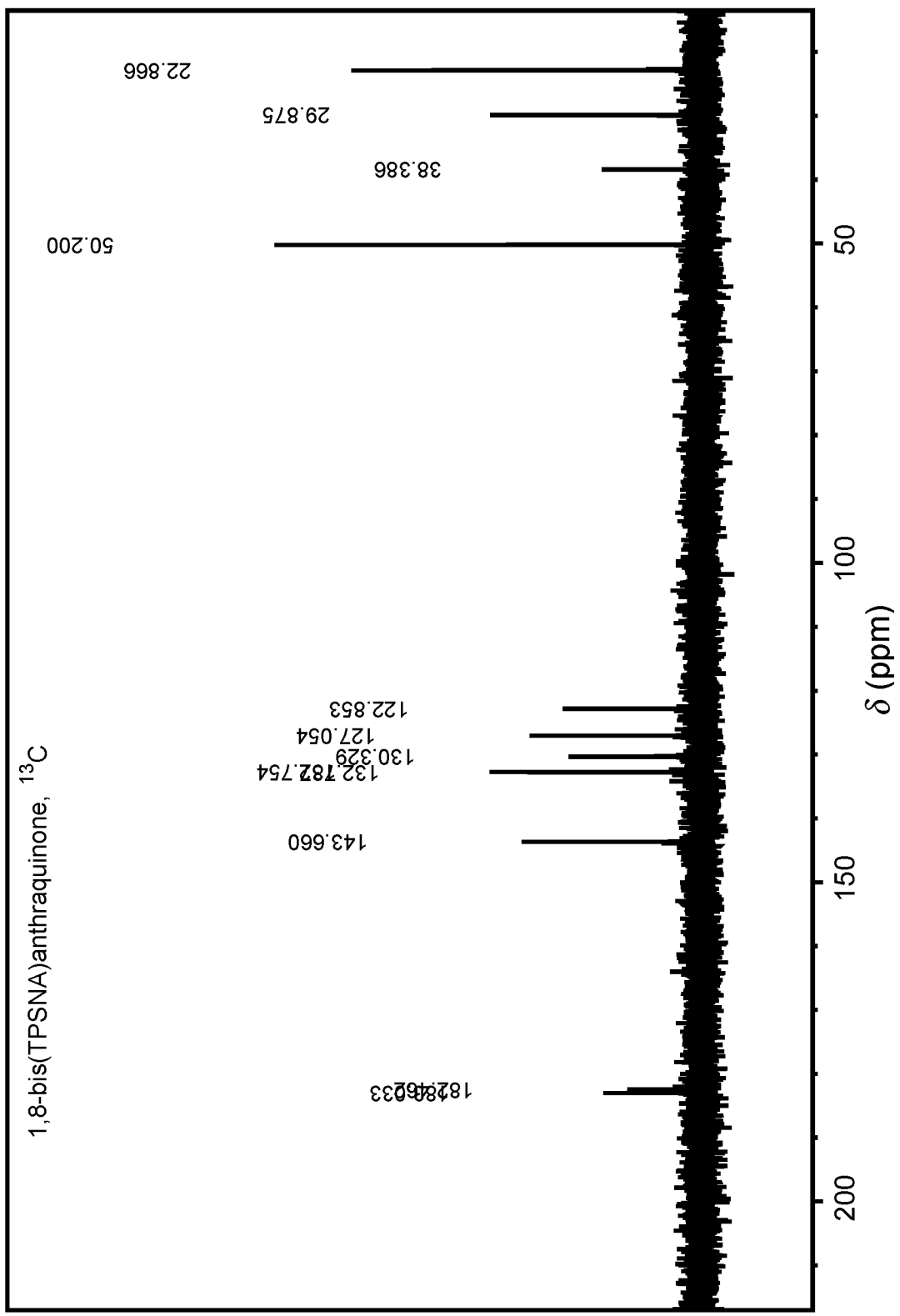

To 3.956 g of sodium 3-mercaptopropanesulfonate dispersed in 50 mL of nitrogen-purged N-methyl pyrrolidinone were added 10.5 mL of 2 M aqueous NaOH. Once mixed, 2.766 g of 1,8-dichloroanthraquinone were added (Scheme 28). The suspension was heated under nitrogen to 90° C. for six days then allowed to cool. 50 mL of water containing 1 mL of acetic acid was added to the cooled solution, which was further diluted with 25 mL water. The solution was extracted with four 50 mL portions of methylene chloride, and the aqueous phase was evaporated. The residue was dissolved with 35 mL of water and 60 mL of methanol was added. The mixture was heated until clear, and left to slowly cool. The resulting crystals were filtered, rinsed twice with 15 mL of 2:1 methanol/water, three times with 15 mL of methanol, and dried to give 4.326 g of material, for an overall yield of 77%. 1H and 13C NMR spectra were obtained (FIGS. 9A and 9B). Cyclic voltammetry of this compound in 1 M $H_2SO_4$ reveal a reduction potential of approximately 85 mV vs. NHE.

Scheme 28. Synthesis of structure 109 from FIG. 8A.

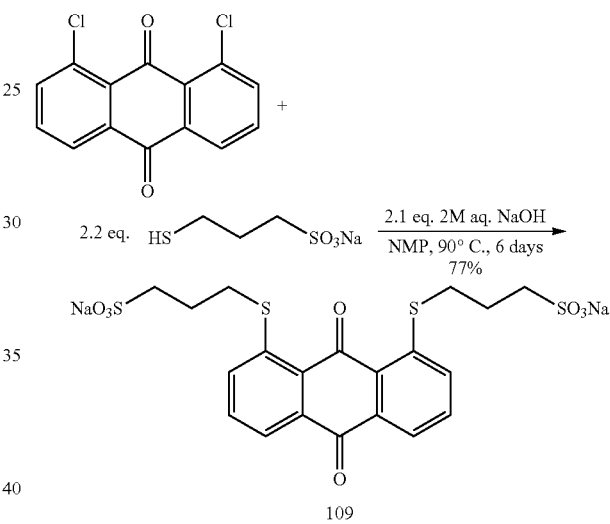

Figure 8A:
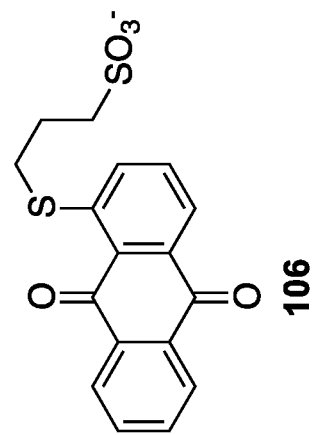
FIGS. 8A and 8B show the chemical structure of 12 exemplary substituted 9,10-anthrahydroquinones and 9,10-anthraquinones (compounds 105-116).
Figure 8A:
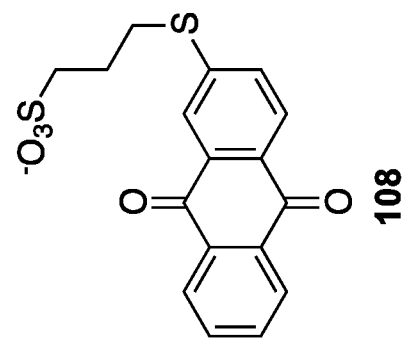
Figure 8A:
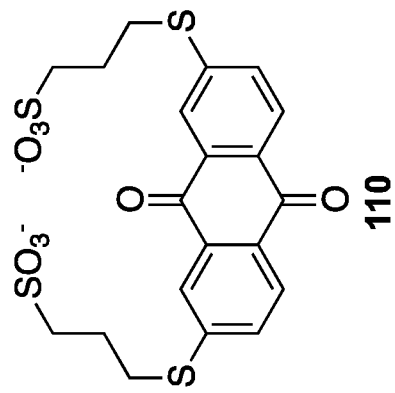
Figure 8A:
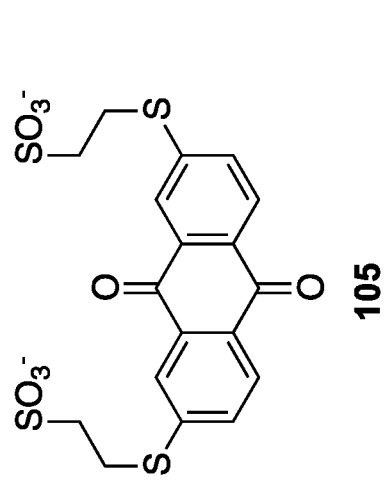
Figure 8A:
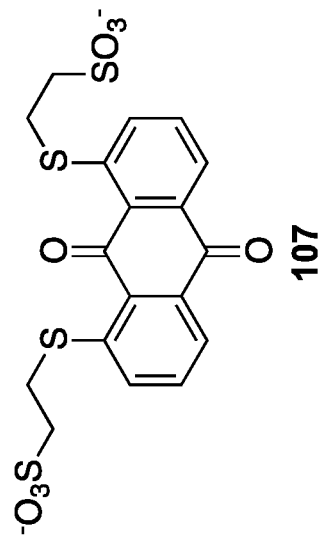
Figure 8A:
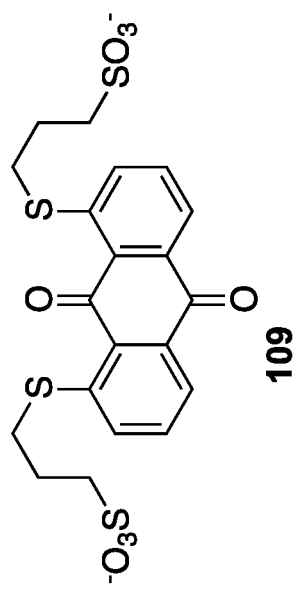
Figure 8B:
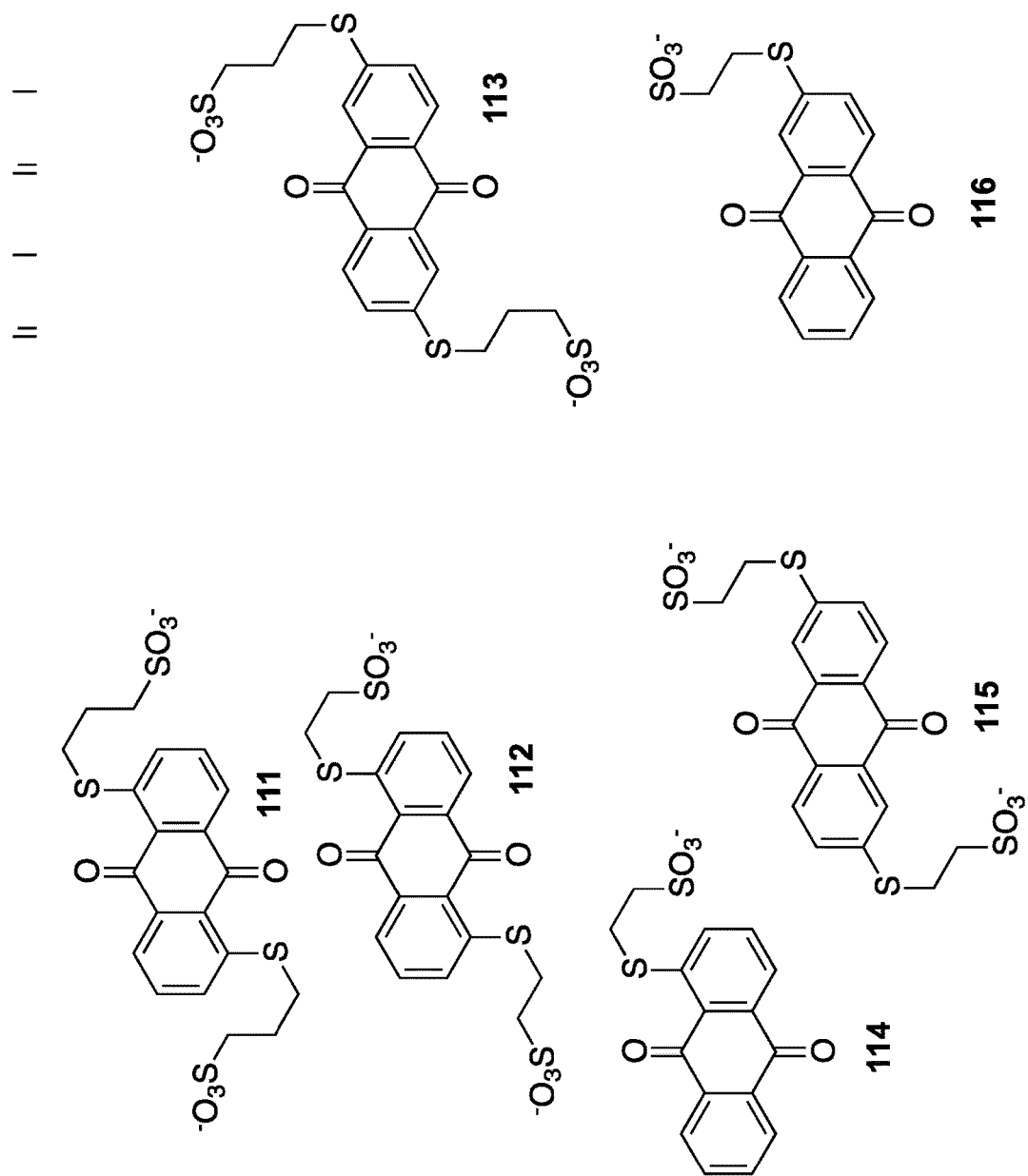
Figure 10A:
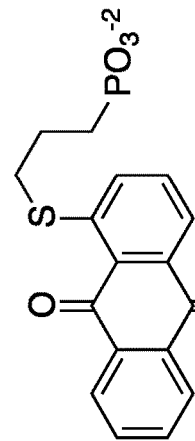
FIGS. 10A and 10B show the chemical structure of 12 exemplary substituted 9,10-anthrahydroquinones and 9,10-anthraquinones (compounds 117-128).
Figure 10A:
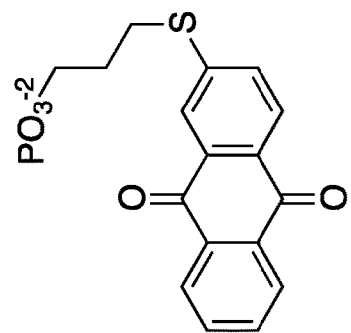
Figure 10A:
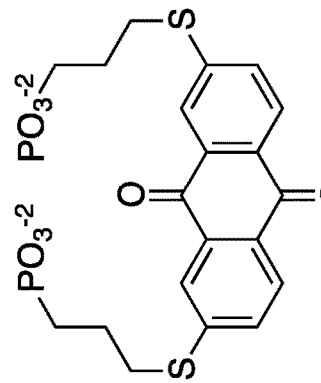
Figure 10A:
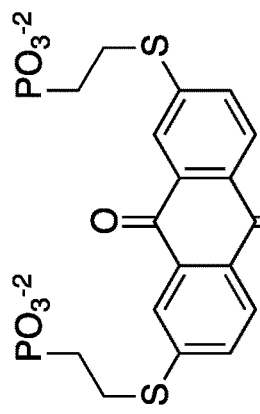
Figure 10A:
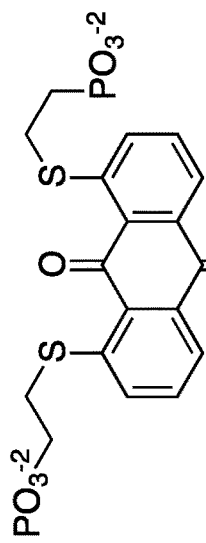
Figure 10A:
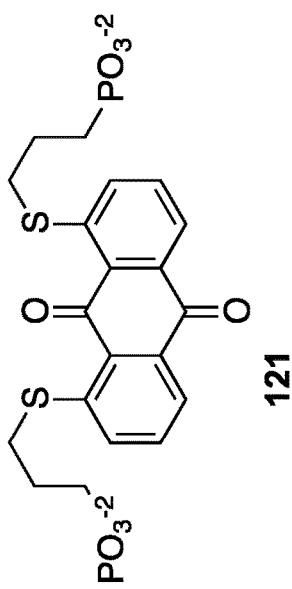
Figure 10B:
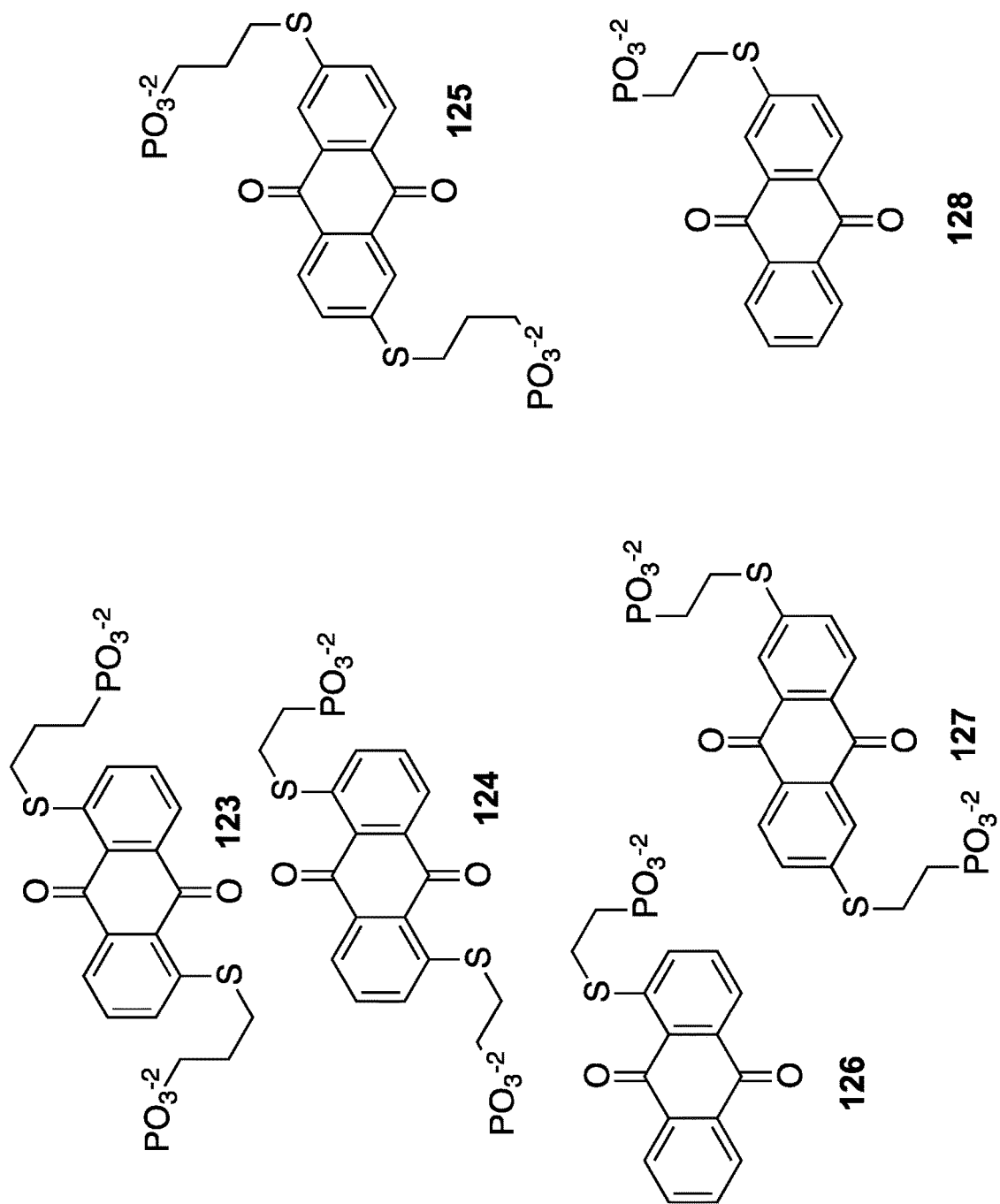
Figure 11A:
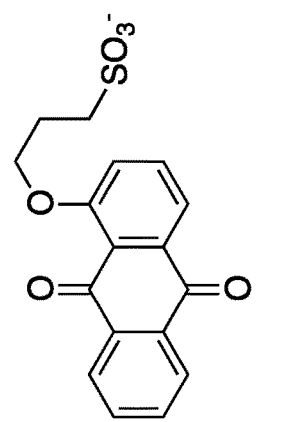
FIGS. 11A and 11B shows the chemical structure of 12 exemplary substituted 9,10-anthrahydroquinones and 9,10-anthraquinones (compounds 129-140).
Figure 11A:
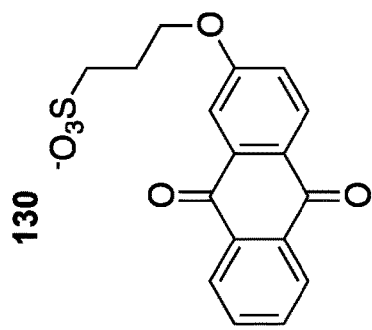
Figure 11A:
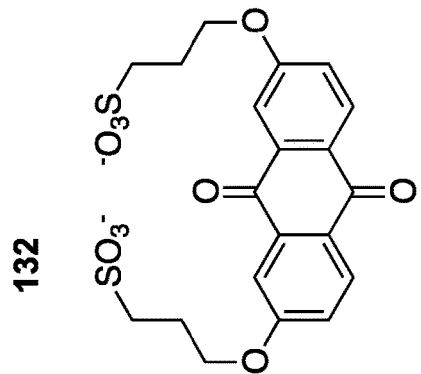
Figure 11A:
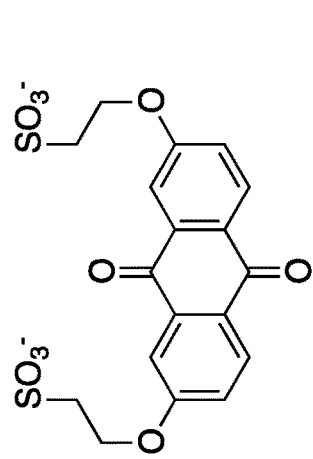
Figure 11A:
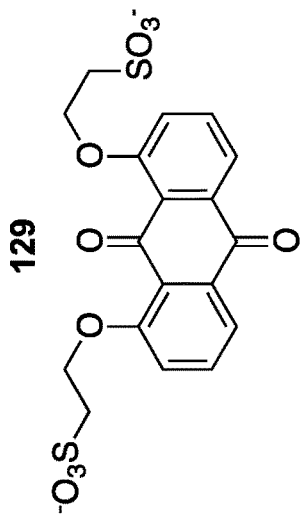
Figure 11B:
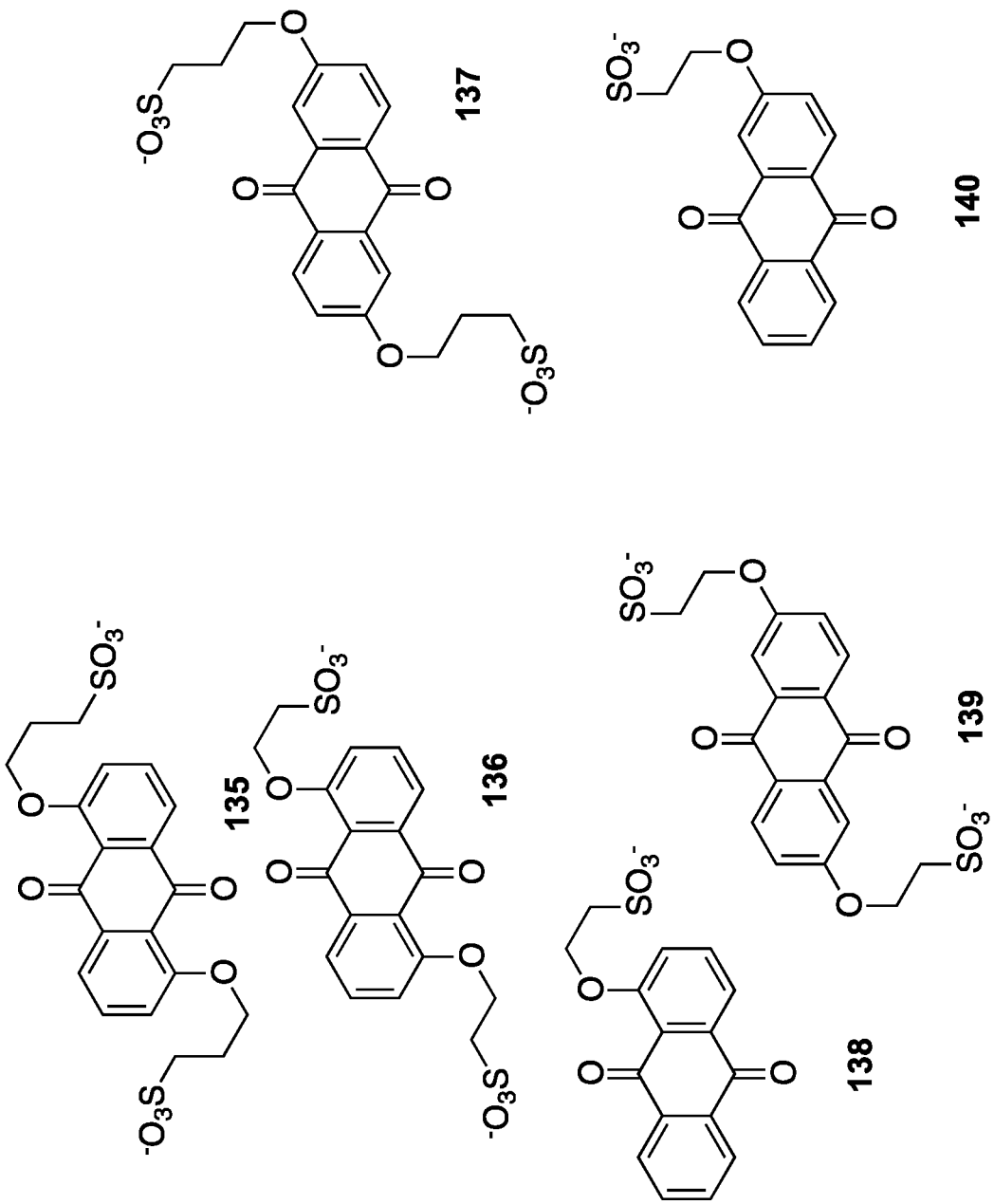

It is expected that related structures, such as structures 105-106 and 108-116 in FIGS. 8A and 8B, structures 117-128 in FIGS. 10A and 10B, and structures 129-140 in FIGS. 11A and 11B could be accessed via similar methods.

Example 17—Synthesis of sodium 3,3'-((2,5-dihydroxy-3,6-bis(trifluoromethyl)-1,4-phenylene)bis(sulfanediyl))bis(pr-opane-1-sulfonate)

Compound 141 has the Following Chemical Structure:

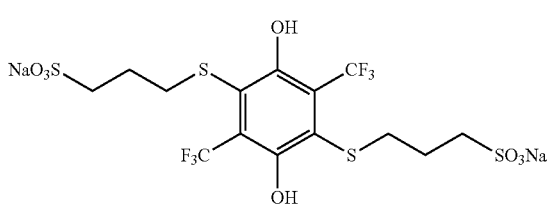

Compound 141 (sodium 3,3'-((2,5-dihydroxy-3,6-bis(trifluoromethyl)-1,4-phenylene)bis(sulfanediyl))bis(pr-opane-1-sulfonate) was synthesized as follows. 2.0 mmol of 2,5-bis(trifluoromethyl) hydroquinone (492 mg) was suspended in 20 mL of a 10% ethoanol in deionized H₂O along with 1.0 mL of 1.0 M H₂SO₄ (aq). The first 4.0 mmol portion of sodium 3-mercaptopropane-1-sulfonate (712 mg) was added to the hydroquinone suspension with stirring. Once MPSNa completely dissolved, the reaction vessel was charged with a glassy carbon working electrode and a nickel wire counter electrode. These electrodes were connected to a galvanostat and the current was set to 20 mA. Subsequent portions of 4.0 mmol MPSNa (712 mg) were added at 24, 48 and 72 hours after the start of the bulk electrolysis. The color of the reaction mixture turned progressively darker over the course of the electrolysis. At 96 h the NMR of the bulk electrolysis showed a >80% conversion to product by $^{19}$F NMR and the electrolysis was halted. After purification on reverse-phase column with deionized H₂O, 407 mg of 141 was obtained.

Isolated Yield: 34%; Physical Property: Brown solid.

Figure 12A:
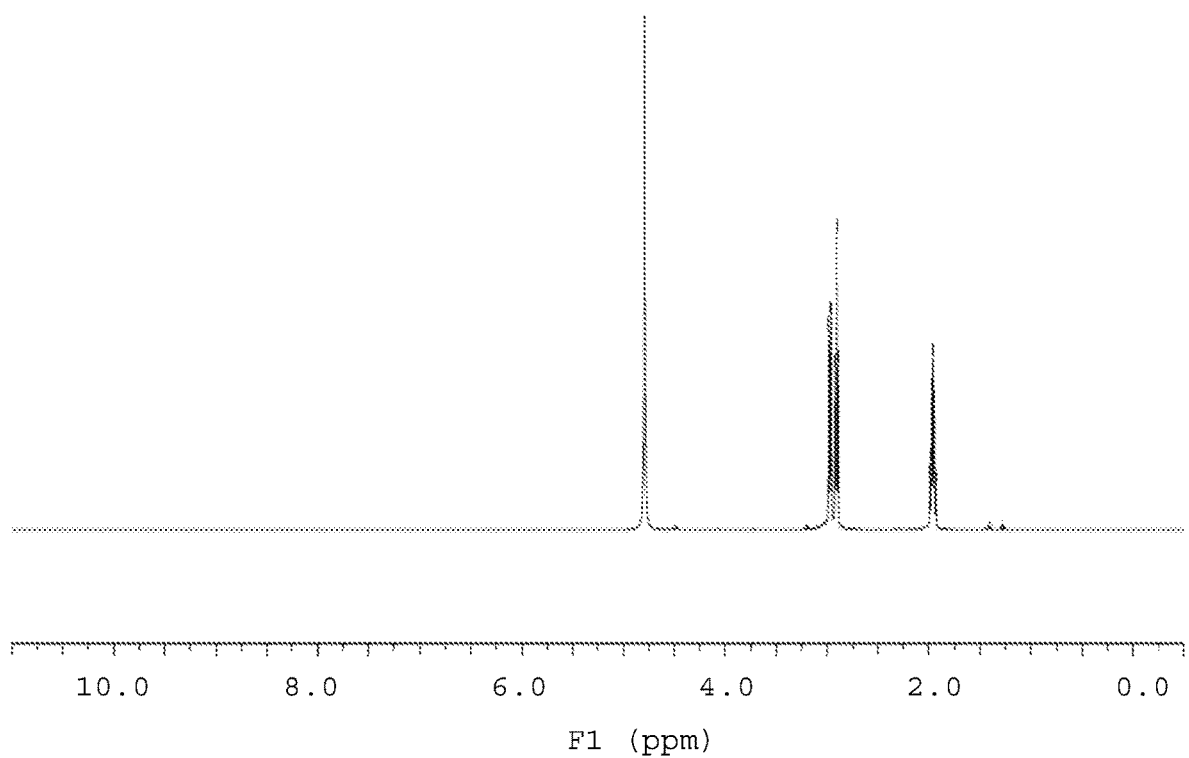
FIG. 12A shows the $^1$H NMR spectrum of compound 141 in D$_2$O (500 MHz).
Figure 12B:
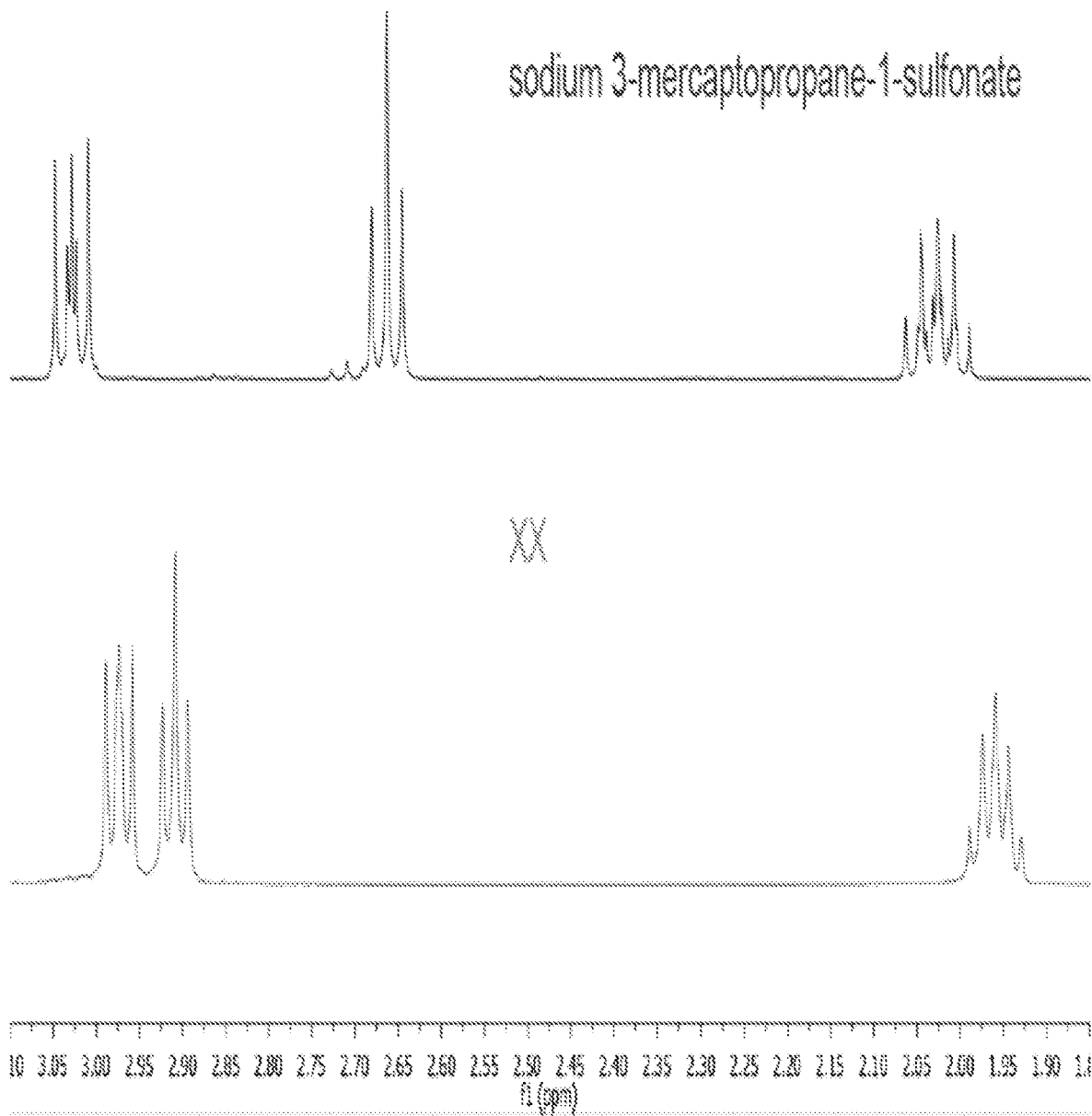
FIG. 12B shows the $^1$H NMR spectrum of compound 141 and sodium 3-mercaptopropane-1-sulfonate in D$_2$O (500 MHz).

$^1$H NMR (500 MHz, D₂O); δ 3.00-2.94 (m, 4H), 2.91 (t, $J_{HH}$=7.3 Hz, 4H), 2.01-1.91 (m, 4H); see FIGS. 12A and 12B.

Figure 13A:
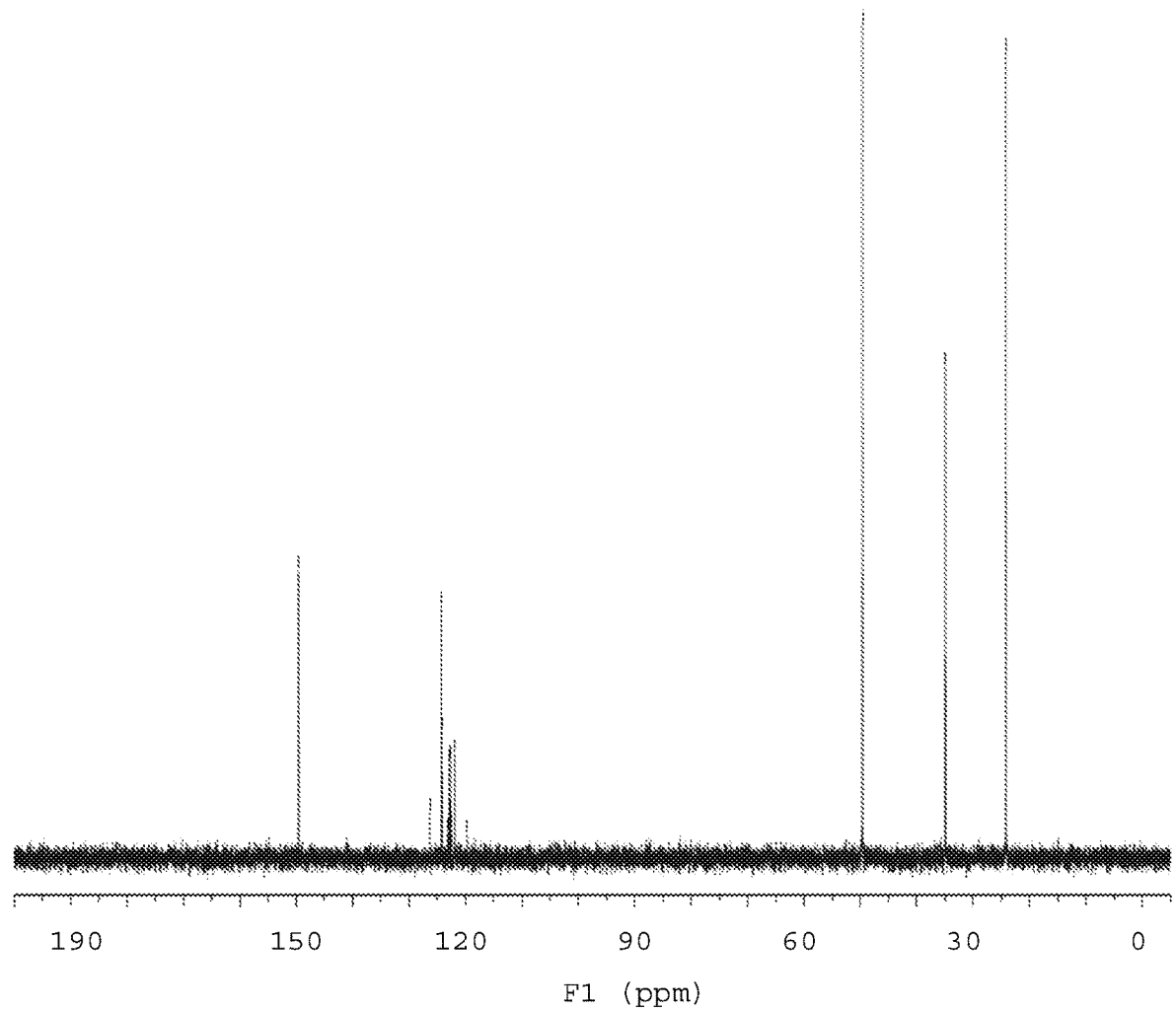
FIG. 13A shows the $^{13}$C NMR spectrum of compound 141 in D$_2$O (125 MHz).
Figure 13B:
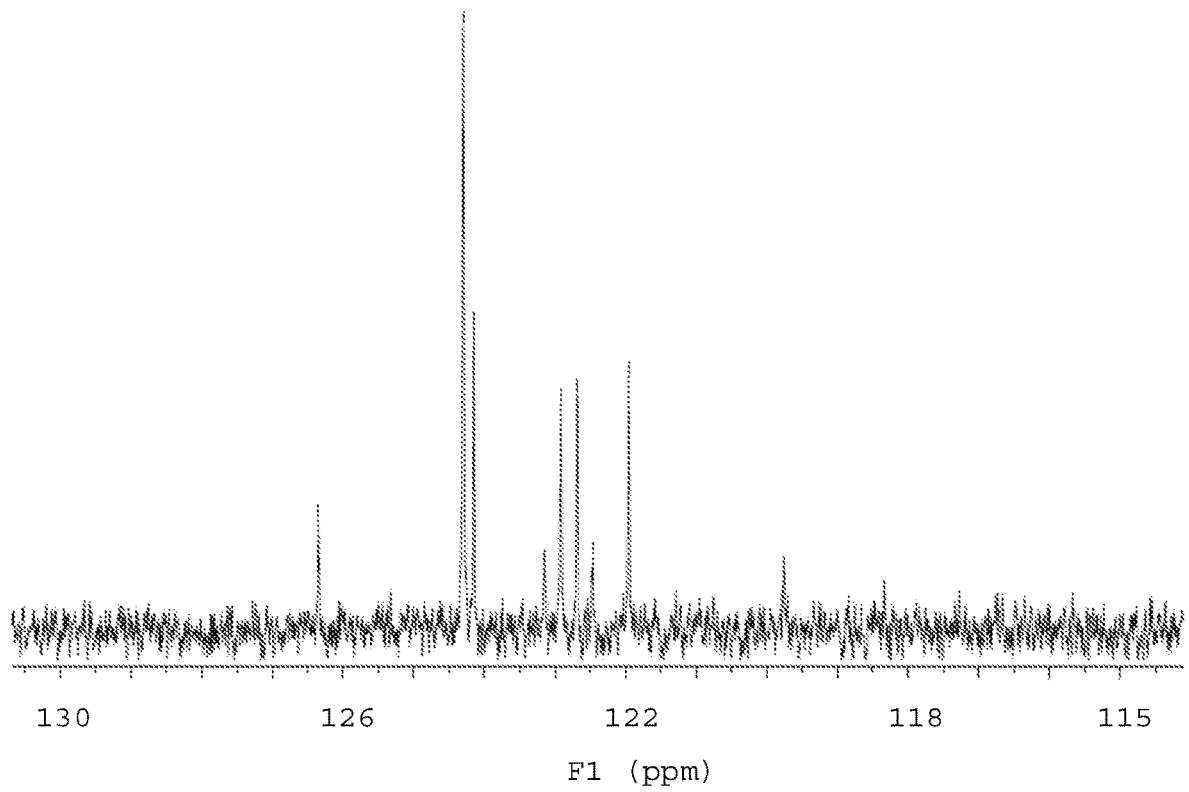
FIG. 13B shows the zoomed-in $^{13}$C NMR spectrum of compound 141 in D$_2$O (125 MHz).

$^{13}$C NMR (125 MHz, D₂O); δ 149.58, 124.3, 123.1 (q, $J_{CF}$=276.3 Hz) 122.8 (q, $J_{CF}$=29.0 Hz), 49.52, 34.88, 24.19; see FIGS. 13A and 13B.

Figure 14:
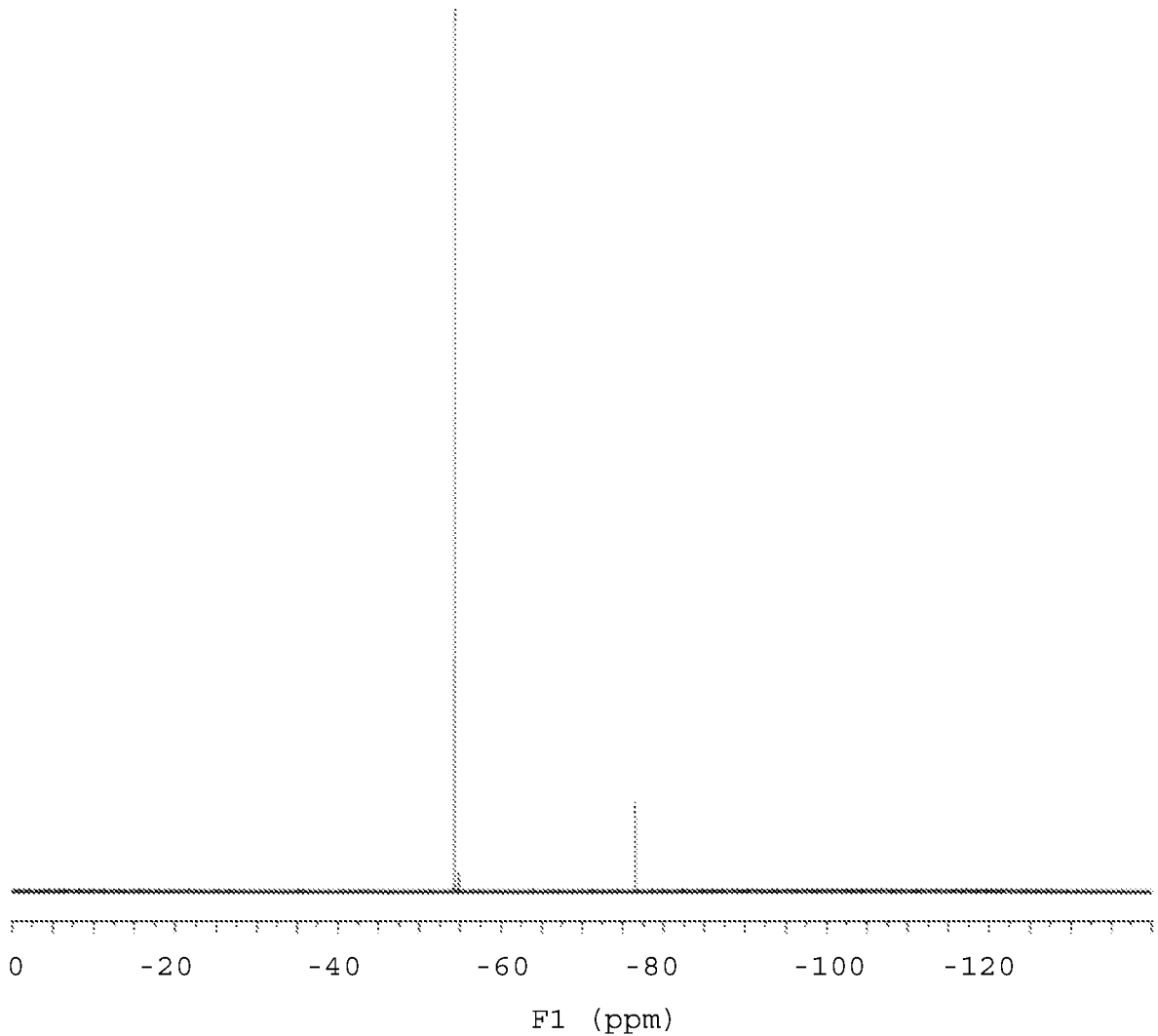
FIG. 14 shows the $^{19}$F NMR spectrum of compound 141 in 0.1% TFA in D$_2$O (338 MHz).

$^{19}$F NMR (338 MHz, 0.1% TFA in D₂O), δ −54.3 (see FIG. 14).

HRMS (ESI) calculated for $C_{14}H_{14}F_6O_8S_4^{2-}$ [M-2Na]² 275.9743, found 275.9738.

In the following examples, we further disclose further methods for synthesizing the substituted hydroquinones/benzoquinones.

In method 1, a mercaptoalkylsulfonate is dissolved in a water solution, and unsubstituted 1,4-benzoquinone is added. The reaction is allowed to proceed, and the final thioether sulfonate product is separated out of the reaction mixture.

In method 2, unsubstituted 1,4-benzoquinone is suspended in an acidic alcohol/water solution water. Separately, a mercaptoalkylsulfonate is dissolved in a water solution, after which it is added to the benzoquinone suspension over a period of time and allowed to react. A second portion of 1,4-benzoquinone is then added to the reaction mixture, producing a blood-red solution. Separately, another mercaptoalkylsulfonate solution is prepared, added to the reaction mixture, and allowed to react. These two steps may be repeated a third and fourth time, after which the reaction solution is filtered and extracted to form the substituted crystalline thioether sulfonate product.

In method 3, unsubstituted 1,4-benzoquinone is reacted with a mercaptoalkylsulfonate to form a hydroquinone adduct. The adduct is then oxidized electrochemically in the presence of further mercaptoalkylsulfonate at a potential where the mercaptoalkylsulfonate does not oxidize readily to its disulfide. The process is repeated under continuing electrolysis until all four thioether sulfonate groups are added.

Example 18—Synthesis of an Exemplary Hydroquinone Substituted with Four Thioether Sulfonates: 2,3,5,6-tetrakis(ethylsulfanyl-2'-sulfonate)-1,4-hydroquinone tetrasodium salt Method 1:

To 0.655 g of sodium 2-mercaptoethanesulfonate (MESNA) dissolved in 10 ml of water with 60 μl of acetic acid was added 0.438 g of 1,4-benzoquinone. This solution was allowed to stir for 1 hour and then filtered. The solids were rinsed with 5 ml of water and then the combined filtrate was extracted thrice with 5 ml portions of ethyl acetate. The aqueous phase was diluted with 30 ml of ethanol, heated until clear, and left to cool slowly. The resulting crystals were filtered and dried.

Figure 15:
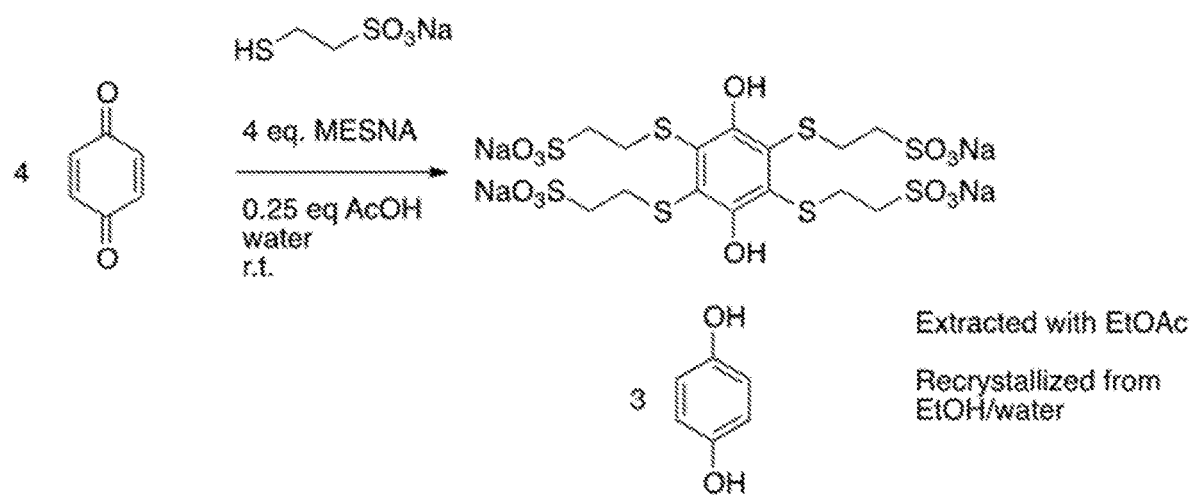
FIG. 15 is a synthesis scheme (Scheme 29) illustrating the use of method 1 to synthesize 2,3,5,6-tetrakis(ethylsulfanyl-2'-sulfonate)-1,4-hydroquinone tetrasodium salt, using sodium 2-mercaptoethanesulfonate (MESNA) and 1,4-benzoquinone (compound 4) as reactants.
Figure 16:
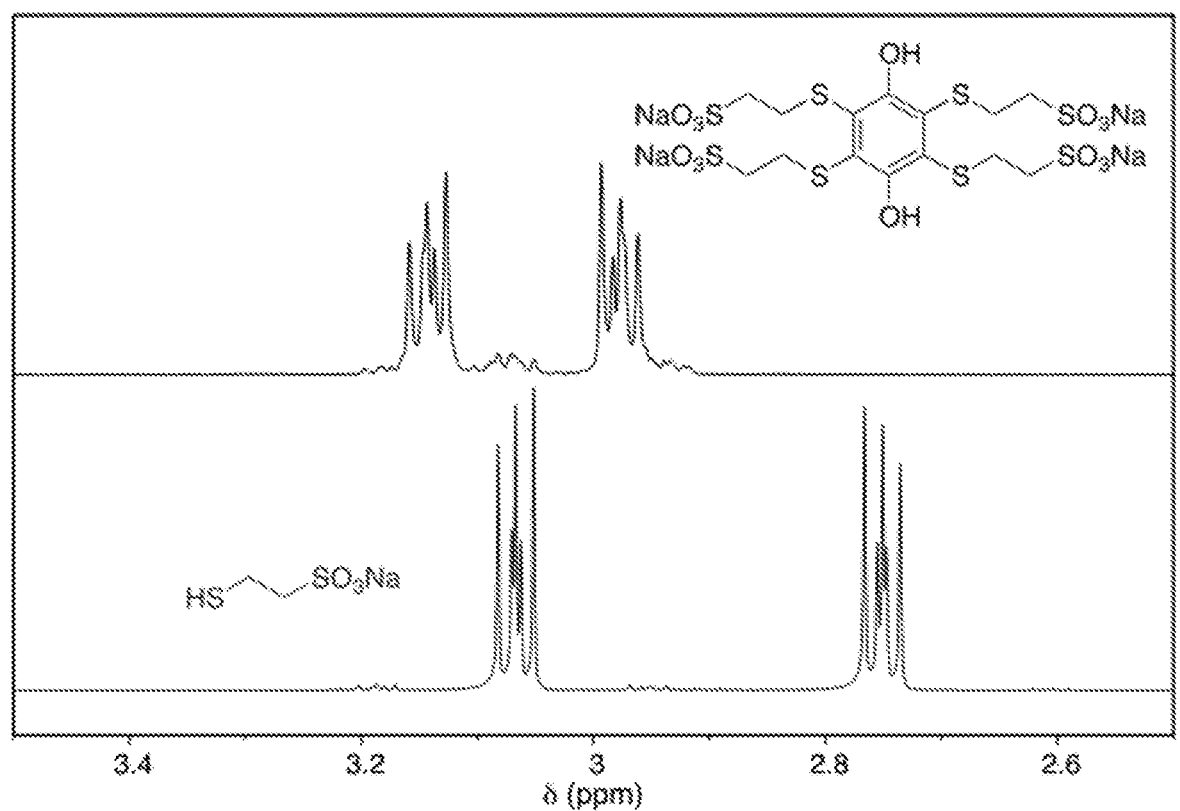
FIG. 16 shows $^1$H NMR spectra of the 2,3,5,6-tetrakis(ethylsulfanyl-2'-sulfonate)-1,4-hydroquinone tetrasodium salt product (top panel) and the sodium 2-mercaptoethanesulfonate (MESNA) reactant (bottom panel) in D$_2$O, as used/made by method 1.

In this manner, as shown in Scheme 29 (see FIG. 15), 2,3,5,6-tetrakis(ethylsulfanyl-2'-sulfonate)-1,4-hydroquinone tetrasodium salt was isolated and identified by NMR spectroscopy (see FIG. 16).

Method 2:

A 105 mg portion of benzoquinone was suspended in 1 ml of ethanol and 9.9 ml of water plus 0.1 ml of 1 M aqueous sulfuric acid was added. Separately, 0.166 g of MESNA was dissolved in 2 ml of water. The MESNA solution was added to the benzoquinone suspension with stirring over a period of 17 minutes and then allowed to stir under a nitrogen atmosphere for 50 minutes. During this time, the initial claret color faded through kool-aid red to a pale pink similar to ashes of rose.

A second 106 mg portion of benzoquinone was added to the reaction mixture and allowed to stir with dissolution for 15 minutes to produce a blood-red solution. Separately, 0.165 g of MESNA was dissolved in 1.5 ml of water. The MESNA solution was added to the quinone mixture with stirring over a period of 30 minutes and then allowed to stir under a nitrogen atmosphere for 50 minutes as its color faded.

A third 112 mg portion of benzoquinone was added to the reaction mixture and allowed to stir with dissolution for 15 minutes to produce a blood-red solution. Separately, 0.166 g of MESNA was dissolved in 2.2 ml of water. The MESNA solution was added dropwise to the quinone mixture with stirring and then allowed to stir under a nitrogen atmosphere until its color had faded again.

A fourth 104 mg portion of benzoquinone was added to the reaction mixture and allowed to stir with dissolution to produce a blood-red solution. Separately, 0.166 g of MESNA was dissolved in 2.2 ml of water. The MESNA solution was added to the quinone mixture dropwise with stirring and then allowed to stir under a nitrogen atmosphere for two days.

The reaction solution was filtered, extracted with 6 ml of ethyl acetate, and the aqueous phase was treated with sodium bisulfate to reduce any residual quinone. The aqueous solution was then extracted with three 6-ml portions of ethyl acetate. The resulting aqueous solution was diluted with 40 ml of ethanol, heated to flocculate the product, and allowed to cool slowly. The resulting solids were filtered and rinsed with 2 ml of ethanol.

Figure 17A:
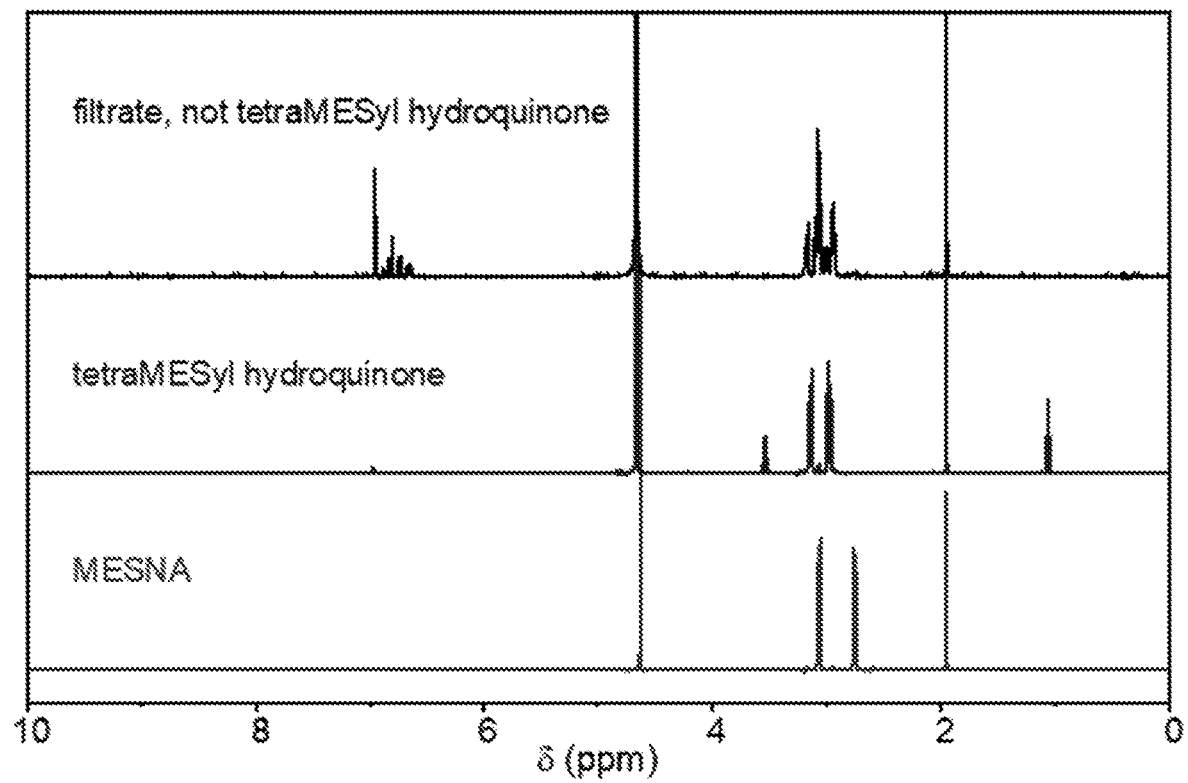
FIGS. 17A and 17B show (17A) $^1$H and (17B) $^{13}$C NMR spectra of the 2,3,5,6-tetrakis(ethylsulfanyl-2'-sulfonate)-1,4-hydroquinone tetrasodium salt product made by method 2.
Figure 17B:
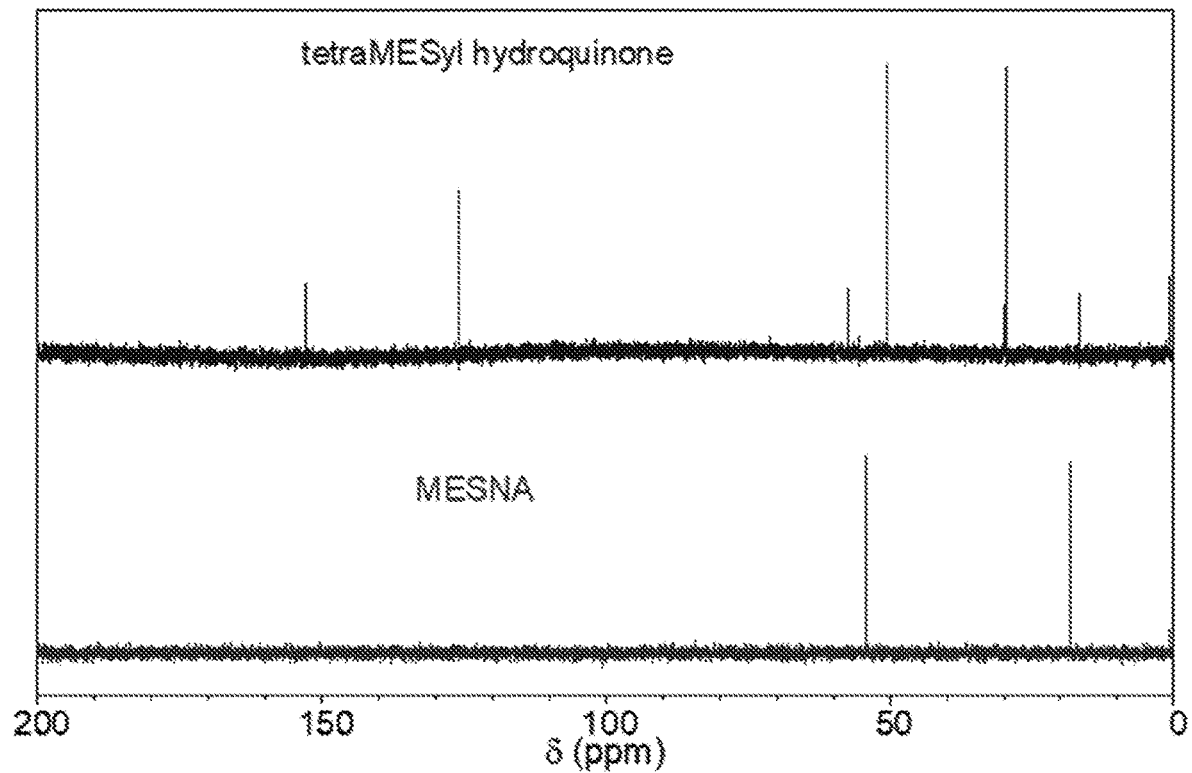

In this fashion, 0.235 g of a white solid were obtained with NMR spectra consistent with formation of the compound 2,3,5,6-tetrakis(ethylsulfanyl-2'-sulfonate)-1,4-hydroquinone tetrasodium salt (see FIGS. 17A and 17B).

Figure 18A:
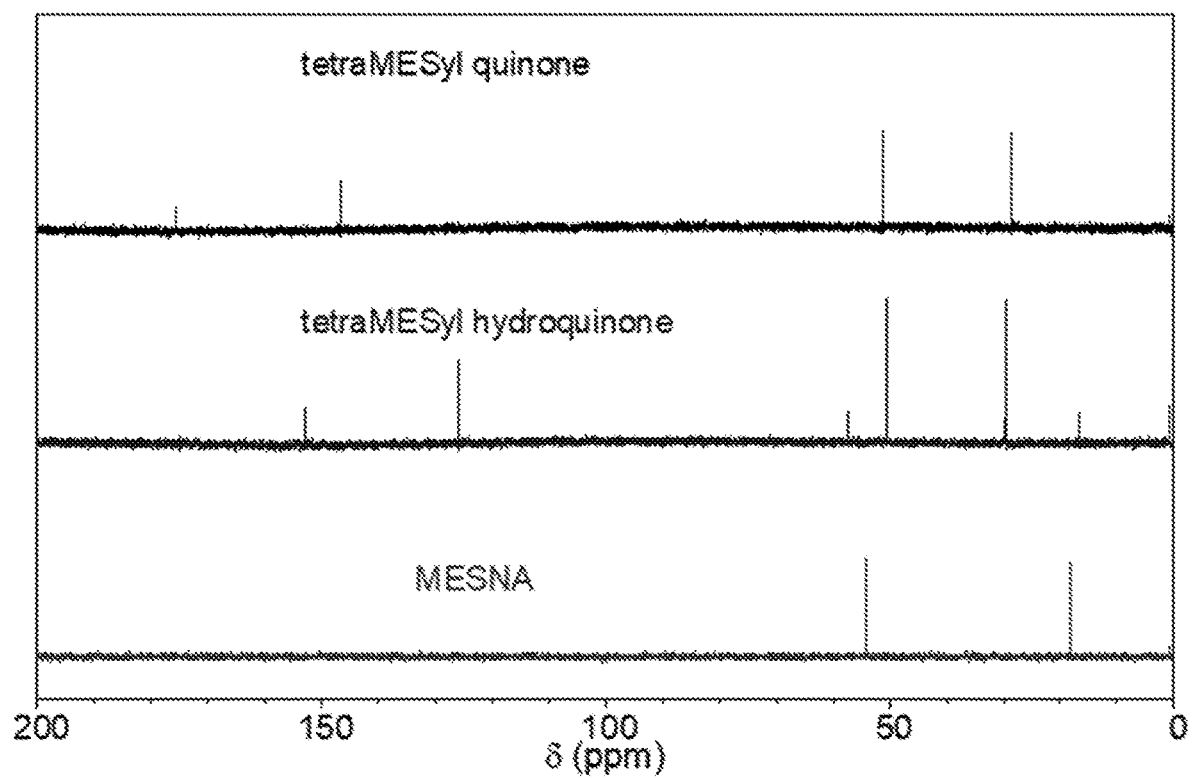
FIGS. 18A and 18B show (18A) $^{13}$C NMR and (18B) $^1$H-$^{13}$C HMBC spectra of the quinone formed by oxidation of the 2,3,5,6-tetrakis(ethylsulfanyl-2'-sulfonate)-1,4-hydroquinone tetrasodium product made by method 2. The HMBC cross-peak at ~150 ppm establishes that the side-chain methylene remains bound to the ring through the thioether linkage after oxidation.
Figure 18B:
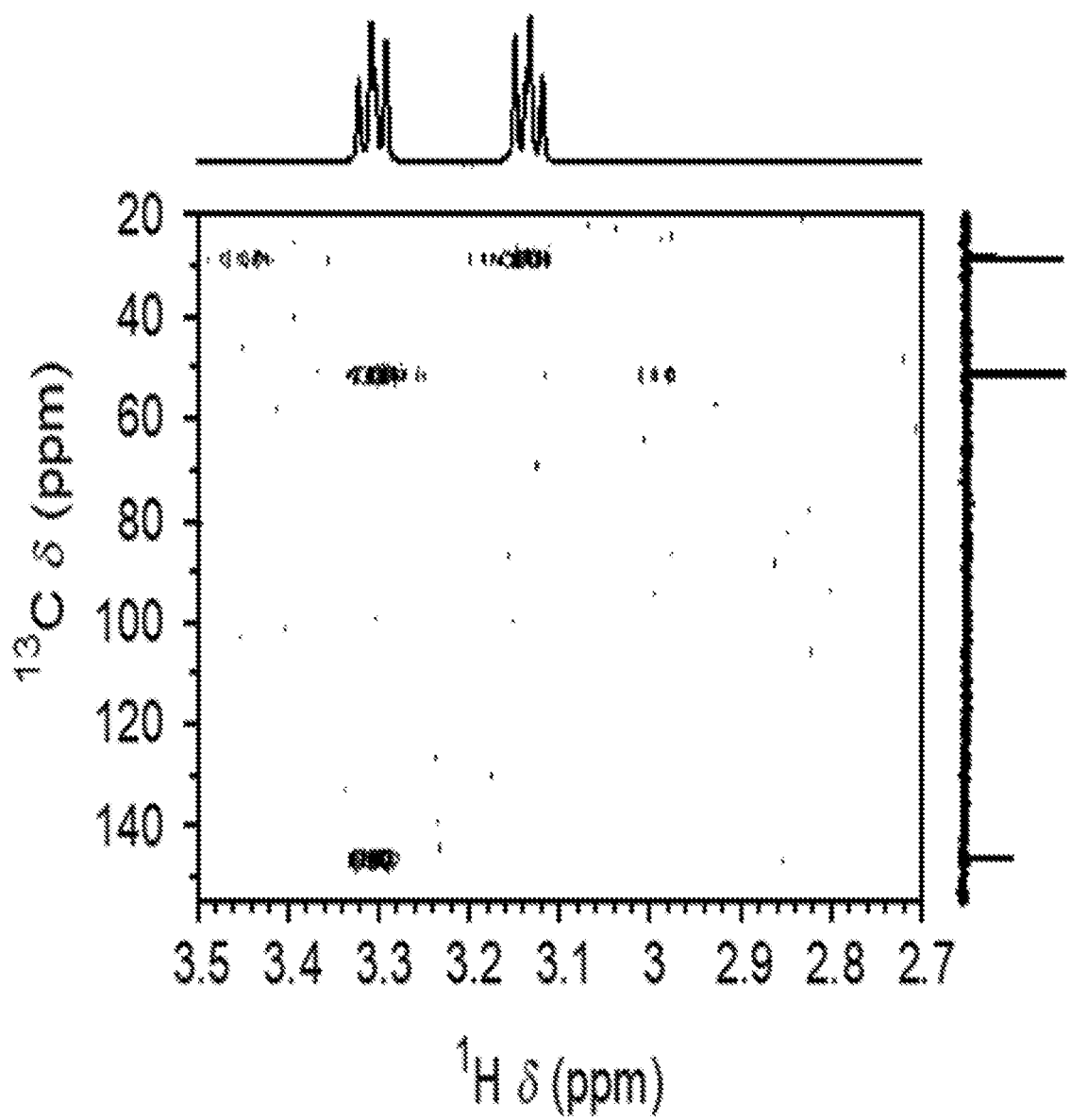

A portion of the product was oxidized to the corresponding quinone, and a $^1$H-$^{13}$C HMBC spectrum establishes that the thioether linkage remained intact (see FIGS. 18A and 18B).

Figure 19:
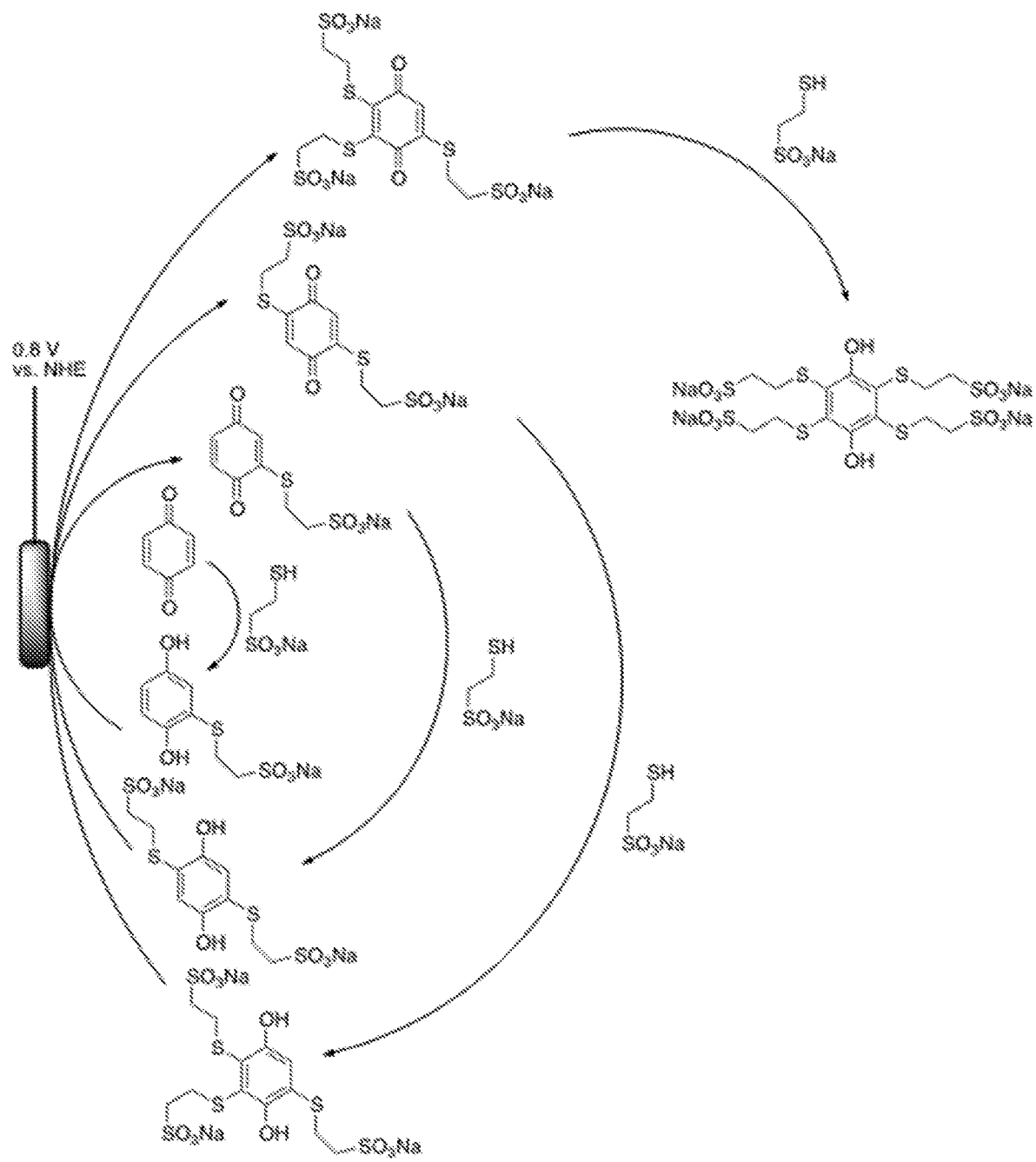
FIG. 19 is a synthesis scheme illustrating method 3 (sequential electrolysis) for making the 2,3,5,6-tetrakis(ethylsulfanyl-2'-sulfonate)-1,4-hydroquinone tetrasodium salt product from the sodium 2-mercaptoethanesulfonate (MESNA) reactant. Multiple sequential oxidations occur as the quinone forms a multiply substituted thioether. As the synthesis proceeds and thioether groups are installed onto the unsubstituted carbons, the quinone core becomes less susceptible to hydrolysis. The quinone core of the final product cannot hydrolyze.
Figure 20:
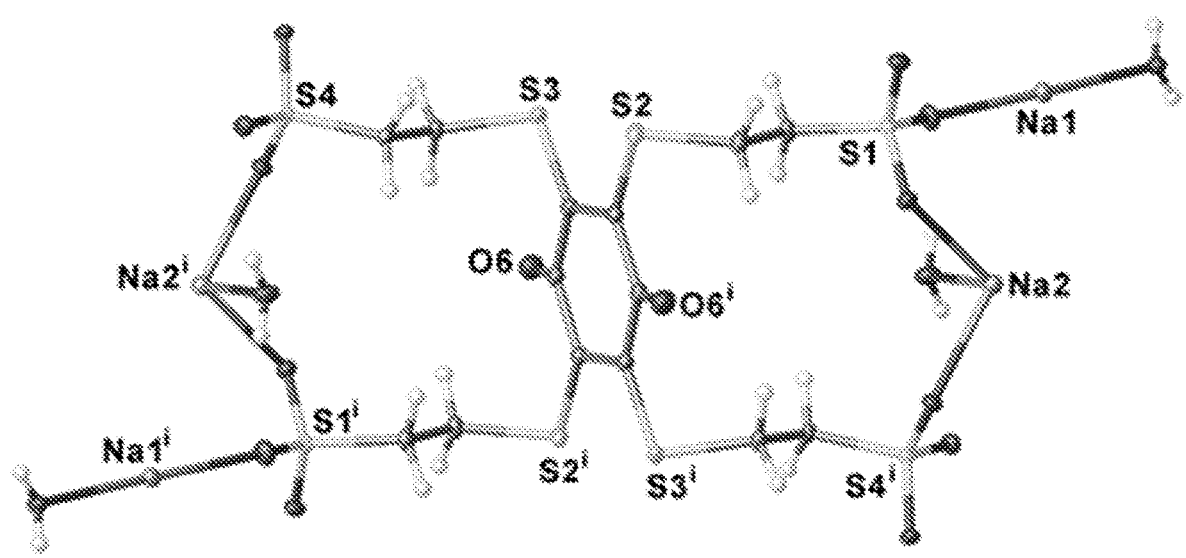
FIG. 20 is a molecular drawing of the partially grown structure of the quinone formed by oxidation of tetrasodium 2,3,5,6-tetrakis(ethylsulfanyl-2'-sulfonate)-1,4-hydroquinone based on single-crystal X-ray diffraction data (having two asymmetric units), shown with 50% probability ellipsoids.

Method 3:

In this method, benzoquinone reacts with MESNA to form an adduct. The adduct is then oxidized electrochemically in the presence of further MESNA at a potential where MESNA does not oxidize readily to its disulfide. The process repeats during the electrolysis until all four thioethers are installed (Scheme 30, illustrated in FIG. 19). As seen in FIG. 19, sequential oxidation occurs as the quinone forms the thioether intermediates and final product, the core of which cannot hydrolyze.

A 432 mg portion of benzoquinone was wetted with 1 ml of ethanol in a single-compartment electrosynthesis cell. To this, 2.630 g of MESNA in 10 ml of water was added, being rinsed into the cell with an additional 2 ml of water. 0.3 ml of 1 M aqueous sulfuric acid was added and the mixture was stirred until the benzoquinone had dissolved.

A reticulated vitreous carbon anode, a platinum wire cathode, and an Ag/AgCl reference electrode were then introduced into the cell and the mixture was electrolyzed at 0.8 V vs. NHE until the solution displayed a persistent brown color. During the electrolysis, the mixture was not stirred except by the hydrogen bubbles produced at the cathode.

The reaction mixture was transferred to a beaker and diluted with 40 ml of ethanol. The precipitate was allowed to flocculate overnight before being filtered. The solids were rinsed twice with ethanol and allowed to dry. In this manner, 3.152 g of 2,3,5,6-tetrakis(ethylsulfanyl-2'-sulfonate)-1,4-hydroquinone tetrasodium salt were obtained in substantially pure form containing traces of ethanol and some of the corresponding quinone.

In a separate run of this method, the current was allowed to flow for a longer time. This led to oxidation of more of the product hydroquinone to the quinone. Using the same workup method outlined above, except for allowing the precipitate to stand for two days before filtering, crystals of the pure quinone form of 2,3,5,6-tetrakis(ethylsulfanyl-2'-sulfonate)-1,4-hydroquinone tetrasodium salt were formed. These crystals were subjected to analysis by x-ray diffraction, and yielded a structure in accord with our expectations (see FIG. 9). It is interesting to note that the product crystallizes as a trihydrate, which may explain the apparently-high mass obtained above.

Example 19—Synthesis of an Exemplary Hydroquinone Substituted with Three Thioether Sulfonates: 2,3,5-tris(ethylsulfanyl-2'-sulfonate)-1,4-hydroquinone trisodium salt Method 2:

A 109 mg portion of benzoquinone was suspended in 0.5 ml of ethanol and 9.4 ml of water plus 0.1 ml of 1 M aqueous sulfuric acid was added. Separately, 0.165 g of MESNA was dissolved in 2 ml of water. The benzoquinone solution was heated to 45° C. and maintained at that temperature. The MESNA solution was added to it dropwise over 15 minutes and allowed to stir under nitrogen for 1 hour. A 110 mg portion of benzoquinone was added and allowed to react for 1 hour.

In this style, 169 mg, 172 mg, and 170 mg portions of MESNA dissolved in 2 ml portions of water were added and allowed to react, alternating with two 108 mg portions of benzoquinone. The reaction mixture was then allowed to stir and cool slowly over night.

The reaction mixture was extracted with 6 ml of ethyl acetate, treated with NaHSO$_3$, and extracted with three 6 ml portions of ethyl acetate. To the resulting aqueous phase was added 50 ml of ethanol and the mixture heated to flocculate the precipitate. After cooling, the solids were filtered and rinsed with ethanol to give 167 mg of 2,3,5,6-tetrakis(ethylsulfanyl-2'-sulfonate)-1,4-hydroquinone tetrasodium salt. On standing, the filtrate gave a second crop of 11 mg of 2,3,5,6-tetrakis(ethylsulfanyl-2'-sulfonate)-1,4-hydroquinone tetrasodium salt.

Figure 21:
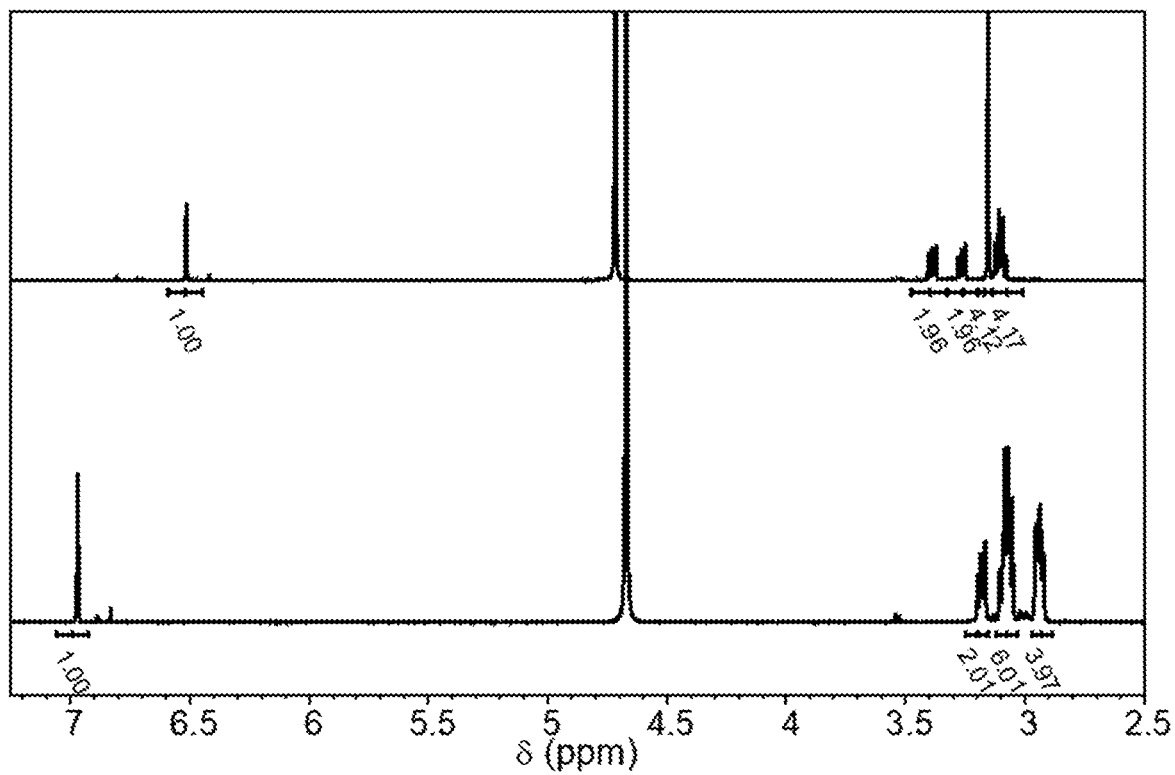
FIG. 21 shows $^1$H NMR spectra of 2,3,5-tris(ethylsulfanyl-2'-sulfonate)-1,4-hydroquinone trisodium salt (lower trace) and its quinone form (upper trace), as made by method 1.

The filtrate was then rotovapped to ~10 ml volume and 35 ml of ethanol were added to form a precipitate. After heating and cooling, the precipitate was filtered and rinsed with ethanol to give 0.521 g of 2,3,5-tris(ethylsulfanyl-2'-sulfonate)-1,4-hydroquinone trisodium salt. A second crop of 44 mg was then formed. NMR spectra are consistent with the proposed structure (see FIG. 21, lower trace). On oxidation, the corresponding quinone is formed (see FIG. 21, upper trace).

Example 20—Synthesis of an Exemplary Hydroquinone Substituted with One Thioether Sulfonate: 2-(ethylsulfanyl-2'-sulfonate)-1,4-hydroquinone sodium salt Method 1:

A 216 mg portion of benzoquinone was dissolved in 10 ml of 1:1 ethanol:water and loaded into a syringe. A 328 mg portion of MESNA was dissolved in 10 ml of 1:1 ethanol:water and loaded into a syringe. The syringes were loaded into a syringe pump and simultaneously discharged at 5 ml/minute into a 9" pipette to drain into a 30 ml shot glass.

Figure 22A:
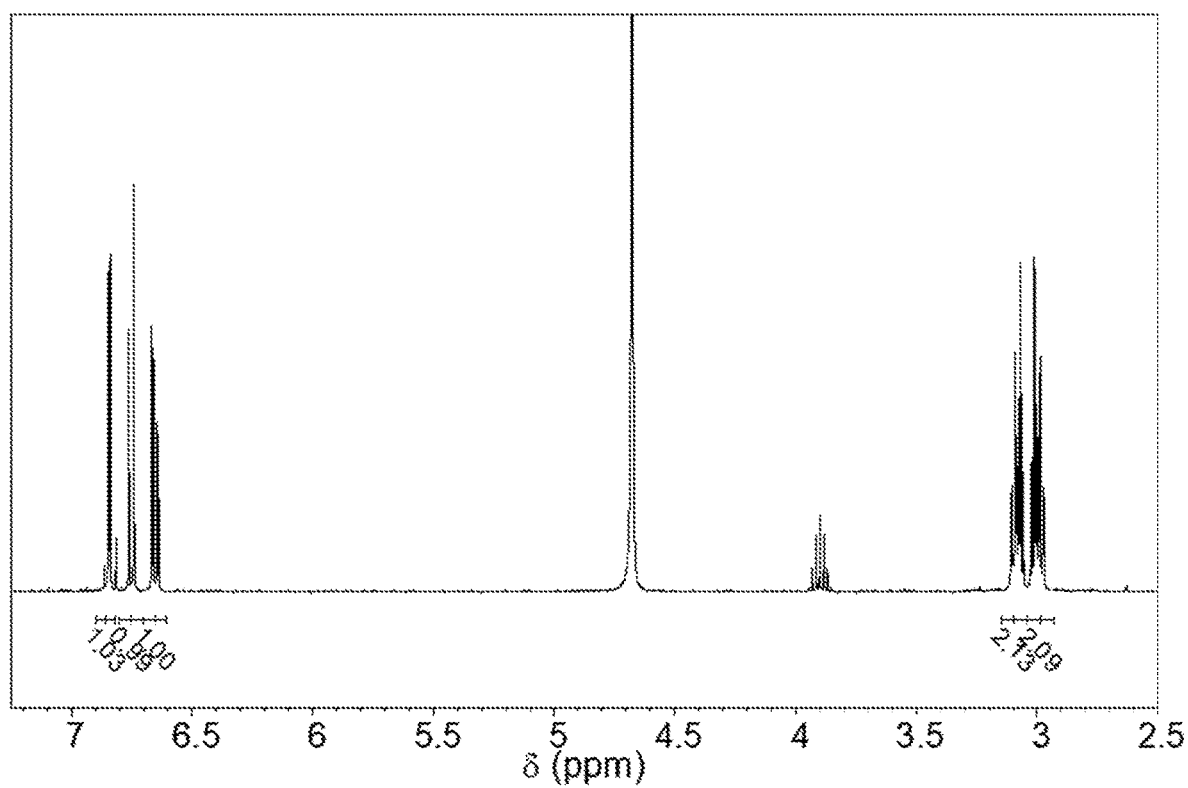
FIGS. 22A and 22B show (22A) $^1$H and (22B) $^{13}$C NMR spectra of 2-(ethylsulfanyl-2'-sulfonate)-1,4-hydroquinone sodium salt, as made by method 1.
Figure 22B:
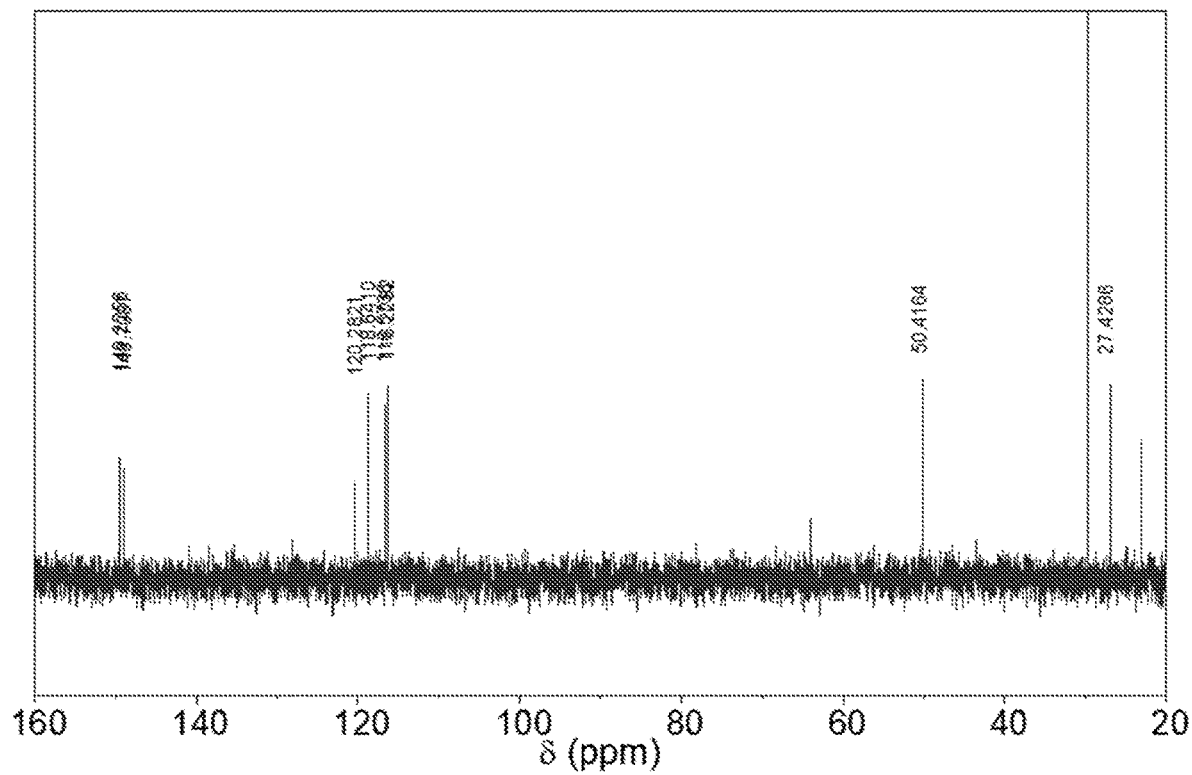

After standing for several days, the mixture was rotovapped and treated with NaHSO$_3$. Ten ml of ethanol were added to the mixture and the resulting solid was filtered off. The filtrate was rotovapped to give 553 mg of material. This was then recrystallized from acetone/water to give pure 2-(ethylsulfanyl-2'-sulfonate)-1,4-hydroquinone sodium salt, with NMR spectra in accord with the proposed structure (See FIGS. 22A and 22B).

Example 21—Synthesis of a Second Exemplary Hydroquinone Substituted with Four Thioether Sulfonates: 2,3,5,6-tetrakis(propylsulfanyl-3'-sulfonate)-1,4-hydroquinone tetrasodium salt Method 3:

To 1.509 g of benzoquinone in 5 ml of ethanol, 50 ml of water were added. With stirring, 9.951 g of sodium 3-mercapto-1-propanesulfonate were added, followed by 0.3 ml of aqueous 1 M H$_2$SO$_4$. After stirring until almost all of the solids were consumed, a reticulated vitreous carbon anode and a nickel wire cathode were inserted into the solution. Without stirring, the solution was electrolyzed at a constant current of 0.029 A until 6549 coulombs of charge had been passed. At this point, the solution was observed to be a coffee-like brown color that persisted when the flow of current was halted.

The electrodes were removed and rinsed into the solution with a minimal amount of water. The reaction mixture was diluted with 300 ml of ethanol, added in small portions with swirling. After the first 200 ml of ethanol were added, the mixture had a sandy color and porridge-like consistency. Following the addition of the ethanol, the mixture was allowed to stand for one hour. The solids were then filtered and rinsed with two 30 ml portions of ethanol and allowed to dry to give 10.769 g (13.22 mmol, 95% yield) of a cream-colored solid.

Figure 23:
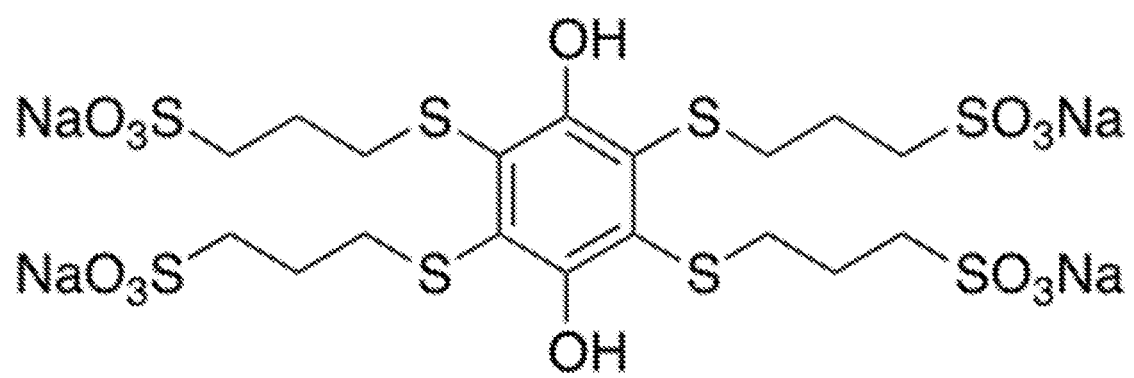
FIG. 23 shows the chemical structure of 2,3,5,6-tetrakis(propylsulfanyl-3'-sulfonate)-1,4-hydroquinone tetrasodium salt.
Figure 24A:
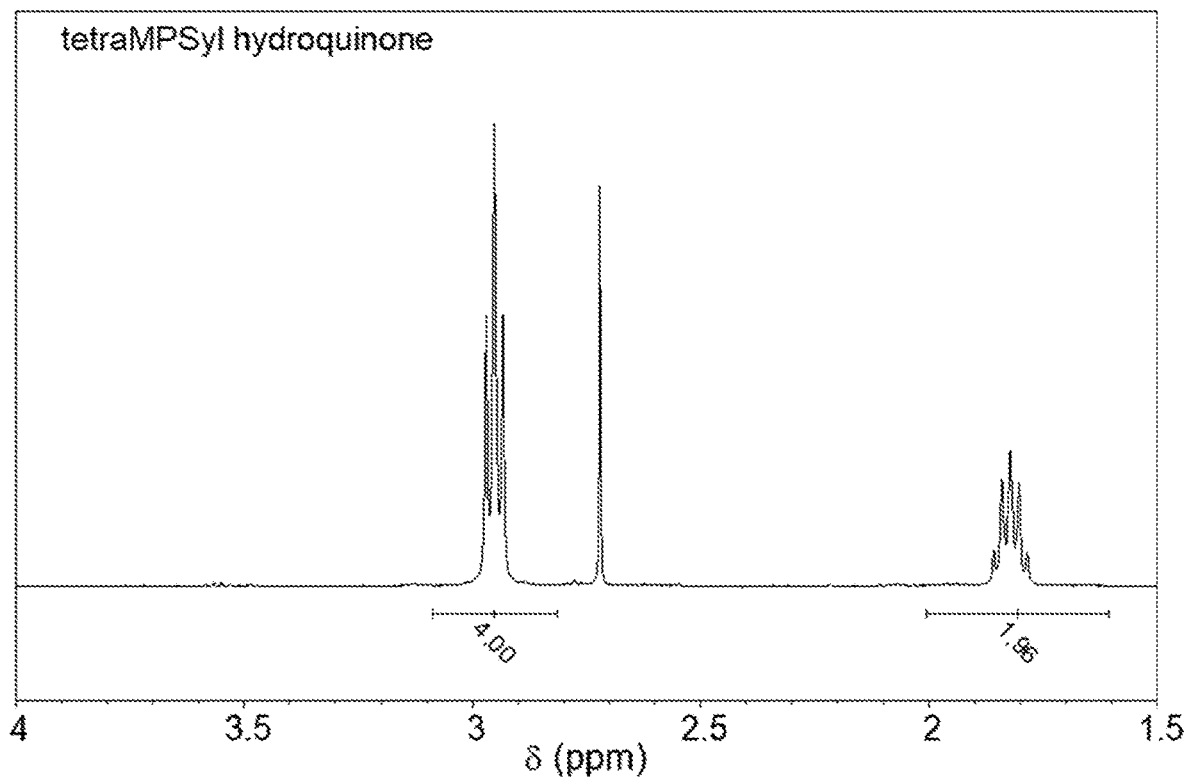
FIGS. 24A and 24B show (24A)$^1$H and (24B) $^{13}$C NMR spectra of 2,3,5,6-tetrakis(propylsulfanyl-3'-sulfonate)-1,4-hydroquinone tetrasodium salt product, as made by method 3 (sequential electrolysis).
Figure 24B:
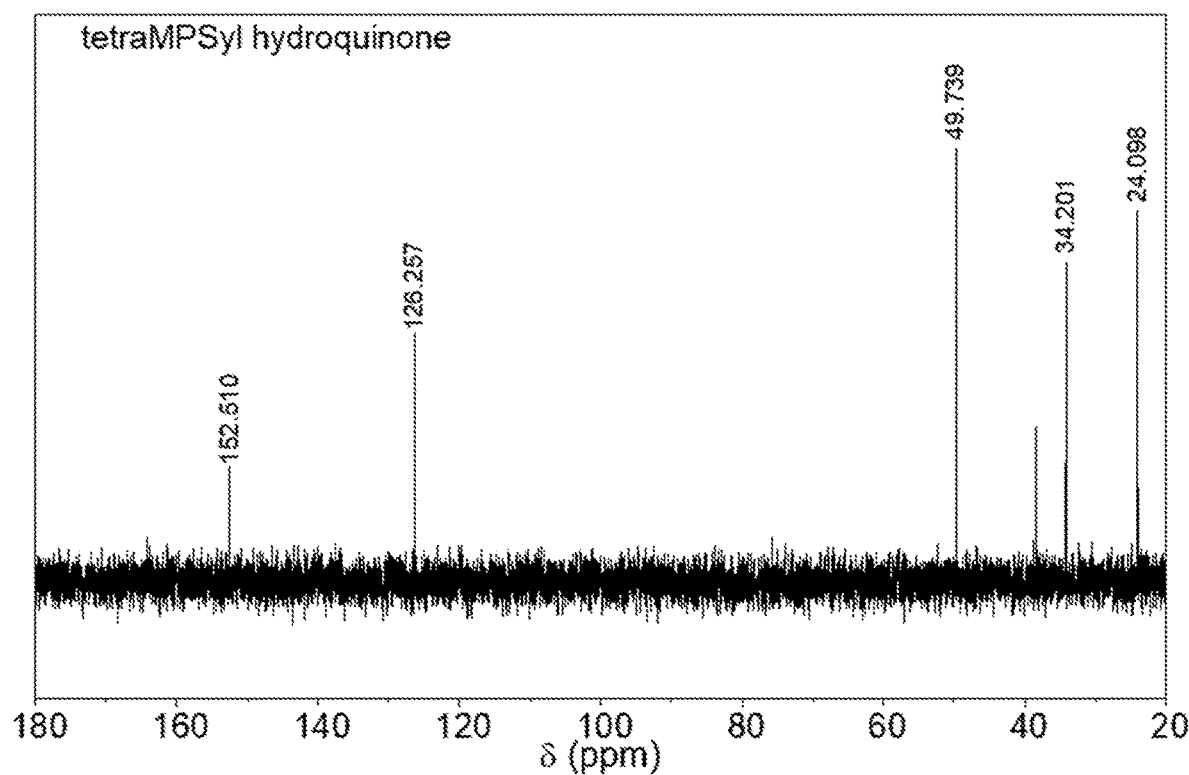
Figure 24C:
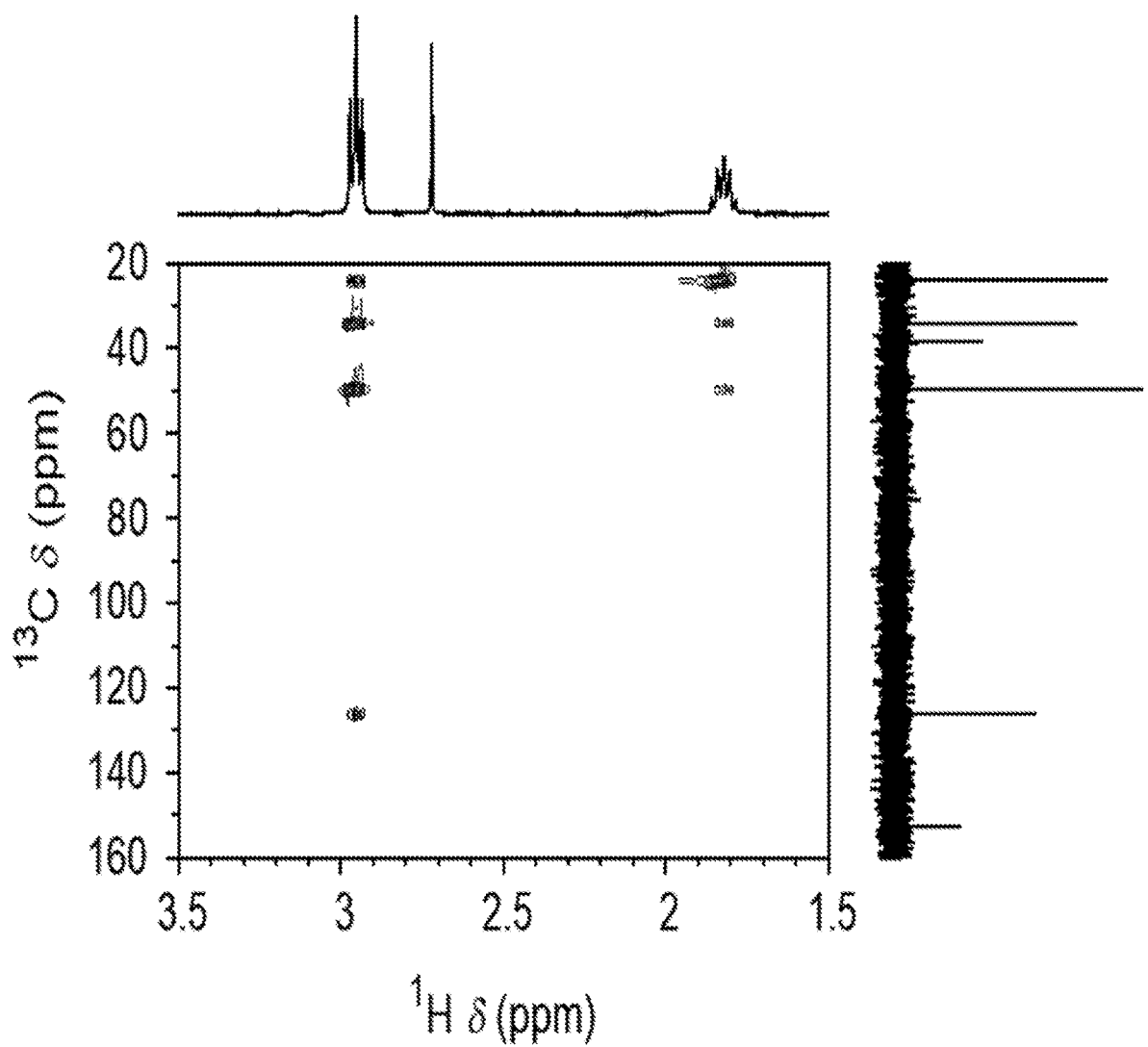
FIG. 24C shows a combined $^1$H-$^{13}$C HSQC (in blue) and HMBC (in red/black) spectrum of 2,3,5,6-tetrakis(propylsulfanyl-3'-sulfonate)-1,4-hydroquinone tetrasodium salt product, as made by method 3 (sequential electrolysis).

NMR spectroscopy confirmed that this substance is 2,3,5,6-tetrakis(propylsulfanyl-3'-sulfonate)-1,4-hydroquinone tetrasodium salt, which has the chemical structure shown in FIG. 23 (see FIGS. 24A, 24B and 24C).

Example 22—Oxidation of the Exemplary Hydroquinone of Example 21 to Form an Exemplary Benzoquinone Substituted with Four Thioether Sulfonates: 2,3,5,6-tetrakis(propylsulfanyl-3'-sulfonate)-1,4-benzoquinone tetrasodium salt To 0.822 g of 2,3,5,6-tetrakis(propylsulfanyl-3'-sulfonate)-1,4-hydroquinone tetrasodium salt, 9 ml of water were added in a roundbottom flask with a stirbar. The resulting solution was cooled in an ice-bath and 76 mg of sodium nitrite were added. Then 1 ml of 1 M aqueous nitric acid was added. The solution promptly turned black and gas was evolved. This mixture was allowed to stir and warm to room temperature over 10 minutes. At that time, 20 ml of ethanol was added, leading to a dark precipitate which was allowed to stand for 15 minutes.

Figure 25:
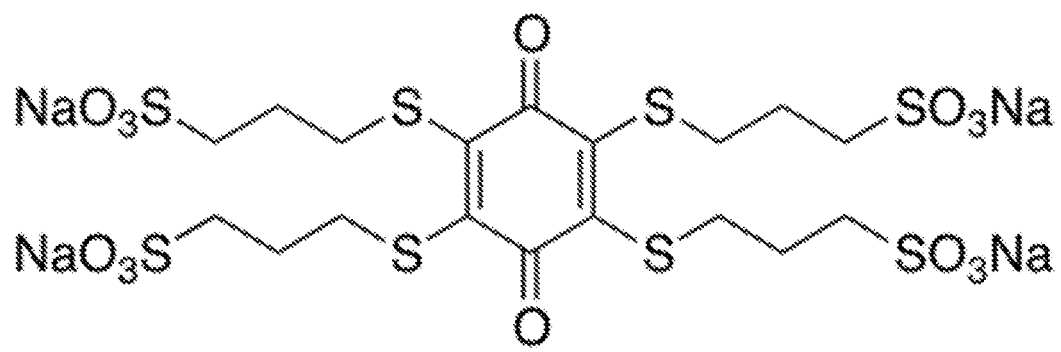
FIG. 25 shows the chemical structure of 2,3,5,6-tetrakis(propylsulfanyl-3'-sulfonate)-1,4-benzoquinone tetrasodium salt.
Figure 26A:
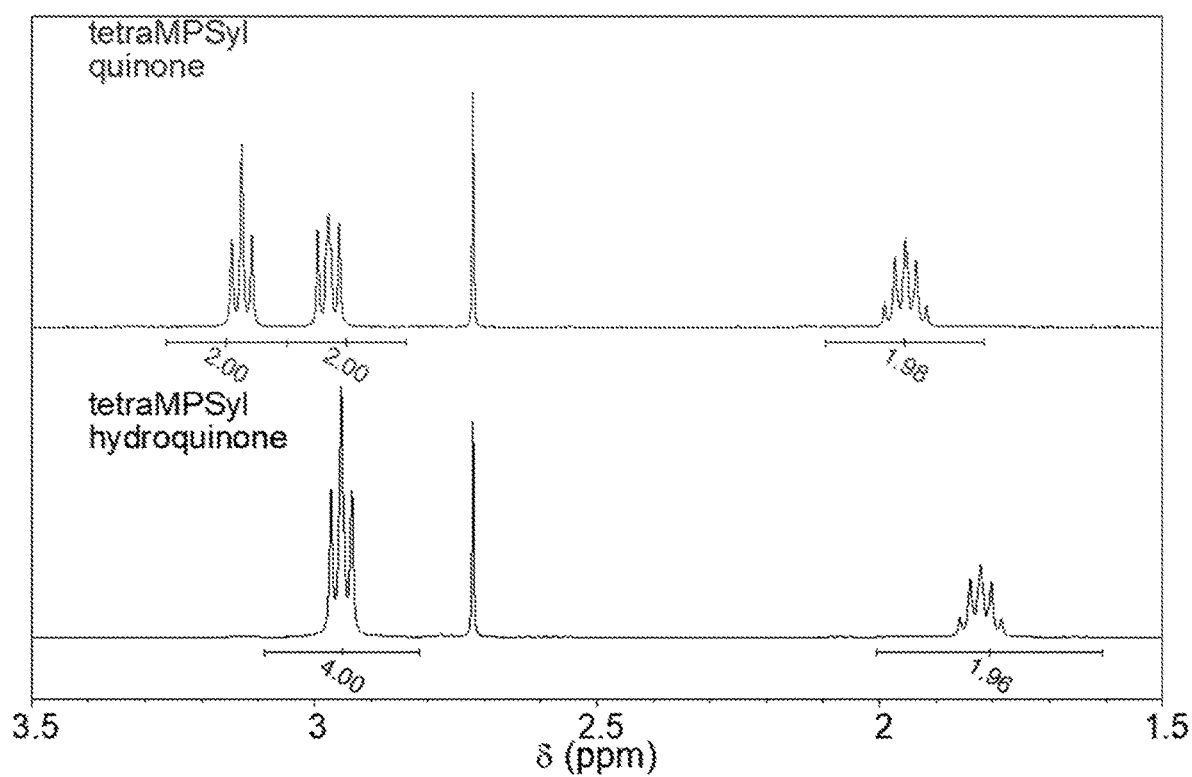
FIGS. 26A and 26B show (26A)$^1$H and (26B) $^{13}$C NMR spectra of the 2,3,5,6-tetrakis(propylsulfanyl-3'-sulfonate)-1,4-benzoquinone tetrasodium salt, as produced by chemically oxidizing the 2,3,5,6-tetrakis(propylsulfanyl-3'-sulfonate)-1,4-hydroquinone tetrasodium salt made by method 3.
Figure 26B:
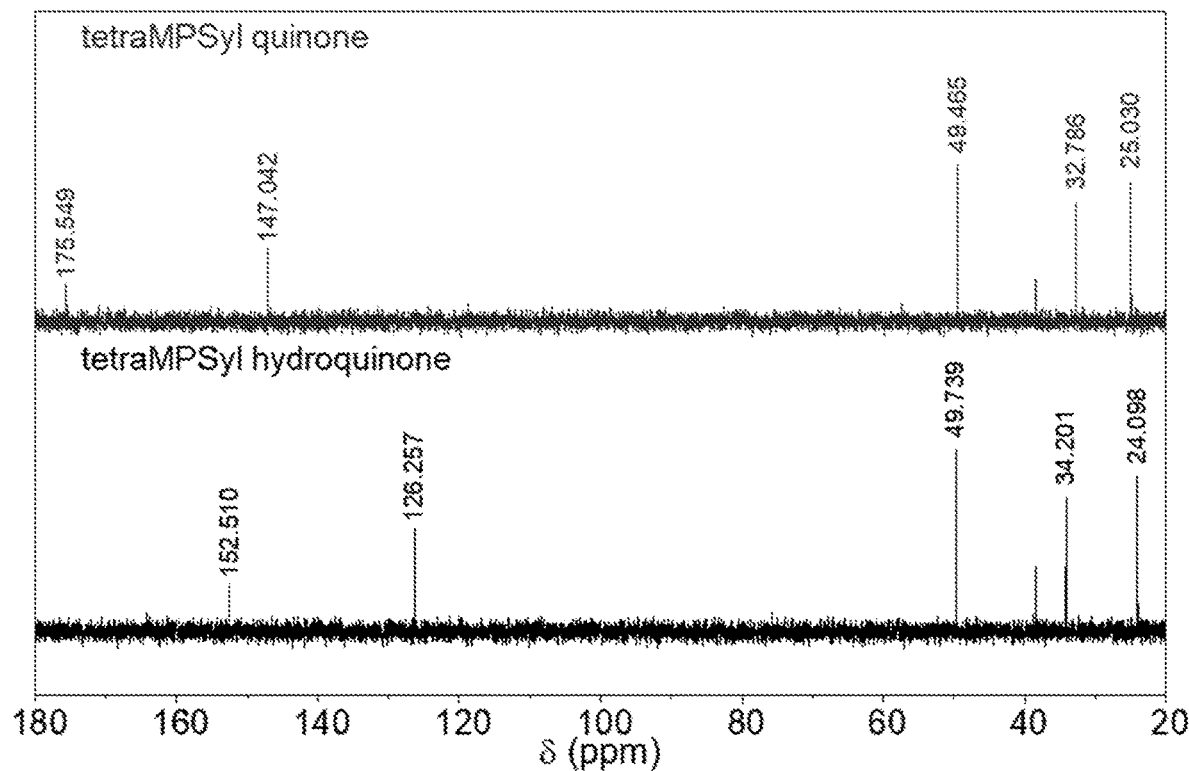
Figure 26C:
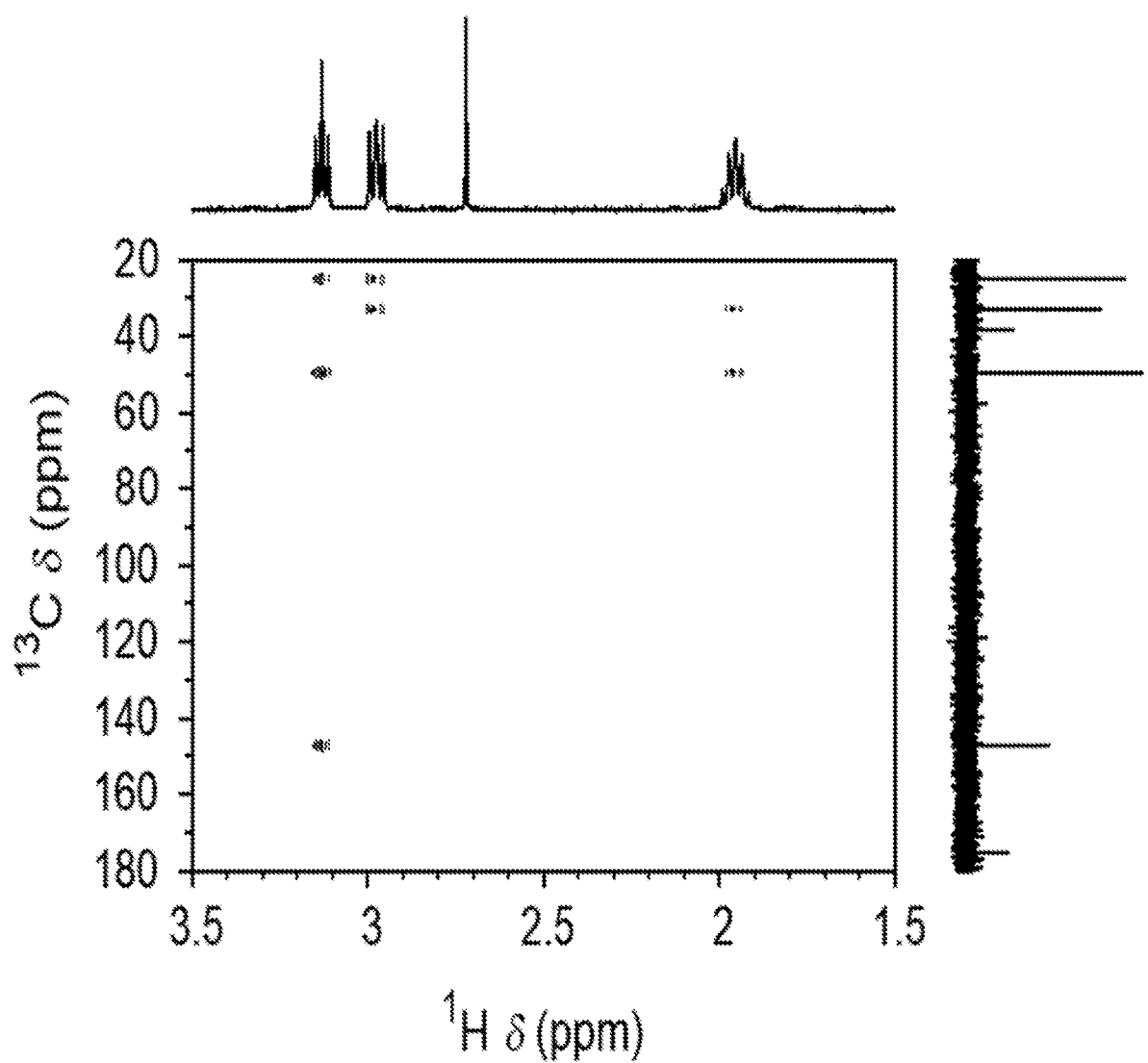
FIG. 26C shows a $^1$H-$^{13}$C HMBC spectrum of the 2,3,5,6-tetrakis(propylsulfanyl-3'-sulfonate)-1,4-benzoquinone tetrasodium salt that was produced by chemically oxidizing the 2,3,5,6-tetrakis(propylsulfanyl-3'-sulfonate)-1,4-hydroquinone tetrasodium salt made by method 3.

The solids were filtered and rinsed with a mixture of 5 ml ethanol and 1 ml water followed by 5 ml of ethanol and then allowed to dry to give 0.564 g of a dark brown mass (0.69 mmol, 69%). NMR spectra confirmed the oxidation product to be 2,3,5,6-tetrakis(propylsulfanyl-3'-sulfonate)-1,4-benzoquinone tetrasodium salt, which has the chemical structure shown in FIG. 25 (see FIGS. 26A, 26B and 26C).

Example 23—Synthesis of a Second Exemplary Hydroquinone Substituted with One Thioether Sulfonate: 2,3,5-trimethyl-6-(propylsulfanyl-3'-sulfonate)-1,4-hydroquinone sodium salt A 1.571 g portion of trimethyl hydroquinone was wetted with 9 ml of ethanol. To this, 35 ml of water, 0.5 ml of 1 M $H_2SO_4$, and 1.736 g of sodium 3-mercapto-1-propanesulfonate were added and stirred briefly. A reticulated vitreous carbon anode and a platinum wire cathode were inserted into the solution. Without stirring, the solution was electrolyzed at a constant current of 0.040 A until the reaction was complete. Sodium bisulfite was added to reduce the product to the hydroquinone oxidation state. On addition of acetone, the bisulfite adduct formed and was filtered away. The filtrate was concentrated by rotary evaporation and treated again with acetone. At this time, the product separated as a solid and was collected by filtration in several crops to give a total yield of 91%.

Figure 27:
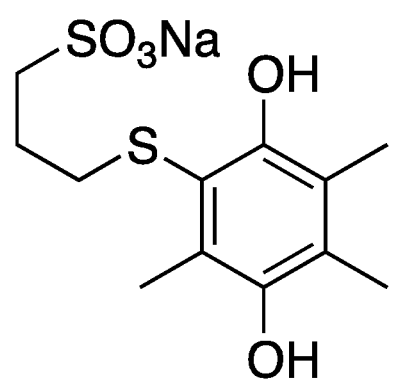
FIG. 27 shows the chemical structure of 2,3,5-trimethyl-6-(propylsulfanyl-3'-sulfonate)-1,4-hydroquinone sodium salt.
Figure 28A:
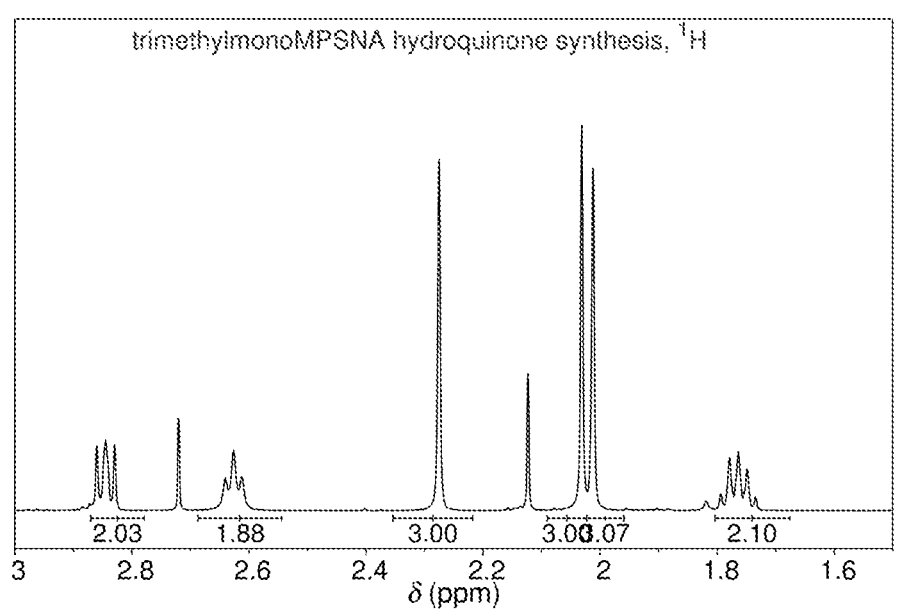
FIGS. 28A and 28B show (28A) $^1$H and (28B) $^{13}$C NMR spectra of 2,3,5-trimethyl-6-(propylsulfanyl-3'-sulfonate)-1,4-hydroquinone sodium salt.
Figure 28B:
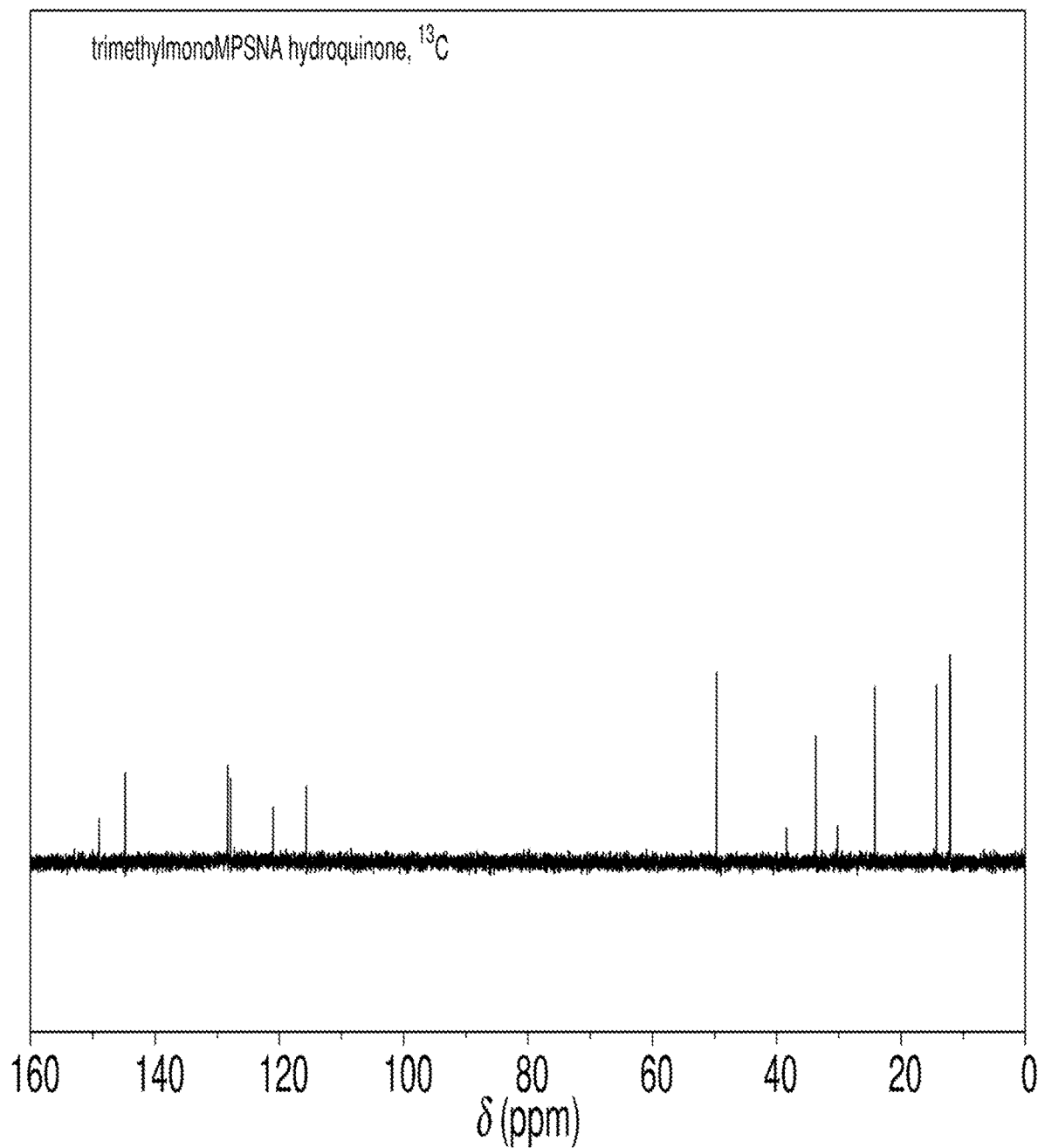
Figure 28C:
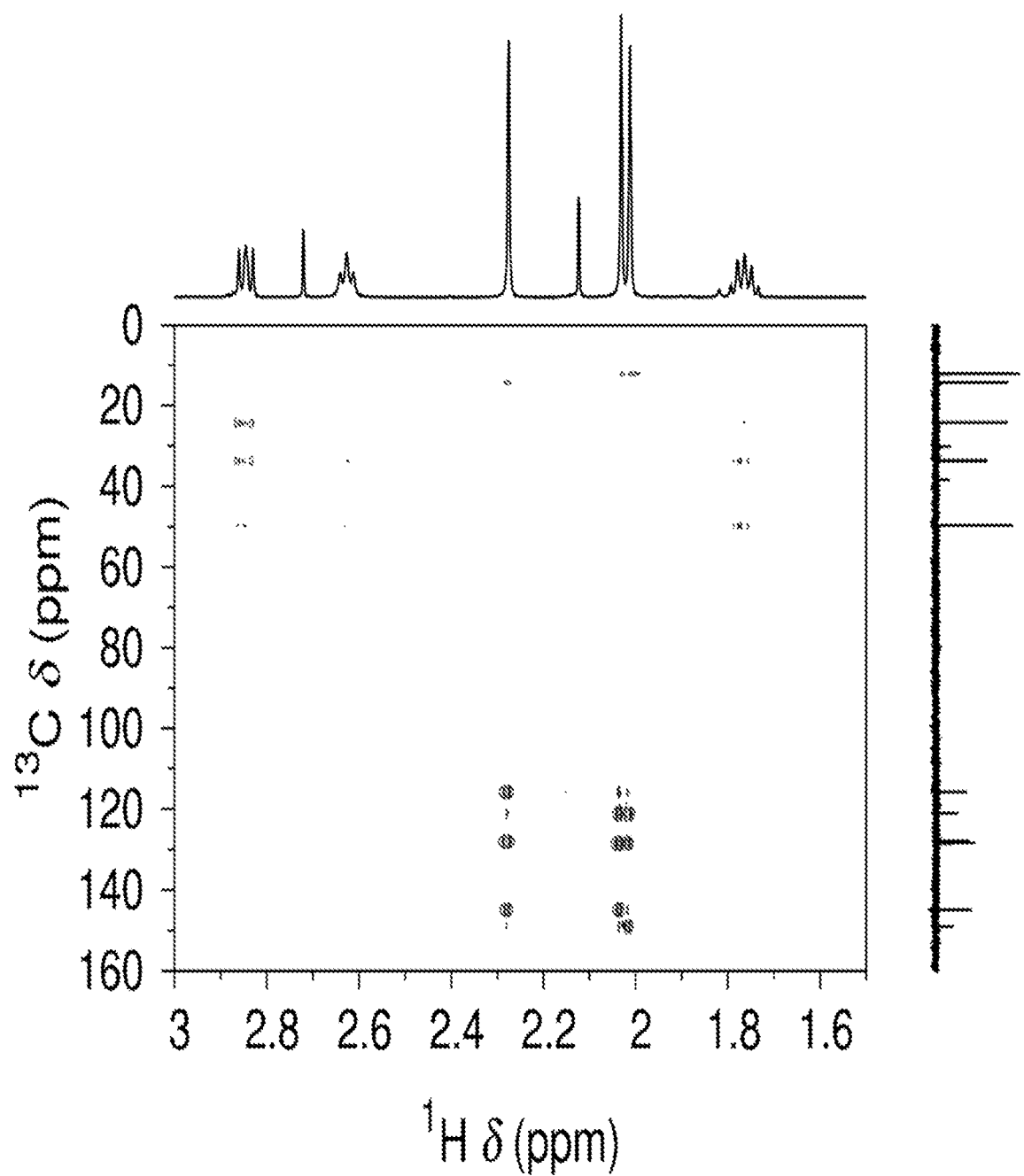
FIG. 28C shows a combined $^1$H-$^{13}$C HSQC (in blue) and HMBC (in red/black) spectrum of 2,3,5-trimethyl-6-(propylsulfanyl-3'-sulfonate)-1,4-hydroquinone sodium salt.

NMR spectroscopy confirmed that this substance is 2,3,5-trimethyl-6-(propylsulfanyl-3'-sulfonate)-1,4-hydroquinone tetrasodium salt, which has the chemical structure shown in FIG. 27 (see FIGS. 28A, 28B and 28C).

While a number of embodiments of the present invention have been described above, the present invention is not limited to just these disclosed examples. There are other modifications that are meant to be within the scope of the invention, which is defined by the appended claims.

REFERENCES CITED

1. Cerfontain, H.; Koeberg-Telder, A. Red. Tray. Chim. Pays-Bas 1988, 107, 583-591.
2. a) Xu, Y.; Wen, Y.; Cheng, J.; Yanga, Y.; Xie, Z.; Cao, G. World Non-Grid-Connected Wind Power and Energy Conference, 2009; b) Rausch, B.; Symes, M. D.; Cronin, L. J. Am. Chem. Soc. 2013, 135, 13656-13659; c) Yang, B.; Hoober-Burkhardt, L.; Wang, F.; Surya Prakash, G. K.; Narayanan, S. R. J. Electrochem. Soc. 2014, 161, A1371-A1380.
3. a) Erdtman, H. G. H. Proc. R. Soc. Ser. A 1933, 143, 177-191; b) Erdtman, H. G. H. Proc. R. Soc. Ser. A 1933, 143, 191-222; c) Erdtman, H. G. H. Proc. R. Soc. Ser. A 1933, 143, 223-228; d) Erdtman, H. G. H. Proc. R. Soc. Ser. A 1933, 143, 228-241; e) Erdtman, H.; Hogberg, H.-E. Tetrahedron 1979, 35, 535-540.
4. a) Xu, Y.; Wen, Y.; Cheng, J.; Yanga, Y.; Xie, Z.; Cao, G. World Non-Grid-Connected Wind Power and Energy Conference, 2009; b) Rausch, B.; Symes, M. D.; Cronin, L. J. Am. Chem. Soc. 2013, 135, 13656-13659; c) Yang, B.; Hoober-Burkhardt, L.; Wang, F.; Surya Prakash, G. K.; Narayanan, S. R. J. Electrochem. Soc. 2014, 161, A1371-A1380.
5. a) Dodgson, J. W. J. Chem. Soc. 1930, 2498-2502; b) Akutsu, H.; Yamada, J.; Nakatsuji, S.; Turner, S. S. CrystEngComm 2009, 11, 2588-2592.
6. a) Er, S.; Suh, C.; Marshak, M.; Aspuru-Guzik, A. Chem. Sci. 2015, 6, 885-893; b) Pineda Flores, S. D.; Martin-Noble, G. C.; Phillips, R. L.; Schrier, J. J. Phys. Chem. C 2015, 119, 21800-21809.
7. Akutsu, H.; Yamada, J.; Nakatsuji, S.; Turner, S. CrystEngComm 2009, 11, 2588-2592.
8. Kobiro, K.; Shi, M.; Inoue, Y. Chem. Lett. 1999, 633-634.
9. Reetz, T. U.S. Pat. No. 2,935,518, May 3, 1960.
10. Houghton, S. R.; Melton, J.; Fortunak, J.; Ripin, D. H. B.; Boddy, C. N. Tetrahedron 2010, 66, 8137-8144.
11. Dokunikhin, N. S.; Gaeva, L. A.; Mezentseva, G. A. Dokl. Akad. Nauk. (engl.) 1972, 206, 750-752.
12. Rathore, R.; Bosch, E.; Kochi, J. K. J. Chem. Soc. Perkin Trans. 2 1994, 1157-1166.
13. Schubert, M. J. Am. Chem. Soc. 1947, 69, 712-713.
14. Dutov, M. D.; Serushkina, O. V.; Shevelev, S. A. Russ. J. Org. Chem. 2007, 43, 1167-1169.
15. a) Nef, J. U. Ann. Chem. 1887, 237, 1-39; b) Nef, J. U. Ann. Chem. 1890, 258, 261-317; c) Lee, S. J.; Jung, J. C.; Lee, S. W.; Ree, M. J. Polym. Sci. A 2004, 42, 3130-3142; d) Suh, D. H.; Chung, E. Y.; Hong, Y.-T.; Choi, K.-Y. Angew. Makromol. Chem. 1998, 254, 33-38; e) Cao, D.; Hong, M.; Blackburn, A. K.; Liu, Z.; Holcroft, J. M.; Stoddart, J. F. Chem. Sci. 2014, 5, 4242-4248; f) Guo, X.; Watson, M. D. Macromolecules 2011, 44, 6711-6716.
16. Thiele, J.; Gunther, F. Ann. Chem. 1906, 349, 45-66.
17. a) Nef, J. U. Ann. Chem. 1887, 237, 1-39; b) Nef, J. U. Ann. Chem. 1890, 258, 261-317.
18. Lee, S. J.; Jung, J. C.; Lee, S. W.; Ree, M. J. Polym. Sci. A 2004, 42, 3130-3142.
19. The starting material, 3,6-dimethoxypyromellitic acid, was prepared from duroquinone.
20. For the reaction of taurine with phthalic anhydride, see: Usifoh, C. O.; Lambert, D. M.; Wouters, J. Scriba, G. K. E. Arch. Pharm. Pharm. Med. Chem. 2001, 334, 323-331.
21. Suh, D. H.; Chung, E. Y.; Hong, Y.-T.; Choi, K.-Y. Angew. Makromol. Chem. 1998, 254, 33-38.
22. Cao, D.; Hong, M.; Blackburn, A. K.; Liu, Z.; Holcroft, J. M.; Stoddart, J. F. Chem. Sci. 2014, 5, 4242-4248.
23. Guo, X.; Watson, M. D. Macromolecules 2011, 44, 6711-6716.
24. Jacob III, P.; Callery, P. S.; Shulgin, A. T.; Castagnoli Jr., N. J. Org. Chem. 1976, 41, 3627-3629.
25. Thiele, J.; Gunther, F. Ann. Chem. 1906, 349, 45-66.
26. Xiong, B.; Shen, R.; Goto, M. Yin, S.-F.; Han, L.-B. Chem. Eur. J. 2012, 18, 16902-16910.
27. Ilchenko, N. O.; Janson, P. G.; Szab, K. J. Chem. Commun. 2013, 49, 6614-6616.
28. Hünig, S.; Bau, R.; Kemmer, M.; Meixner, H.; Metzenthin, T.; Peters, K.; Sinzger, K.; Gulbis, J. Eur. J. Org. Chem. 1998, 335-348.
29. Abdou, W. M.; Salem, M. A. I.; Sediek, A. A. J. Chem. Res. (S) 1998, 28-29.
30. Nielsen, A. T.; Carpenter, W. R. Org. Syn. 1965, 45, 25.
31. Curtin, D. Y.; Byrn, S. R. J. Am. Chem. Soc. 1969, 91, 6102-6106.
32. Hintermann, L.; Suzuki, K. Synthesis 2008, 2303-2306.
33. Hogberg, T.; Strom, P.; Ebner, M.; Ramsby, S. J. Org. Chem. 1987, 52, 2033-2036.
34. Lin, H.; Huang, Y.-D.; Wang, F. Int. J. Mol. Sci. 2008, 9, 2159-2168.

35. a) Catalan, J.; Fabero, F.; Guijarro, M. S.; Claramunt, R. M.; Santa Maria, M. D.; de la Concepcion Foces-Foces, M.; Cano, F. H.; Elguero, J.; Sastre, R. J. Am. Chem. Soc. 1990, 112, 747-759; b) Ballesteros, P; Claramunt, R. M.; Escolástico, C.; Santa Maria, M. D. J. Org. Chem. 1992, 57, 1873-1876.

36. GauB, W.; Heitzer, H.; Petersen, S. Liebigs Ann. Chem. 1972, 764, 131-144.

37. Rondestvedt Jr., C. S.; Chang, P. K. J. Am. Chem. Soc. 1955, 77, 6532-6540.

38. Brownbridge, P.; Chan, T.-H. Tet. Lett. 1980, 21, 3423-3426.

39. Barbero, M.; Bazzi, S.; Cadamuro, S.; Dughera, S.; Magistris, C.; Venturello, P. Synlett 2010, 1803-1806.

40. Russell, G. N.; Suleman, N. K.; Iwamura, H.; Webster, O. W. J. Am. Chem. Soc. 1981, 103, 1560-1561.

41. Strutt, N. R.; Zhang, H.; Schneebeli, S. T.; Stoddart, J. F. Acc. Chem. Res. 2014, 47, 2631-2642.

42. Sevenard, D. V.; Kazakova, O.; Schoth, R.-M.; Lork, E.; Chizhov, D. L.; Poveleit, J.; Roschenthaler, G.-V. Synthesis 2008, 12, 1867-1878.

43. Dost, N. Red. Tray. Chim. Pays-Bas Belg. 1952, 71, 857-868.

44. Kehayoglou, A. H.; Sideridou-Karayannidou, I.; Karayannidis, G. P. J. Polym. Sci. 1985, 23, 2803-2818.

45. Suter, C. M.; Bair, R. K.; Bordwell, F. G. J. Org. Chem. 1945, 10, 470-478.

46. Norton, C. J.; Seppi, N. F.; Reuter, M. J. J. Org. Chem. 1968, 33, 4158-4165.

47. Huang, J.; Shkrob, I. A.; Wang, P.; Cheng, L.; Pan, B.; He, M.; Liao, C.; Zhang, Z.; Curtiss, L. A.; Zhang, L. J. Mater. Chem. A, 2015, 3, 7332-7337.

48. Matsubara, H.; Maegawa, T.; Kita, Y.; Yokoji, T.; Nomoto, A. Org. Biomol. Chem. 2014, 12, 5442-5447.

49. a) Meschkat, E.; Barratt, M. D.; Lepoittevin, J.-P. Chem. Res. Toxicol. 2001, 14, 110 117. b) Baimuratov, M. R.; Leonova, M. V.; Rybakov, V. B.; Klimochkin, Y. N. Chem. Heterocyc. Comp. 2015, 51, 582-585. c) Leonova, M. V.; Baimuratov, M. R.; Klimochkin, Y. N. Russ. J. Org. Chem. 2017, 53, 326-334.

50. Petrov, V. A.; Krespan, C. G. J. Org. Chem. 1996, 61, 9605-9607.

51. a) Volkov, N. D.; Nazaretian, V. P.; Yagupol'skii, L. M. Synthesis, 1979, 12, 972-975. b) Dolbier, W. R., Jr.; Tian, F.; Duan, J.-X.; Li, A.-R.; Ait-Mohand, S.; Bautista, O.; Buathong, S.; Baker, J. M.; Crawford, J.; Anselme, P.; Cai, X. H.; Modzelewska, A.; Koroniak, H.; Battiste, M. A.; Chen, Q.-Y. J. Fluorine Chem. 2004, 125, 459-469.

52. Nematollahi, D.; Rafiee, M.; Fotouhi, L. J. Iran. Chem. Soc. 2009, 6, 448-4 76, and references cited therein.

53. a) Phillips, M. Chem. Rev. 1929, 6, 157-174. b) Socha, A. Dyes and Pigments, 1990, 12, 213-218. c) Gerhardt, M. R.; Beh, E. S.; Tong, L.; Gordon, R. G.; Aziz, M. J. MRS Advances, 2017, 2, 431-438.

54. a) Reid, E. E.; Mackall, C. M.; Miller, G. E. J. Am. Chem. Soc. 1921, 43, 2104-2117. b) Hoffman, W. S.; Reid, E. E. J. Am. Chem. Soc. 1923, 45, 1831-1838. c) Peters, A. T.; Tenny, B. A. J. Soc. Dyers Colour, 1977, 93, 373-378. d) Song, Z.; Zhan, H.; Zhou, Y. Chem. Commun. 2009, 448-450.

We claim:

1. A substituted hydroquinone having the formula:

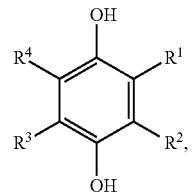

wherein one, two, three, or all four of $R^1$, $R^2$, $R^3$ and $R^4$ comprise a thioether moiety and a sulfonate moiety, and wherein each $R^1$, $R^2$, $R^3$ and $R^4$ that does not comprise a thioether and a sulfonate moiety is independently a hydrogen, an alkyl, or an electron withdrawing group; or the oxidized form (the substituted 1,4-benzoquinone form) of said substituted hydroquinone.

2. The substituted hydroquinone or benzoquinone of claim 1, wherein each of the one, two, three, or four of $R^1$, $R^2$, $R^3$ and $R^4$ that comprise a thioether moiety and a sulfonate moiety independently has the chemical structure $S(CH_2)_n SO_3^-$, wherein n is 1, 2, 3 or 4.

3. The substituted hydroquinone or benzoquinone of claim 1, wherein one of $R^1$, $R^2$, $R^3$ and $R^4$ comprises a thioether moiety and a sulfonate moiety, and wherein the $R^1$, $R^2$, $R^3$ and $R^4$ that do not comprise a thioether and a sulfonate moiety are independently a hydrogen, an electron withdrawing group, or an alkyl.

4. The substituted hydroquinone or benzoquinone of claim 1, wherein three or all four of $R^1$, $R^2$, $R^3$ and $R^4$ comprise a thioether moiety and a sulfonate moiety.

5. The substituted hydroquinone or benzoquinone of claim 4, wherein three of $R^1$, $R^2$, $R^3$ and $R^4$ comprise a thioether moiety and a sulfonate moiety, and wherein the $R^1$, $R^2$, $R^3$ and $R^4$ that does not comprise a thioether and a sulfonate moiety is an electron withdrawing group or an alkyl.

6. The substituted hydroquinone or benzoquinone of claim 1, wherein the electron withdrawing group is selected from the group consisting of nitrile (cyanide), an amide, a ketone, —$CF_3$, —$SF_5$, an imide, an imidazole, a benzimidazole, an oxazole, a benzoxazole, a thiazole, a benzthiazole, and a pyrazole.

7. The substituted hydroquinone or benzoquinone of claim 4, wherein all four of $R^1$, $R^2$, $R^3$ and $R^4$ comprise a thioether moiety and a sulfonate moiety.

8. The substituted hydroquinone or benzoquinone of claim 1, wherein the hydroquinone form is selected from the group consisting of:

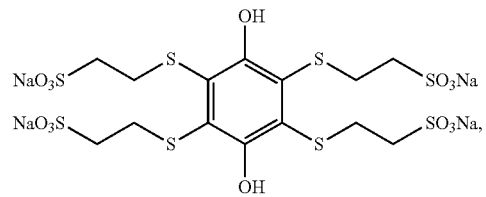

-continued

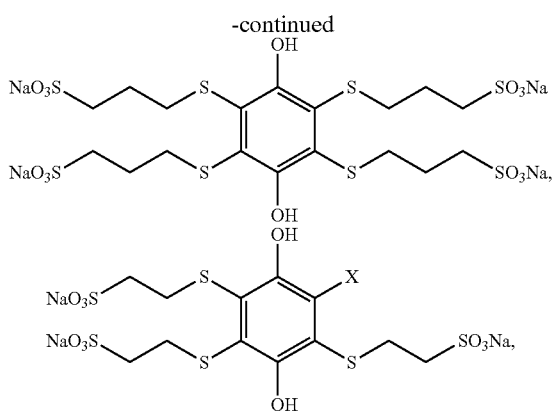

wherein X is a hydrogen, an electron withdrawing group, or an alkyl; and

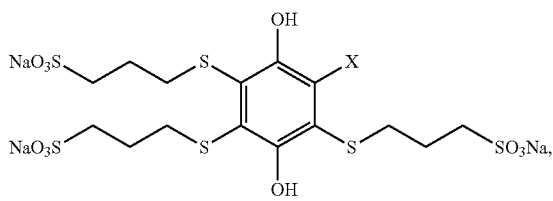

wherein X is a hydrogen, an electron withdrawing group, or an alkyl.

9. The substituted hydroquinone or benzoquinone of claim 8, wherein the electron withdrawing group is selected from the group consisting of nitrile (cyanide), an amide, a ketone, —$CF_3$, —$SF_5$, an imide, an imidazole, a benzimidazole, an oxazole, a benzoxazole, a thiazole, a benzthiazole, and a pyrazole.

10. The substituted hydroquinone or benzoquinone of claim 1, wherein the hydroquinone form is selected from the group consisting of:

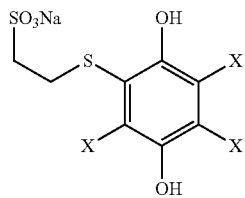

wherein X is a hydrogen, an electron withdrawing group, or an alkyl; and

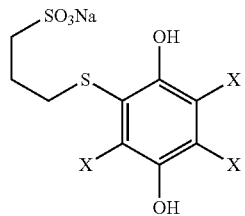

wherein X is a hydrogen, an electron withdrawing group, or an alkyl.

11. The substituted hydroquinone or benzoquinone of claim 10, wherein the electron withdrawing group is selected from the group consisting of nitrile (cyanide), an amide, a ketone, —$CF_3$, —$SF_5$, an imide, an imidazole, a benzimidazole, an oxazole, a benzoxazole, a thiazole, a benzthiazole, and a pyrazole.

12. The substituted hydroquinone or benzoquinone of claim 10, wherein X is methyl.

* * * * *